United States Patent
Kubicek et al.

(10) Patent No.: US 10,864,190 B2
(45) Date of Patent: Dec. 15, 2020

(54) COMBINATION OF AN ANTIANDROGEN WITH A VITAMIN K ANTAGONIST OR WITH A GAMMA-GLUTAMYL CARBOXYLASE INHIBITOR FOR THE THERAPY OF ANDROGEN RECEPTOR POSITIVE CANCER

(71) Applicant: CeMM—Forschungszentrum für Molekulare Medizin GmbH, Vienna (AT)

(72) Inventors: Stefan Kubicek, Vienna (AT); Marco Licciardello, London (GB)

(73) Assignee: CEMM—FORSCHUNGSZENTRUM FÜR MOLEKULARE MEDIZIN GMBH, Vienna (AT)

( * ) Notice: Subject to any disclaimer, the term of this patent is extended or adjusted under 35 U.S.C. 154(b) by 0 days.

(21) Appl. No.: 15/568,330

(22) PCT Filed: Apr. 22, 2016

(86) PCT No.: PCT/EP2016/058990
§ 371 (c)(1),
(2) Date: Oct. 20, 2017

(87) PCT Pub. No.: WO2016/170102
PCT Pub. Date: Oct. 27, 2016

(65) Prior Publication Data
US 2018/0177759 A1 Jun. 28, 2018

(30) Foreign Application Priority Data
Apr. 22, 2015 (EP) .................................. 15164648

(51) Int. Cl.
*A61K 31/37* (2006.01)
*A61K 31/167* (2006.01)
*A61P 35/00* (2006.01)
*A61K 31/4166* (2006.01)

(52) U.S. Cl.
CPC ........... *A61K 31/37* (2013.01); *A61K 31/167* (2013.01); *A61K 31/4166* (2013.01); *A61P 35/00* (2018.01)

(58) Field of Classification Search
CPC .. A61K 31/37; A61K 31/4166; A61K 31/167; A61P 35/00
See application file for complete search history.

(56) References Cited

U.S. PATENT DOCUMENTS

| | | | |
|---|---|---|---|
| 2004/0047852 A1* | 3/2004 | Kennedy | A61K 31/28 424/94.4 |
| 2010/0152298 A1* | 6/2010 | Al-Saeedi | A61K 31/167 514/629 |
| 2014/0037715 A1 | 2/2014 | Wang | |

OTHER PUBLICATIONS

Licciardello et al., "A combinatorial screen of the CLOUD uncovers a synergy targeting the androgen receptor," *Nature Chemical Biology*, 13:771-778, 2017.
Extended European Search Report issued in corresponding European Application No. 15164648.6, dated Oct. 8, 2015.
International Preliminary Report on Patentability issued in corresponding International Application No. PCT/EP2016/058990, dated Nov. 2, 2017.
International Search Report and Written Opinion issued in corresponding International Application No. PCT/EP2016/058990, dated Aug. 29, 2016.
Kapoor et al., "Disulfiram and its emerging role as an adjunctive anti-neoplastic agent," *Chem. Biol. Interact.*, 204(3):200, 2013.
Ketola et al., "Chemical Biology Drug Sensitivity Screen Identifies Sunitinib as Synergystic Agent with Disulfiram in Prostate Cancer Cells," *PLoS One*, 7(12):e51470, 2012.
Lin et al., "Disulfiram is a DNA demethylating agent and inhibits prostate cancer cell growth," *Prostate*, 71(4):333-343, 2011.
Pottegård et al., "Cancer risk in long-term users of vitamin K antagonists: A population-based case-control study," *Int. J. Cancer*, 132(11):2606-2612, 2013.
Watanabe et al., "Human Arylacetamide Deacetylase is a Principal Enzyme in Flutamide Hydrolysis," *Drug Metab. Dispos.*, 37(7):1513-1520, 2009.
Wirth et al., "Antiandrogens in the Treatment of Prostate Cancer," *Eur. Urol.*, 51(2):306-314, 2006.

* cited by examiner

*Primary Examiner* — Sarah Pihonak
*Assistant Examiner* — Jason Deck
(74) *Attorney, Agent, or Firm* — Parker Highlander PLLC

(57) ABSTRACT

The present invention relates to the combination of an antiandrogen with a vitamin K antagonist or with a γ-glutamyl carboxylase inhibitor for use in the treatment or prevention of an androgen receptor positive cancer, such as prostate cancer, or a hyperactive androgen receptor signaling disease/disorder. The invention also relates to a vitamin K antagonist or a γ-glutamyl carboxylase inhibitor for use in resensitizing an antiandrogen-resistant prostate cancer to the treatment with an antiandrogen. The invention further provides a pharmaceutical composition comprising an antiandrogen, a vitamin K antagonist or a γ-glutamyl carboxylase inhibitor, and a pharmaceutically acceptable excipient.

5 Claims, 62 Drawing Sheets

Specification includes a Sequence Listing.

A)

B)

Figure 1:
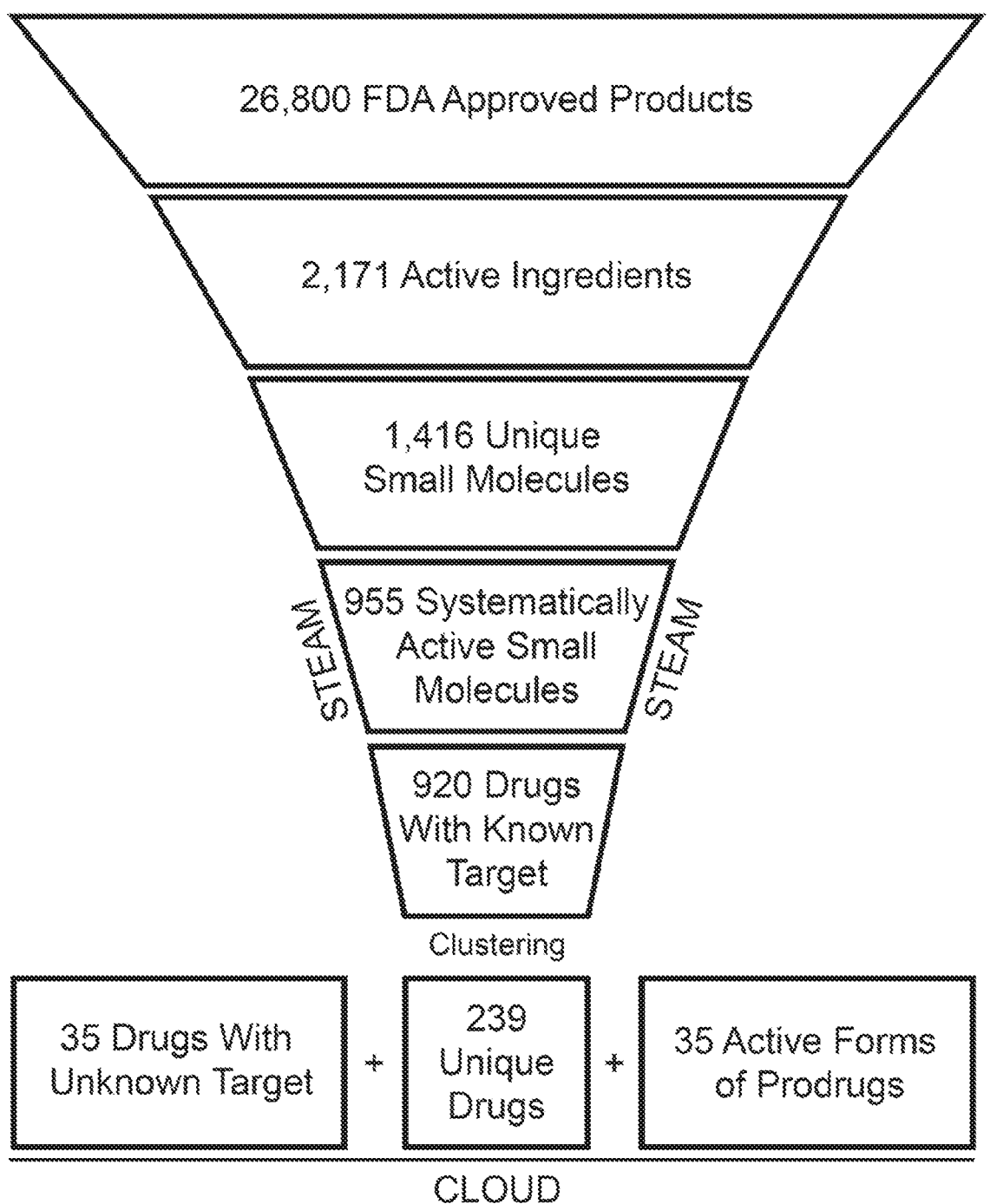
Figure 1:
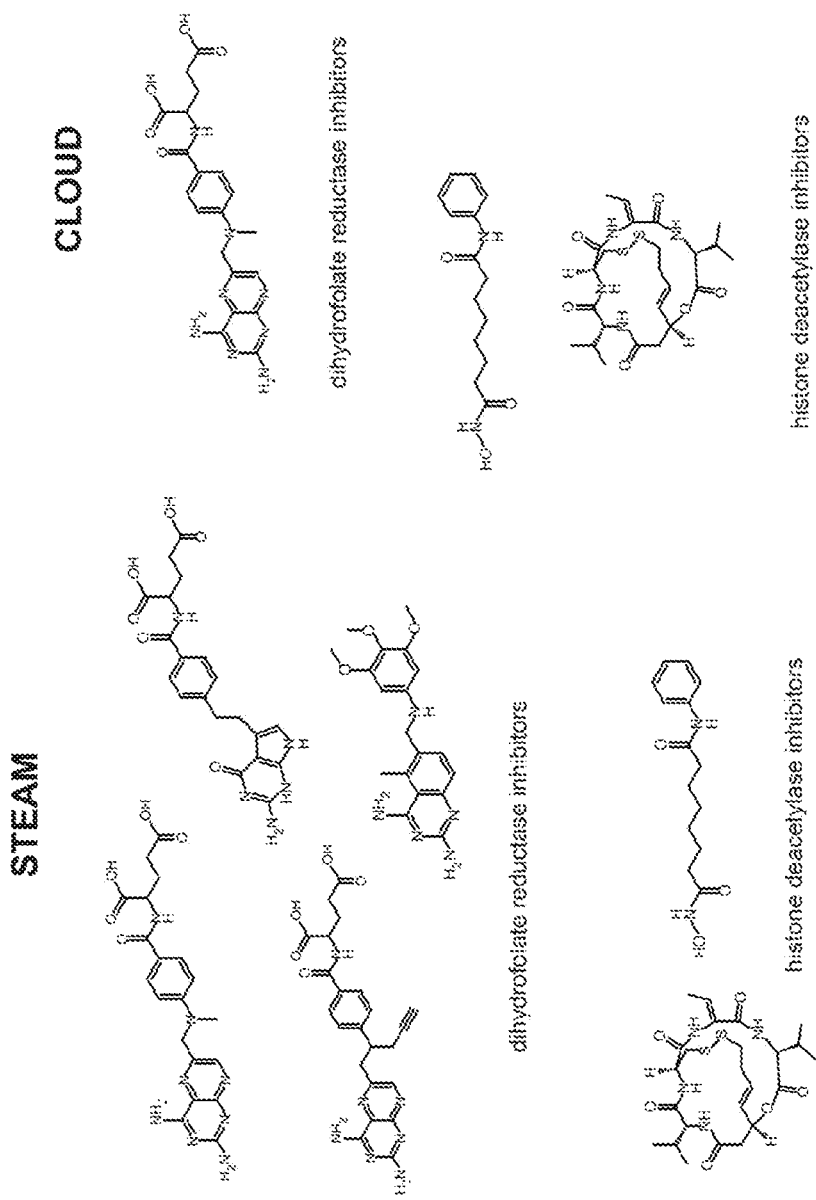

Fig. 1 (cont.)
C)
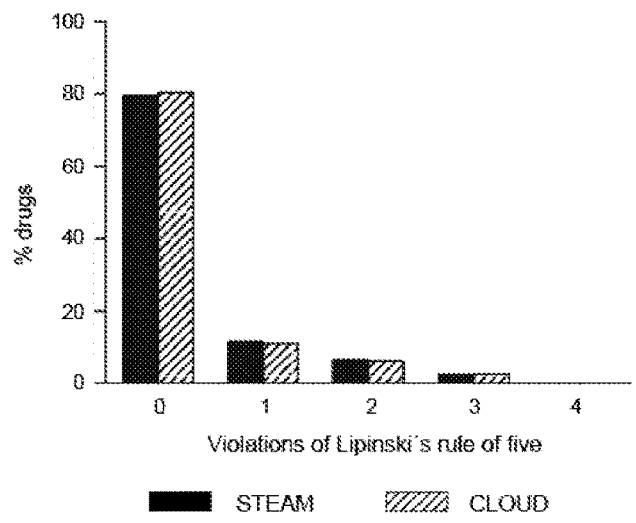
D)
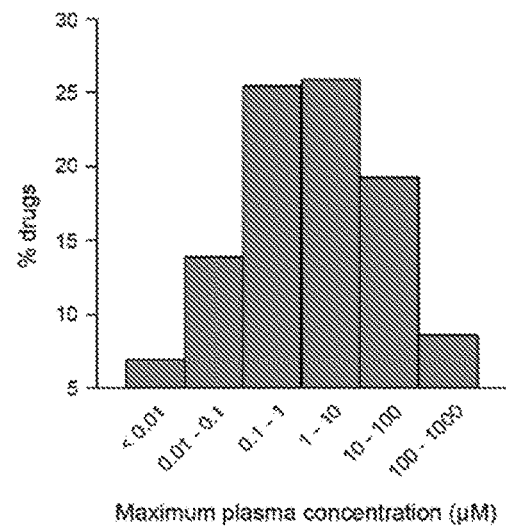
E)
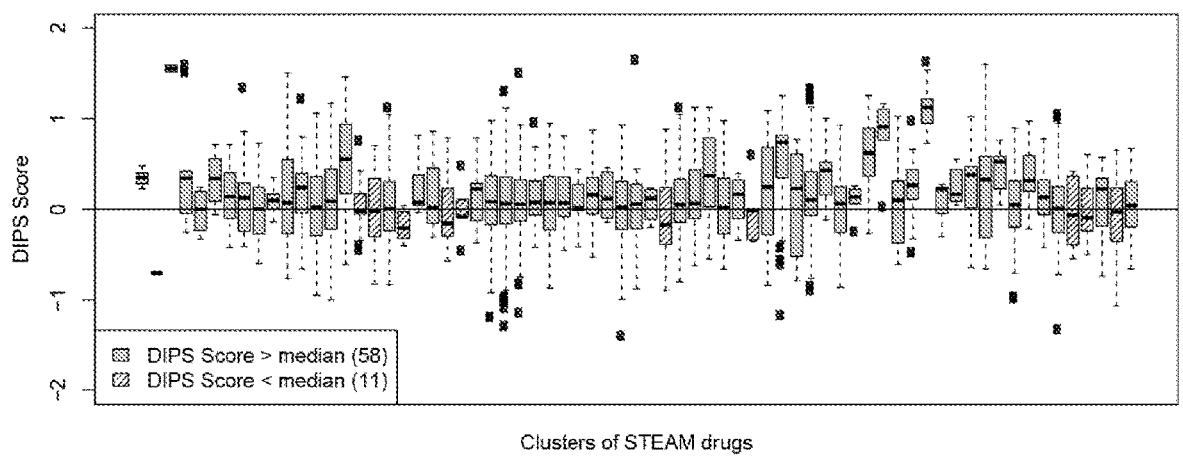

Fig. 1 (cont.)

F)

| STEAM DRUG | MECHANISM OF ACTION | CLUSTER | CLOUD ID | PLASMA [µM] | SCREEN [µM] |
|---|---|---|---|---|---|
| Trilostane | 3-beta-hydroxysteroid dehydrogenase inhibitor | 1 | CLOUD195 | 1.7 | 8.5 |
| Nitisinone | 4-hydroxyphenylpyruvate dioxygenase inhibitor | 2 | CLOUD190 | 23.7 | 118.6 |
| Probucol | ATP-binding cassette transporter blocker | 3 | CLOUD224 | 7.6 | 37.7 |
| Minoxidil | ATP-sensitive inward rectifier potassium channel opener | 4 | CLOUD040 | 1.2 | 6.0 |
| Pinacidil | ATP-sensitive inward rectifier potassium channel opener | 4 | CLOUD258 | 1.7 | 8.3 |
| Carboplatin | DNA alkylating-like | 5 | CLOUD250 | 67.0 | 67.0 |
| Cisplatin | DNA alkylating-like | 5 | | | |
| Oxaliplatin | DNA alkylating-like | 5 | | | |
| Busulfan | DNA alkylator | 6 | CLOUD041 | 0.28 | 1.4 |
| Chlorambucil | DNA alkylator | 6 | CLOUD046 | 1.6 | 8.1 |
| Procarbazine | DNA alkylator | 6 | CLOUD099 | 2.7 | 13.3 |
| Temozolomide | DNA alkylator | 6 | CLOUD164 | 70.6 | 352.9 |
| Altretamine | DNA alkylator | 6 | CLOUD182 | 98.9 | 49.5 |
| Carmustine | DNA alkylator | 6 | CLOUD225 | 0.040 | 0.18 |
| Thiotepa | DNA alkylator | 6 | CLOUD277 | 9.7 | 8.5 |
| Azathioprine | DNA alkylator | 6 | | | |
| Bendamustine | DNA alkylator | 6 | | | |
| Cyclophosphamide | DNA alkylator | 6 | | | |
| Dacarbazine | DNA alkylator | 6 | | | |
| Estramustine | DNA alkylator | 6 | | | |
| Ifosfamide | DNA alkylator | 6 | | | |
| Lomustine | DNA alkylator | 6 | | | |
| Mechlorethamine | DNA alkylator | 6 | | | |
| Melphalan | DNA alkylator | 6 | | | |
| Streptozocin | DNA alkylator | 6 | | | |
| Uracil Mustard | DNA alkylator | 6 | | | |
| Pipobroman | DNA alkylator | 6 | | | |
| Trioxsalen | DNA intercalator | 7 | CLOUD074 | 0.010 | 0.10 |
| Plicamycin | DNA intercalator | 7 | | | |
| Thioguanine | DNA intercalator | 7 | | | |

Fig. 1 (cont.)

F)

| | | | | | |
|---|---|---|---|---|---|
| Doxorubicin | DNA intercalator; topoisomerase inhibitor | 8 | CLOUD053 | 0.040 | 0.20 |
| Daunorubicin | DNA intercalator; topoisomerase inhibitor | 8 | | | |
| Epirubicin | DNA intercalator; topoisomerase inhibitor | 8 | | | |
| Idarubicin | DNA intercalator; topoisomerase inhibitor | 8 | | | |
| Valrubicin | DNA intercalator; topoisomerase inhibitor | 8 | | | |
| Azacitidine | DNA methyltransferase inhibitor | 9 | CLOUD115 | 3.1 | 15.4 |
| Decitabine | DNA methyltransferase inhibitor | 9 | | | |
| Cytarabine | DNA polymerase inhibitor | 10 | CLOUD057 | 2.1 | 10.3 |
| Fludarabine | DNA polymerase inhibitor | 10 | | | |
| Methyldopa | DOPA decarboxylase inhibitor | 11 | CLOUD186 | 23.7 | 118.4 |
| Carbidopa | DOPA decarboxylase inhibitor | 11 | | | |
| Valproate | GABA aminotransferase inhibitor | 12 | CLOUD249 | 693.4 | 3467.1 |
| Vigabatrin | GABA aminotransferase inhibitor | 12 | | | |
| Ezetimibe | Niemann-Pick C1-Like 1 protein inhibitor | 13 | CLOUD066 | 0.17 | 0.90 |
| Clopidogrel | P2Y receptor antagonist | 14 | CLOUD019 | 0.020 | 0.10 |
| Prasugrel | P2Y receptor antagonist | 14 | | | |
| Ticlopidine | P2Y receptor antagonist | 14 | | | |
| Pyridostigmine Bromide | acetylcholinesterase inhibitor | 15 | CLOUD009 | 1.1 | 5.5 |
| Tacrine | acetylcholinesterase inhibitor | 15 | CLOUD091 | 0.050 | 0.30 |
| Galantamine | acetylcholinesterase inhibitor | 15 | CLOUD116 | 4.0 | 20.0 |
| Ambenonium | acetylcholinesterase inhibitor | 15 | | | |
| Donepezil | acetylcholinesterase inhibitor | 15 | | | |
| Edrophonium | acetylcholinesterase inhibitor | 15 | | | |
| Hexafluorenium | acetylcholinesterase inhibitor | 15 | | | |
| Rivastigmine | acetylcholinesterase inhibitor | 15 | | | |
| Pentostatin | adenosine deaminase inhibitor | 16 | CLOUD138 | 11.2 | 55.9 |
| Theophylline | adenosine receptor antagonist; phosphodiesterase inhibitor | 17 | CLOUD251 | 111.0 | 104.1 |
| Aminophylline | adenosine receptor antagonist; phosphodiesterase inhibitor | 17 | | | |
| Oxtriphylline | adenosine receptor antagonist; phosphodiesterase inhibitor | 17 | | | |

Fig. 1 (cont.)

F)

| | | | | | |
|---|---|---|---|---|---|
| Dexmedetomidine | adrenergic receptor agonist | 18 | CLOUD004 | 0.010 | 0.042 |
| Isoproterenol | adrenergic receptor agonist | 18 | CLOUD082 | 2.4 | 11.8 |
| Epinephrine | adrenergic receptor agonist | 18 | CLOUD133 | 5.5 | 27.3 |
| Guanfacine | adrenergic receptor agonist | 18 | CLOUD273 | 0.020 | 10.0 |
| Arbutamine | adrenergic receptor agonist | 18 | | | |
| Clonidine | adrenergic receptor agonist | 18 | | | |
| Dobutamine | adrenergic receptor agonist | 18 | | | |
| Guanabenz | adrenergic receptor agonist | 18 | | | |
| Mephentermine | adrenergic receptor agonist | 18 | | | |
| Metaraminol | adrenergic receptor agonist | 18 | | | |
| Methoxamine | adrenergic receptor agonist | 18 | | | |
| Midodrine | adrenergic receptor agonist | 18 | | | |
| Norepinephrine | adrenergic receptor agonist | 18 | | | |
| Phenylephrine | adrenergic receptor agonist | 18 | | | |
| Phenylpropanolamine | adrenergic receptor agonist | 18 | | | |
| Protokylol | adrenergic receptor agonist | 18 | | | |
| Pseudoephedrine | adrenergic receptor agonist | 18 | | | |
| Ritodrine | adrenergic receptor agonist | 18 | | | |
| Salbutamol | adrenergic receptor agonist | 18 | | | |
| Terbutaline | adrenergic receptor agonist | 18 | | | |
| Tetrahydrozoline | adrenergic receptor agonist | 18 | | | |
| Tizanidine | adrenergic receptor agonist | 18 | | | |
| Dihydroergotamine | adrenergic receptor agonist; adrenergic receptor antagonist | 19 | CLOUD069 | 0.015 | 0.10 |
| Ergotamine | adrenergic receptor agonist; adrenergic receptor antagonist | 19 | | | |
| Terazosin | adrenergic receptor antagonist | 20 | CLOUD110 | 0.21 | 1.0 |
| Atenolol | adrenergic receptor antagonist | 20 | CLOUD124 | 3.8 | 18.8 |
| Tolazoline | adrenergic receptor antagonist | 20 | CLOUD125 | 25.0 | 124.9 |
| Acebutolol | adrenergic receptor antagonist | 20 | | | |
| Alfuzosin | adrenergic receptor antagonist | 20 | | | |
| Betaxolol | adrenergic receptor antagonist | 20 | | | |
| Bethanidine | adrenergic receptor antagonist | 20 | | | |
| Bisoprolol | adrenergic receptor antagonist | 20 | | | |
| Carvedilol | adrenergic receptor antagonist | 20 | | | |

Fig. 1 (cont.)

F)

| | | | | | |
|---|---|---|---|---|---|
| Doxazosin | adrenergic receptor antagonist | 20 | | | |
| Ergoloid | adrenergic receptor antagonist | 20 | | | |
| Esmolol | adrenergic receptor antagonist | 20 | | | |
| Labetalol | adrenergic receptor antagonist | 20 | | | |
| Metoprolol | adrenergic receptor antagonist | 20 | | | |
| Nadolol | adrenergic receptor antagonist | 20 | | | |
| Nebivolol | adrenergic receptor antagonist | 20 | | | |
| Oxprenolol | adrenergic receptor antagonist | 20 | | | |
| Penbutolol | adrenergic receptor antagonist | 20 | | | |
| Phenoxybenzamine | adrenergic receptor antagonist | 20 | | | |
| Phentolamine | adrenergic receptor antagonist | 20 | | | |
| Pindolol | adrenergic receptor antagonist | 20 | | | |
| Prazosin | adrenergic receptor antagonist | 20 | | | |
| Propranolol | adrenergic receptor antagonist | 20 | | | |
| Silodosin | adrenergic receptor antagonist | 20 | | | |
| Tamsulosin | adrenergic receptor antagonist | 20 | | | |
| Timolol | adrenergic receptor antagonist | 20 | | | |
| Propiomazine | adrenergic receptor antagonist | 20 | | | |
| Thiethylperazine | adrenergic receptor antagonist | 20 | | | |
| Mirtazapine | adrenergic receptor antagonist | 20 | | | |
| Fomepizole | alcohol dehydrogenase inhibitor | 21 | CLOUD242 | 299.6 | 1498.2 |
| Disulfiram | aldehyde dehydrogenase inhibitor | 22 | CLOUD062 | 1.4 | 6.7 |
| Acarbose | alpha glucosidase inhibitor | 23 | CLOUD075 | 0.44 | 2.2 |
| Miglitol | alpha glucosidase inhibitor | 23 | CLOUD159 | 9.1 | 43.4 |
| Amiloride | amiloride-sensitive sodium channel inhibitor | 24 | CLOUD017 | 0.22 | 1.1 |

Fig. 1 (cont.)

F)

| Triamterene | amiloride-sensitive sodium channel inhibitor | 24 | CLOUD054 | 0.39 | 2.0 |
|---|---|---|---|---|---|
| Testosterone | androgen receptor agonist | 25 | CLOUD051 | 0.030 | 0.20 |
| Stanozolol | androgen receptor agonist | 25 | CLOUD158 | 12.5 | 57.8 |
| Danazol | androgen receptor agonist | 25 | | | |
| Dromostanolone | androgen receptor agonist | 25 | | | |
| Ethylestrenol | androgen receptor agonist | 25 | | | |
| Fluoxymesterone | androgen receptor agonist | 25 | | | |
| Methyltestosterone | androgen receptor agonist | 25 | | | |
| Nandrolone | androgen receptor agonist | 25 | | | |
| Oxandrolone | androgen receptor agonist | 25 | | | |
| Oxymetholone | androgen receptor agonist | 25 | | | |
| Flutamide | androgen receptor antagonist | 26 | CLOUD142 | 5.4 | 27.2 |
| Bicalutamide | androgen receptor antagonist | 26 | | | |
| Nilutamide | androgen receptor antagonist | 26 | | | |
| Enalaprilat | angiotensin converting enzyme inhibitor | 27 | CLOUD095 | 0.14 | 0.70 |
| Benazepril | angiotensin converting enzyme inhibitor | 27 | | | |
| Captopril | angiotensin converting enzyme inhibitor | 27 | | | |
| Deserpidine | angiotensin converting enzyme inhibitor | 27 | | | |
| Enalapril | angiotensin converting enzyme inhibitor | 27 | | | |
| Fosinopril | angiotensin converting enzyme inhibitor | 27 | | | |
| Lisinopril | angiotensin converting enzyme inhibitor | 27 | | | |
| Moexipril | angiotensin converting enzyme inhibitor | 27 | | | |
| Perindopril | angiotensin converting enzyme inhibitor | 27 | | | |
| Quinapril | angiotensin converting enzyme inhibitor | 27 | | | |
| Ramipril | angiotensin converting enzyme inhibitor | 27 | | | |
| Rescinnamine | angiotensin converting enzyme inhibitor | 27 | | | |
| Spirapril | angiotensin converting enzyme inhibitor | 27 | | | |
| Trandolapril | angiotensin converting enzyme inhibitor | 27 | | | |

Fig. 1 (cont.)

F)

| | | | | | |
|---|---|---|---|---|---|
| Olmesartan Medoxomil | angiotensin receptor antagonist | 28 | CLOUD093 | 1.3 | 6.7 |
| Candesartan | angiotensin receptor antagonist | 28 | | | |
| Eprosartan | angiotensin receptor antagonist | 28 | | | |
| Irbesartan | angiotensin receptor antagonist | 28 | | | |
| Losartan | angiotensin receptor antagonist | 28 | | | |
| Telmisartan | angiotensin receptor antagonist | 28 | | | |
| Valsartan | angiotensin receptor antagonist | 28 | | | |
| Anastrozole | aromatase inhibitor | 29 | CLOUD085 | 0.10 | 0.50 |
| Testolactone | aromatase inhibitor | 29 | CLOUD281 | 10.0 | 10.0 |
| Aminoglutethimide | aromatase inhibitor | 29 | | | |
| Exemestane | aromatase inhibitor | 29 | | | |
| Letrozole | aromatase inhibitor | 29 | | | |
| Metronidazole | bacterial DNA alkylator | 30 | CLOUD170 | 58.4 | 292.1 |
| Furazolidone | bacterial DNA intercalator | 31 | CLOUD135 | 4.4 | 10.9 |
| Clofazimine | bacterial DNA intercalator | 31 | | | |
| Mitomycin | bacterial DNA intercalator | 31 | | | |
| Isoniazid | bacterial InhA inhibitor | 32 | CLOUD171 | 72.9 | 364.6 |
| Ethionamide | bacterial InhA inhibitor | 32 | | | |
| Rifabutin | bacterial RNA polymerase inhibitor | 33 | CLOUD086 | 0.18 | 0.90 |
| Rifapentine | bacterial RNA polymerase inhibitor | 33 | | | |
| Rifaximin | bacterial RNA polymerase inhibitor | 33 | | | |
| D-Cycloserine | bacterial alanine racemase inhibitor; bacterial D-alanine--D-alanine ligase inhibitor | 34 | CLOUD177 | 98.0 | 122.4 |
| Ethambutol | bacterial arabinosyltransferase inhibitor | 35 | CLOUD185 | 29.4 | 146.8 |
| Sulbactam | bacterial beta-lactamase inhibitor | 36 | CLOUD214 | 343.0 | 1714.9 |
| Clavulanate | bacterial beta-lactamase inhibitor | 36 | | | |
| Tazobactam | bacterial beta-lactamase inhibitor | 36 | | | |
| Trimethoprim | bacterial dihydrofolate reductase inhibitor | 37 | CLOUD144 | 8.6 | 43.1 |

Fig. 1 (cont.)

F)

| | | | | | |
|---|---|---|---|---|---|
| Pyrimethamine | bacterial dihydrofolate reductase inhibitor | 37 | | | |
| Sulfameter | bacterial dihydropteroate synthase inhibitor | 38 | CLOUD161 | 321.1 | 1604.7 |
| Sulfacytine | bacterial dihydropteroate synthase inhibitor | 38 | | | |
| Sulfadiazine | bacterial dihydropteroate synthase inhibitor | 38 | | | |
| Sulfadoxine | bacterial dihydropteroate synthase inhibitor | 38 | | | |
| Sulfamerazine | bacterial dihydropteroate synthase inhibitor | 38 | | | |
| Sulfamethazine | bacterial dihydropteroate synthase inhibitor | 38 | | | |
| Sulfamethizole | bacterial dihydropteroate synthase inhibitor | 38 | | | |
| Sulfamethoxazole | bacterial dihydropteroate synthase inhibitor | 38 | | | |
| Sulfaphenazole | bacterial dihydropteroate synthase inhibitor | 38 | | | |
| Sulfapyridine | bacterial dihydropteroate synthase inhibitor | 38 | | | |
| Sulfathiazole | bacterial dihydropteroate synthase inhibitor | 38 | | | |
| Sulfisoxazole | bacterial dihydropteroate synthase inhibitor | 38 | | | |
| Sulfoxone | bacterial dihydropteroate synthase inhibitor | 38 | | | |
| Fosfomycin | bacterial enolpyruvate transferase inhibitor | 39 | CLOUD252 | 231.8 | 3.1 |
| Pyrazinamide | bacterial fatty acid synthase inhibitor | 40 | CLOUD245 | 609.2 | 609.3 |
| Mycophenolic Acid | bacterial inosine-5-monophosphate dehydrogenase inhibitor | 41 | CLOUD165 | 15.6 | 78.0 |
| Cefmenoxime | bacterial penicillin-binding protein inhibitor | 42 | CLOUD216 | 183.8 | 918.8 |
| Amdinocillin | bacterial penicillin-binding protein inhibitor | 42 | | | |
| Amoxicillin | bacterial penicillin-binding protein inhibitor | 42 | | | |
| Ampicillin | bacterial penicillin-binding protein inhibitor | 42 | | | |

Fig. 1 (cont.)

F)

| | | | | | |
|---|---|---|---|---|---|
| Azlocillin | bacterial penicillin-binding protein inhibitor | 42 | | | |
| Aztreonam | bacterial penicillin-binding protein inhibitor | 42 | | | |
| Bacampicillin | bacterial penicillin-binding protein inhibitor | 42 | | | |
| Benzylpenicillin | bacterial penicillin-binding protein inhibitor | 42 | | | |
| Carbenicillin | bacterial penicillin-binding protein inhibitor | 42 | | | |
| Cefaclor | bacterial penicillin-binding protein inhibitor | 42 | | | |
| Cefadroxil | bacterial penicillin-binding protein inhibitor | 42 | | | |
| Cefalotin | bacterial penicillin-binding protein inhibitor | 42 | | | |
| Cefamandole | bacterial penicillin-binding protein inhibitor | 42 | | | |
| Cefazolin | bacterial penicillin-binding protein inhibitor | 42 | | | |
| Cefdinir | bacterial penicillin-binding protein inhibitor | 42 | | | |
| Cefditoren | bacterial penicillin-binding protein inhibitor | 42 | | | |
| Cefepime | bacterial penicillin-binding protein inhibitor | 42 | | | |
| Cefixime | bacterial penicillin-binding protein inhibitor | 42 | | | |
| Cefmetazole | bacterial penicillin-binding protein inhibitor | 42 | | | |
| Cefonicid | bacterial penicillin-binding protein inhibitor | 42 | | | |
| Cefoperazone | bacterial penicillin-binding protein inhibitor | 42 | | | |
| Ceforanide | bacterial penicillin-binding protein inhibitor | 42 | | | |
| Cefotaxime | bacterial penicillin-binding protein inhibitor | 42 | | | |
| Cefotetan | bacterial penicillin-binding protein inhibitor | 42 | | | |
| Cefotiam | bacterial penicillin-binding protein inhibitor | 42 | | | |

Fig. 1 (cont.)

F)

| | | | | | |
|---|---|---|---|---|---|
| Cefoxitin | bacterial penicillin-binding protein inhibitor | 42 | | | |
| Cefpiramide | bacterial penicillin-binding protein inhibitor | 42 | | | |
| Cefpodoxime | bacterial penicillin-binding protein inhibitor | 42 | | | |
| Cefprozil | bacterial penicillin-binding protein inhibitor | 42 | | | |
| Cefradine | bacterial penicillin-binding protein inhibitor | 42 | | | |
| Ceftazidime | bacterial penicillin-binding protein inhibitor | 42 | | | |
| Ceftibuten | bacterial penicillin-binding protein inhibitor | 42 | | | |
| Ceftizoxime | bacterial penicillin-binding protein inhibitor | 42 | | | |
| Ceftriaxone | bacterial penicillin-binding protein inhibitor | 42 | | | |
| Cefuroxime | bacterial penicillin-binding protein inhibitor | 42 | | | |
| Cephalexin | bacterial penicillin-binding protein inhibitor | 42 | | | |
| Cephaloglycin | bacterial penicillin-binding protein inhibitor | 42 | | | |
| Cephapirin | bacterial penicillin-binding protein inhibitor | 42 | | | |
| Cloxacillin | bacterial penicillin-binding protein inhibitor | 42 | | | |
| Cyclacillin | bacterial penicillin-binding protein inhibitor | 42 | | | |
| Dicloxacillin | bacterial penicillin-binding protein inhibitor | 42 | | | |
| Doripenem | bacterial penicillin-binding protein inhibitor | 42 | | | |
| Ertapenem | bacterial penicillin-binding protein inhibitor | 42 | | | |
| Hetacillin | bacterial penicillin-binding protein inhibitor | 42 | | | |
| Imipenem | bacterial penicillin-binding protein inhibitor | 42 | | | |
| Loracarbef | bacterial penicillin-binding protein inhibitor | 42 | | | |

Fig. 1 (cont.)

F)

| | | | | | |
|---|---|---|---|---|---|
| Meropenem | bacterial penicillin-binding protein inhibitor | 42 | | | |
| Methicillin | bacterial penicillin-binding protein inhibitor | 42 | | | |
| Mezlocillin | bacterial penicillin-binding protein inhibitor | 42 | | | |
| Moxalactam | bacterial penicillin-binding protein inhibitor | 42 | | | |
| Nafcillin | bacterial penicillin-binding protein inhibitor | 42 | | | |
| Oxacillin | bacterial penicillin-binding protein inhibitor | 42 | | | |
| Penicillin G | bacterial penicillin-binding protein inhibitor | 42 | | | |
| Penicillin V | bacterial penicillin-binding protein inhibitor | 42 | | | |
| Piperacillin | bacterial penicillin-binding protein inhibitor | 42 | | | |
| Ticarcillin | bacterial penicillin-binding protein inhibitor | 42 | | | |
| Azithromycin | bacterial ribosome inhibitor | 43 | CLOUD081 | 1.3 | 6.7 |
| Tetracycline | bacterial ribosome inhibitor | 43 | CLOUD160 | 9.0 | 45.0 |
| Amikacin | bacterial ribosome inhibitor | 43 | | | |
| Capreomycin | bacterial ribosome inhibitor | 43 | | | |
| Clarithromycin | bacterial ribosome inhibitor | 43 | | | |
| Clindamycin | bacterial ribosome inhibitor | 43 | | | |
| Dalfopristin | bacterial ribosome inhibitor | 43 | | | |
| Demeclocycline | bacterial ribosome inhibitor | 43 | | | |
| Dirithromycin | bacterial ribosome inhibitor | 43 | | | |
| Doxycycline | bacterial ribosome inhibitor | 43 | | | |
| Erythromycin | bacterial ribosome inhibitor | 43 | | | |
| Kanamycin | bacterial ribosome inhibitor | 43 | | | |
| Lincomycin | bacterial ribosome inhibitor | 43 | | | |
| Linezolid | bacterial ribosome inhibitor | 43 | | | |
| Lymecycline | bacterial ribosome inhibitor | 43 | | | |
| Methacycline | bacterial ribosome inhibitor | 43 | | | |
| Minocycline | bacterial ribosome inhibitor | 43 | | | |
| Netilmicin | bacterial ribosome inhibitor | 43 | | | |
| Nitrofurantoin | bacterial ribosome inhibitor | 43 | | | |
| Oxytetracycline | bacterial ribosome inhibitor | 43 | | | |
| Quinupristin | bacterial ribosome inhibitor | 43 | | | |
| Rifampin | bacterial ribosome inhibitor | 43 | | | |
| Spectinomycin | bacterial ribosome inhibitor | 43 | | | |
| Streptomycin | bacterial ribosome inhibitor | 43 | | | |

Fig. 1 (cont.)

F)

| Telithromycin | bacterial ribosome inhibitor | 43 | | | |
|---|---|---|---|---|---|
| Tigecycline | bacterial ribosome inhibitor | 43 | | | |
| Troleandomycin | bacterial ribosome inhibitor | 43 | | | |
| Viomycin | bacterial ribosome inhibitor | 43 | | | |
| Enoxacin | bacterial topoisomerase inhibitor | 44 | CLOUD156 | 12.5 | 62.4 |
| Novobiocin | bacterial topoisomerase inhibitor | 44 | CLOUD231 | 90.6 | 510.1 |
| Alatrofloxacin | bacterial topoisomerase inhibitor | 44 | | | |
| Cinoxacin | bacterial topoisomerase inhibitor | 44 | | | |
| Ciprofloxacin | bacterial topoisomerase inhibitor | 44 | | | |
| Gemifloxacin | bacterial topoisomerase inhibitor | 44 | | | |
| Grepafloxacin | bacterial topoisomerase inhibitor | 44 | | | |
| Levofloxacin | bacterial topoisomerase inhibitor | 44 | | | |
| Lomefloxacin | bacterial topoisomerase inhibitor | 44 | | | |
| Moxifloxacin | bacterial topoisomerase inhibitor | 44 | | | |
| Nalidixic Acid | bacterial topoisomerase inhibitor | 44 | | | |
| Norfloxacin | bacterial topoisomerase inhibitor | 44 | | | |
| Ofloxacin | bacterial topoisomerase inhibitor | 44 | | | |
| Sparfloxacin | bacterial topoisomerase inhibitor | 44 | | | |
| Trovafloxacin | bacterial topoisomerase inhibitor | 44 | | | |
| Acetohydroxamic Acid | bacterial urease inhibitor | 45 | CLOUD227 | 523.5 | 523.5 |
| Bumetanide | bumetanide sensitive sodium-potassium-chloride cotransporter inhibitor | 46 | CLOUD056 | 0.20 | 1.0 |
| Ethacrynic Acid | bumetanide sensitive sodium-potassium-chloride cotransporter inhibitor | 46 | | | |
| Furosemide | bumetanide sensitive sodium-potassium-chloride cotransporter inhibitor | 46 | | | |
| Torasemide | bumetanide sensitive sodium-potassium-chloride cotransporter inhibitor | 46 | | | |

Fig. 1 (cont.)

F)

| Tacrolimus | calcineurin inhibitor | 47 | CLOUD119 | 0.020 | 0.090 |
|---|---|---|---|---|---|
| Cinacalcet | calcium sensing receptor agonist | 48 | CLOUD222 | 0.080 | 0.40 |
| Nabilone | cannabinoid receptor agonist | 49 | CLOUD286 | 0.0054 | 0.027 |
| Marinol | cannabinoid receptor agonist | 49 | | | |
| Carglumic Acid | carbamoyl-phosphate synthase activator | 50 | CLOUD162 | 13.7 | 68.4 |
| Acetazolamide | carbonic anhydrase inhibitor | 51 | CLOUD192 | 90.0 | 90.0 |
| Dichlorphenamide | carbonic anhydrase inhibitor | 51 | CLOUD241 | 214.8 | 214.8 |
| Ethoxzolamide | carbonic anhydrase inhibitor | 51 | | | |
| Methazolamide | carbonic anhydrase inhibitor | 51 | | | |
| Acetohexamide | carbonic anhydrase inhibitor; sulfonylurea receptor agonist | 52 | CLOUD240 | 215.8 | 1079.0 |
| Entacapone | catechol O-methyltransferase inhibitor | 53 | CLOUD076 | 3.3 | 16.4 |
| Tolcapone | catechol O-methyltransferase inhibitor | 53 | | | |
| Miglustat | ceramide glucosyltransferase inhibitor | 54 | CLOUD223 | 92.6 | 92.6 |
| Maraviroc | chemokine receptor antagonist | 55 | CLOUD026 | 2.3 | 11.4 |
| Plerixafor | chemokine receptor antagonist | 55 | CLOUD293 | 5.1 | Not Tested |
| Doxapram | chemoreceptor agonist | 56 | CLOUD157 | 13.2 | 66.1 |
| Oxyphenbutazone | cyclooxygenase inhibitor | 57 | CLOUD193 | 308.3 | 308.3 |
| Fenoprofen | cyclooxygenase inhibitor | 57 | CLOUD230 | 247.7 | 1238.3 |
| Acetaminophen | cyclooxygenase inhibitor | 57 | | | |
| Acetylsalicylic Acid | cyclooxygenase inhibitor | 57 | | | |
| Carprofen | cyclooxygenase inhibitor | 57 | | | |
| Celecoxib | cyclooxygenase inhibitor | 57 | | | |
| Diclofenac | cyclooxygenase inhibitor | 57 | | | |
| Diflunisal | cyclooxygenase inhibitor | 57 | | | |
| Etodolac | cyclooxygenase inhibitor | 57 | | | |
| Flurbiprofen | cyclooxygenase inhibitor | 57 | | | |
| Ibuprofen | cyclooxygenase inhibitor | 57 | | | |
| Indomethacin | cyclooxygenase inhibitor | 57 | | | |
| Ketoprofen | cyclooxygenase inhibitor | 57 | | | |
| Ketorolac | cyclooxygenase inhibitor | 57 | | | |
| Mefenamic Acid | cyclooxygenase inhibitor | 57 | | | |
| Meloxicam | cyclooxygenase inhibitor | 57 | | | |
| Nabumetone | cyclooxygenase inhibitor | 57 | | | |
| Naproxen | cyclooxygenase inhibitor | 57 | | | |
| Oxaprozin | cyclooxygenase inhibitor | 57 | | | |
| Phenylbutazone | cyclooxygenase inhibitor | 57 | | | |
| Piroxicam | cyclooxygenase inhibitor | 57 | | | |

Fig. 1 (cont.)

F)

| | | | | | |
|---|---|---|---|---|---|
| Rofecoxib | cyclooxygenase inhibitor | 57 | | | |
| Sulindac | cyclooxygenase inhibitor | 57 | | | |
| Tolmetin | cyclooxygenase inhibitor | 57 | | | |
| Valdecoxib | cyclooxygenase inhibitor | 57 | | | |
| Meclofenamic Acid | cyclooxygenase inhibitor; phospholipase inhibitor | 58 | CLOUD166 | 16.2 | 81.1 |
| Atovaquone | cytochrome bc1 inhibitor | 59 | CLOUD218 | 37.9 | 47.4 |
| Methotrexate | dihydrofolate reductase inhibitor | 60 | CLOUD089 | 0.090 | 0.40 |
| Pralatrexate | dihydrofolate reductase inhibitor | 60 | | | |
| Trimetrexate | dihydrofolate reductase inhibitor | 60 | | | |
| Pemetrexed | dihydrofolate reductase inhibitor | 60 | | | |
| Leflunomide | dihydroorotate dehydrogenase inhibitor | 61 | CLOUD243 | 66.6 | 333.1 |
| Sitagliptin | dipeptidyl peptidase 4 inhibitor | 62 | CLOUD061 | 0.95 | 4.8 |
| Saxagliptin | dipeptidyl peptidase 4 inhibitor | 62 | CLOUD065 | 0.080 | 0.40 |
| Pramipexole | dopamine receptor agonist | 63 | CLOUD011 | 0.030 | 0.20 |
| Dopamine | dopamine receptor agonist | 63 | CLOUD023 | 0.50 | 2.5 |
| Apomorphine | dopamine receptor agonist | 63 | | | |
| Bromocriptine | dopamine receptor agonist | 63 | | | |
| Cabergoline | dopamine receptor agonist | 63 | | | |
| Levodopa | dopamine receptor agonist | 63 | | | |
| Pergolide | dopamine receptor agonist | 63 | | | |
| Ropinirole | dopamine receptor agonist | 63 | | | |
| Rotigotine | dopamine receptor agonist | 63 | | | |
| Methylergonovine | dopamine receptor agonist; dopamine receptor antagonist | 64 | CLOUD126 | 0.010 | 0.044 |
| Aripiprazole | dopamine receptor agonist; dopamine receptor antagonist; serotonin receptor agonist; serotonin receptor antagonist | 65 | CLOUD084 | 0.67 | 3.3 |
| Trifluoperazine | dopamine receptor antagonist | 66 | CLOUD025 | 0.020 | 0.10 |
| Acetophenazine | dopamine receptor antagonist | 66 | | | |
| Carphenazine | dopamine receptor antagonist | 66 | | | |
| Chlorprothixene | dopamine receptor antagonist | 66 | | | |
| Droperidol | dopamine receptor antagonist | 66 | | | |
| Fenoldopam | dopamine receptor antagonist | 66 | | | |
| Fluphenazine | dopamine receptor antagonist | 66 | | | |
| Haloperidol | dopamine receptor antagonist | 66 | | | |
| Loxapine | dopamine receptor antagonist | 66 | | | |
| Metoclopramide | dopamine receptor antagonist | 66 | | | |

Fig. 1 (cont.)

F)

| | | | | | |
|---|---|---|---|---|---|
| Molindone | dopamine receptor antagonist | 66 | | | |
| Perphenazine | dopamine receptor antagonist | 66 | | | |
| Pimozide | dopamine receptor antagonist | 66 | | | |
| Prochlorperazine | dopamine receptor antagonist | 66 | | | |
| Thioridazine | dopamine receptor antagonist | 66 | | | |
| Thiothixene | dopamine receptor antagonist | 66 | | | |
| Clozapine | dopamine receptor antagonist | 66 | | | |
| Iloperidone | dopamine receptor antagonist | 66 | | | |
| Mesoridazine | dopamine receptor antagonist | 66 | | | |
| Paliperidone | dopamine receptor antagonist | 66 | | | |
| Quetiapine | dopamine receptor antagonist | 66 | | | |
| Olanzapine | dopamine receptor antagonist | 66 | | | |
| Triflupromazine | dopamine receptor antagonist; histamine receptor antagonist; serotonin receptor antagonist; muscarinic acetylcholine receptor antagonist; alpha adrenergic receptor antagonist | 67 | CLOUD256 | 0.28 | 1.4 |
| Chlorpromazine | dopamine receptor antagonist; histamine receptor antagonist; serotonin receptor antagonist; muscarinic acetylcholine receptor antagonist; alpha adrenergic receptor antagonist | 67 | | | |
| Promazine | dopamine receptor antagonist; histamine receptor antagonist; serotonin receptor antagonist; muscarinic acetylcholine receptor antagonist; alpha adrenergic receptor antagonist | 67 | | | |
| Armodafinil | dopamine transporter inhibitor | 68 | CLOUD201 | 27.1 | 27.1 |
| Methylphenidate | dopamine transporter inhibitor | 68 | | | |
| Bupropion | dopamine transporter inhibitor | 68 | | | |
| Amphetamine | dopamine transporter substrate; norepinephrine transporter substrate | 69 | Controlled | | |
| Benzphetamine | dopamine transporter substrate; norepinephrine transporter substrate | 69 | Controlled | | |
| Dextroamphetamine | dopamine transporter substrate; norepinephrine transporter substrate | 69 | Controlled | | |

Fig. 1 (cont.)

F)

| | | | | | |
|---|---|---|---|---|---|
| Lisdexamfetamine | dopamine transporter substrate; norepinephrine transporter substrate | 69 | Controlled | | |
| Methamphetamine | dopamine transporter substrate; norepinephrine transporter substrate | 69 | Controlled | | |
| Phenmetrazine | dopamine transporter substrate; norepinephrine transporter substrate | 69 | Controlled | | |
| Bosentan | endothelin receptor antagonist | 70 | CLOUD206 | 6.7 | 10.0 |
| Ambrisentan | endothelin receptor antagonist | 70 | | | |
| Ethinyl Estradiol | estrogen receptor agonist | 71 | CLOUD088 | 0.00046 | 0.0023 |
| Chlorotrianisene | estrogen receptor agonist | 71 | | | |
| Diethylstilbestrol | estrogen receptor agonist | 71 | | | |
| Estradiol | estrogen receptor agonist | 71 | | | |
| Estrone | estrogen receptor agonist | 71 | | | |
| Mestranol | estrogen receptor agonist | 71 | | | |
| Polyestradiol | estrogen receptor agonist | 71 | | | |
| Quinestrol | estrogen receptor agonist | 71 | | | |
| Clomifene | estrogen receptor agonist | 71 | | | |
| Raloxifene | estrogen receptor agonist | 71 | | | |
| Toremifene | estrogen receptor agonist | 71 | | | |
| Tamoxifen | estrogen receptor antagonist | 72 | CLOUD064 | 1.4 | 6.7 |
| Fulvestrant | estrogen receptor antagonist | 72 | | | |
| Itraconazole | fungal lanosterol 14-alpha demethylase inhibitor | 73 | CLOUD113 | 2.8 | 14.2 |
| Fluconazole | fungal lanosterol 14-alpha demethylase inhibitor | 73 | | | |
| Ketoconazole | fungal lanosterol 14-alpha demethylase inhibitor | 73 | | | |
| Miconazole | fungal lanosterol 14-alpha demethylase inhibitor | 73 | | | |
| Posaconazole | fungal lanosterol 14-alpha demethylase inhibitor | 73 | | | |
| Voriconazole | fungal lanosterol 14-alpha demethylase inhibitor | 73 | | | |
| Albendazole | fungal tubulin polymerization inhibitor | 74 | CLOUD143 | 5.7 | 28.3 |
| Prednisolone | glucocorticoid receptor agonist | 75 | CLOUD106 | 2.8 | 13.9 |
| Betamethasone | glucocorticoid receptor agonist | 75 | | | |
| Cortisone | glucocorticoid receptor agonist | 75 | | | |

Fig. 1 (cont.)

F)

| | | | | | |
|---|---|---|---|---|---|
| Dexamethasone | glucocorticoid receptor agonist | 75 | | | |
| Fludrocortisone | glucocorticoid receptor agonist | 75 | | | |
| Fluprednisolone | glucocorticoid receptor agonist | 75 | | | |
| Hydrocortisone | glucocorticoid receptor agonist | 75 | | | |
| Meprednisone | glucocorticoid receptor agonist | 75 | | | |
| Methylprednisolone | glucocorticoid receptor agonist | 75 | | | |
| Paramethasone | glucocorticoid receptor agonist | 75 | | | |
| Prednisone | glucocorticoid receptor agonist | 75 | | | |
| Eptifibatide | glycoprotein IIb-IIIa receptor inhibitor | 76 | CLOUD090 | 1.1 | 5.3 |
| Tirofiban | glycoprotein IIb-IIIa receptor inhibitor | 76 | | | |
| Isosorbide Dinitrate | guanylate cyclase activator | 77 | CLOUD007 | 0.030 | 0.10 |
| Isosorbide Mononitrate | guanylate cyclase activator | 77 | | | |
| Nitroglycerin | guanylate cyclase activator | 77 | | | |
| Oxamniquine | helminthic DNA alkylator | 78 | CLOUD289 | 7.1 | Not Tested |
| Ivermectin | helminthic glutamate-gated chloride channel activator | 79 | CLOUD280 | 0.029 | 0.14 |
| Levamisole | helminthic nicotinic acetylcholine receptor agonist | 80 | CLOUD097 | 2.4 | 11.7 |
| Mebendazole | helminthic tubulin polymerization inhibitor | 81 | CLOUD087 | 0.34 | 1.7 |
| Amodiaquine | histamine N-methyltransferase inhibitor | 82 | CLOUD015 | 0.14 | 0.70 |
| Azatadine | histamine receptor antagonist | 83 | CLOUD010 | 0.090 | 0.40 |
| Nizatidine | histamine receptor antagonist | 83 | CLOUD118 | 1.5 | 7.5 |
| Dexchlorpheniramine | histamine receptor antagonist | 83 | CLOUD204 | 0.030 | 0.13 |
| Acrivastine | histamine receptor antagonist | 83 | | | |
| Bromodiphenhydramine | histamine receptor antagonist | 83 | | | |
| Brompheniramine | histamine receptor antagonist | 83 | | | |
| Buclizine | histamine receptor antagonist | 83 | | | |
| Carbinoxamine | histamine receptor antagonist | 83 | | | |
| Cetirizine | histamine receptor antagonist | 83 | | | |
| Chlophedianol | histamine receptor antagonist | 83 | | | |
| Chlorpheniramine | histamine receptor antagonist | 83 | | | |
| Cimetidine | histamine receptor antagonist | 83 | | | |
| Clemastine | histamine receptor antagonist | 83 | | | |
| Cyclizine | histamine receptor antagonist | 83 | | | |

Fig. 1 (cont.)

F)

| | | | | | |
|---|---|---|---|---|---|
| Cyproheptadine | histamine receptor antagonist | 83 | | | |
| Desloratadine | histamine receptor antagonist | 83 | | | |
| Dexbrompheniramine | histamine receptor antagonist | 83 | | | |
| Dimenhydrinate | histamine receptor antagonist | 83 | | | |
| Diphenhydramine | histamine receptor antagonist | 83 | | | |
| Diphenylpyraline | histamine receptor antagonist | 83 | | | |
| Doxepin | histamine receptor antagonist | 83 | | | |
| Doxylamine | histamine receptor antagonist | 83 | | | |
| Famotidine | histamine receptor antagonist | 83 | | | |
| Fexofenadine | histamine receptor antagonist | 83 | | | |
| Hydroxyzine | histamine receptor antagonist | 83 | | | |
| Levocetirizine | histamine receptor antagonist | 83 | | | |
| Loratadine | histamine receptor antagonist | 83 | | | |
| Meclizine | histamine receptor antagonist | 83 | | | |
| Mepyramine | histamine receptor antagonist | 83 | | | |
| Methdilazine | histamine receptor antagonist | 83 | | | |
| Olopatadine | histamine receptor antagonist | 83 | | | |
| Promethazine | histamine receptor antagonist | 83 | | | |
| Ranitidine | histamine receptor antagonist | 83 | | | |
| Trimeprazine | histamine receptor antagonist | 83 | | | |
| Tripelennamine | histamine receptor antagonist | 83 | | | |
| Triprolidine | histamine receptor antagonist | 83 | | | |
| Vorinostat | histone deacetylase inhibitor | 84 | CLOUD112 | 1.2 | 9.8 |
| Romidepsin | histone deacetylase inhibitor | 84 | CLOUD292 | 0.70 | Not Tested |
| Cerivastatin | hydroxymethylglutaryl coenzyme A reductase inhibitor | 85 | CLOUD104 | 0.090 | 0.46 |
| Atorvastatin | hydroxymethylglutaryl coenzyme A reductase inhibitor | 85 | | | |
| Fluvastatin | hydroxymethylglutaryl coenzyme A reductase inhibitor | 85 | | | |
| Lovastatin | hydroxymethylglutaryl coenzyme A reductase inhibitor | 85 | | | |
| Pitavastatin | hydroxymethylglutaryl coenzyme A reductase inhibitor | 85 | | | |
| Pravastatin | hydroxymethylglutaryl coenzyme A reductase inhibitor | 85 | | | |
| Rosuvastatin | hydroxymethylglutaryl coenzyme A reductase inhibitor | 85 | | | |

Fig. 1 (cont.)

F)

| Simvastatin | hydroxymethylglutaryl coenzyme A reductase inhibitor | 85 | | | |
|---|---|---|---|---|---|
| Zaleplon | ionotropic GABA receptor agonist | 86 | CLOUD005 | 0.33 | 1.6 |
| Carisoprodol | ionotropic GABA receptor agonist | 86 | CLOUD188 | 115.2 | 576.3 |
| Etomidate | ionotropic GABA receptor agonist | 86 | CLOUD200 | 2.1 | 10.3 |
| Primidone | ionotropic GABA receptor agonist | 86 | CLOUD226 | 55.0 | 275.3 |
| Alprazolam | ionotropic GABA receptor agonist | 86 | | | |
| Butabarbital | ionotropic GABA receptor agonist | 86 | | | |
| Butalbital | ionotropic GABA receptor agonist | 86 | | | |
| Chlordiazepoxide | ionotropic GABA receptor agonist | 86 | | | |
| Chlormezanone | ionotropic GABA receptor agonist | 86 | | | |
| Clonazepam | ionotropic GABA receptor agonist | 86 | | | |
| Clorazepate | ionotropic GABA receptor agonist | 86 | | | |
| Diazepam | ionotropic GABA receptor agonist | 86 | | | |
| Estazolam | ionotropic GABA receptor agonist | 86 | | | |
| Eszopiclone | ionotropic GABA receptor agonist | 86 | | | |
| Flurazepam | ionotropic GABA receptor agonist | 86 | | | |
| Fospropofol | ionotropic GABA receptor agonist | 86 | | | |
| Glutethimide | ionotropic GABA receptor agonist | 86 | | | |
| Halazepam | ionotropic GABA receptor agonist | 86 | | | |
| Lorazepam | ionotropic GABA receptor agonist | 86 | | | |
| Meprobamate | ionotropic GABA receptor agonist | 86 | | | |
| Metharbital | ionotropic GABA receptor agonist | 86 | | | |
| Methohexital | ionotropic GABA receptor agonist | 86 | | | |
| Methyprylon | ionotropic GABA receptor agonist | 86 | | | |

Fig. 1 (cont.)

F)

| | | | | | |
|---|---|---|---|---|---|
| Midazolam | ionotropic GABA receptor agonist | 86 | | | |
| Oxazepam | ionotropic GABA receptor agonist | 86 | | | |
| Pentobarbital | ionotropic GABA receptor agonist | 86 | | | |
| Prazepam | ionotropic GABA receptor agonist | 86 | | | |
| Quazepam | ionotropic GABA receptor agonist | 86 | | | |
| Secobarbital | ionotropic GABA receptor agonist | 86 | | | |
| Talbutal | ionotropic GABA receptor agonist | 86 | | | |
| Temazepam | ionotropic GABA receptor agonist | 86 | | | |
| Thiamylal | ionotropic GABA receptor agonist | 86 | | | |
| Thiopental | ionotropic GABA receptor agonist | 86 | | | |
| Triazolam | ionotropic GABA receptor agonist | 86 | | | |
| Zolpidem | ionotropic GABA receptor agonist | 86 | | | |
| Gamma Hydroxybutyric Acid | ionotropic GABA receptor agonist; metabotropic GABA receptor agonist | 87 | Controlled | | |
| Flumazenil | ionotropic GABA receptor antagonist | 88 | CLOUD045 | 0.33 | 1.6 |
| Memantine | ionotropic glutamate receptor antagonist | 89 | CLOUD032 | 0.26 | 1.3 |
| Acamprosate | ionotropic glutamate receptor antagonist | 89 | CLOUD272 | 3.6 | 10.0 |
| Desflurane | ionotropic glutamate receptor antagonist | 89 | | | |
| Enflurane | ionotropic glutamate receptor antagonist | 89 | | | |
| Halothane | ionotropic glutamate receptor antagonist | 89 | | | |
| Isoflurane | ionotropic glutamate receptor antagonist | 89 | | | |
| Ketamine | ionotropic glutamate receptor antagonist | 89 | | | |
| Methoxyflurane | ionotropic glutamate receptor antagonist | 89 | | | |
| Sevoflurane | ionotropic glutamate receptor antagonist | 89 | | | |

Fig. 1 (cont.)

F)

| | | | | | |
|---|---|---|---|---|---|
| Triclofos | ionotropic glutamate receptor antagonist | 89 | | | |
| Dextromethorphan | ionotropic glutamate receptor antagonist; sigma-1 receptor agonist | 90 | CLOUD287 | 0.15 | 0.74 |
| Zafirlukast | leukotriene receptor antagonist | 91 | CLOUD092 | 0.050 | 0.26 |
| Montelukast | leukotriene receptor antagonist | 91 | | | |
| Zileuton | leukotriene synthase inhibitor | 92 | CLOUD187 | 21.1 | 105.4 |
| Ramelteon | melatonin receptor agonist | 93 | CLOUD107 | 0.030 | 0.13 |
| Baclofen | metabotropic GABA receptor agonist | 94 | CLOUD246 | 2.8 | 14.0 |
| Piperazine Hexahydrate | metabotropic GABA receptor agonist | 94 | CLOUD254 | 1.2 | 5.8 |
| Propofol | metabotropic GABA receptor agonist | 94 | | | |
| Desoxycorticosterone Pivalate | mineralocorticoid receptor agonist | 95 | CLOUD001 | 0.14 | 0.70 |
| Spironolactone | mineralocorticoid receptor antagonist | 96 | CLOUD072 | 0.60 | 3.0 |
| Drospirenone | mineralocorticoid receptor antagonist | 96 | | | |
| Eplerenone | mineralocorticoid receptor antagonist | 96 | | | |
| Tranylcypromine | monoamine oxidase inhibitor | 97 | CLOUD020 | 1.5 | 7.5 |
| Pargyline | monoamine oxidase inhibitor | 97 | CLOUD030 | 0.38 | 1.9 |
| Isocarboxazid | monoamine oxidase inhibitor | 97 | | | |
| Phenelzine | monoamine oxidase inhibitor | 97 | | | |
| Rasagiline | monoamine oxidase inhibitor | 97 | | | |
| Selegiline | monoamine oxidase inhibitor | 97 | | | |
| Cevimeline | muscarinic acetylcholine receptor agonist | 98 | CLOUD055 | 0.30 | 1.5 |
| Bethanechol | muscarinic acetylcholine receptor agonist | 98 | | | |
| Carbachol | muscarinic acetylcholine receptor agonist; nicotinic acetylcholine receptor agonist | 99 | CLOUD012 | 0.00073 | 0.037 |
| Oxyphenonium Bromide | muscarinic acetylcholine receptor antagonist | 100 | CLOUD022 | 0.010 | 0.10 |
| Trihexyphenidyl | muscarinic acetylcholine receptor antagonist | 100 | CLOUD042 | 0.66 | 3.3 |
| Anisotropine | muscarinic acetylcholine receptor antagonist | 100 | | | |

Fig. 1 (cont.)

F)

| | | | | | |
|---|---|---|---|---|---|
| Atropine | muscarinic acetylcholine receptor antagonist | 100 | | | |
| Benztropine | muscarinic acetylcholine receptor antagonist | 100 | | | |
| Biperiden | muscarinic acetylcholine receptor antagonist | 100 | | | |
| Clidinium | muscarinic acetylcholine receptor antagonist | 100 | | | |
| Cycrimine | muscarinic acetylcholine receptor antagonist | 100 | | | |
| Darifenacin | muscarinic acetylcholine receptor antagonist | 100 | | | |
| Dicyclomine | muscarinic acetylcholine receptor antagonist | 100 | | | |
| Diphemanil | muscarinic acetylcholine receptor antagonist | 100 | | | |
| Ethopropazine | muscarinic acetylcholine receptor antagonist | 100 | | | |
| Fesoterodine | muscarinic acetylcholine receptor antagonist | 100 | | | |
| Glycopyrrolate | muscarinic acetylcholine receptor antagonist | 100 | | | |
| Hexocyclium | muscarinic acetylcholine receptor antagonist | 100 | | | |
| Isopropamide | muscarinic acetylcholine receptor antagonist | 100 | | | |
| Mepenzolate | muscarinic acetylcholine receptor antagonist | 100 | | | |
| Methantheline | muscarinic acetylcholine receptor antagonist | 100 | | | |
| Methylscopolamine | muscarinic acetylcholine receptor antagonist | 100 | | | |
| Metixene | muscarinic acetylcholine receptor antagonist | 100 | | | |
| Orphenadrine | muscarinic acetylcholine receptor antagonist | 100 | | | |
| Oxybutynin | muscarinic acetylcholine receptor antagonist | 100 | | | |
| Oxyphencyclimine | muscarinic acetylcholine receptor antagonist | 100 | | | |
| Procyclidine | muscarinic acetylcholine receptor antagonist | 100 | | | |

Fig. 1 (cont.)

F)

| | | | | | |
|---|---|---|---|---|---|
| Propantheline | muscarinic acetylcholine receptor antagonist | 100 | | | |
| Scopolamine | muscarinic acetylcholine receptor antagonist | 100 | | | |
| Solifenacin | muscarinic acetylcholine receptor antagonist | 100 | | | |
| Tiotropium | muscarinic acetylcholine receptor antagonist | 100 | | | |
| Tolterodine | muscarinic acetylcholine receptor antagonist | 100 | | | |
| Tridihexethyl | muscarinic acetylcholine receptor antagonist | 100 | | | |
| Trospium | muscarinic acetylcholine receptor antagonist | 100 | | | |
| Aprepitant | neurokinin receptor antagonist | 101 | CLOUD264 | 4.1 | 20.6 |
| Varenicline | nicotinic acetylcholine receptor agonist | 102 | CLOUD267 | 0.047 | 0.24 |
| Decamethonium | nicotinic acetylcholine receptor agonist | 102 | | | |
| Nicotine | nicotinic acetylcholine receptor agonist | 102 | | | |
| Vecuronium Bromide | nicotinic acetylcholine receptor antagonist | 103 | CLOUD039 | 0.66 | 3.3 |
| Mecamylamine | nicotinic acetylcholine receptor antagonist | 103 | CLOUD098 | 0.71 | 3.6 |
| Cisatracurium Besylate | nicotinic acetylcholine receptor antagonist | 103 | CLOUD137 | 3.6 | 18.1 |
| Succinylcholine Chloride | nicotinic acetylcholine receptor antagonist | 103 | CLOUD261 | 2.5 | 12.6 |
| Pentolinium Tartrate | nicotinic acetylcholine receptor antagonist | 103 | CLOUD285 | 6.2 | 6.2 |
| Atracurium | nicotinic acetylcholine receptor antagonist | 103 | | | |
| Doxacurium | nicotinic acetylcholine receptor antagonist | 103 | | | |
| Gallamine | nicotinic acetylcholine receptor antagonist | 103 | | | |
| Metocurine | nicotinic acetylcholine receptor antagonist | 103 | | | |
| Mivacurium | nicotinic acetylcholine receptor antagonist | 103 | | | |
| Pancuronium | nicotinic acetylcholine receptor antagonist | 103 | | | |

Fig. 1 (cont.)

F)

| Pipecuronium | nicotinic acetylcholine receptor antagonist | 103 | | | |
|---|---|---|---|---|---|
| Rapacuronium | nicotinic acetylcholine receptor antagonist | 103 | | | |
| Rocuronium | nicotinic acetylcholine receptor antagonist | 103 | | | |
| Trimethaphan | nicotinic acetylcholine receptor antagonist | 103 | | | |
| Tubocurarine | nicotinic acetylcholine receptor antagonist | 103 | | | |
| Metformin | non-specific serine-threonine protein kinase activator | 104 | CLOUD148 | 7.7 | 38.7 |
| Everolimus | non-specific serine-threonine protein kinase inhibitor | 105 | CLOUD196 | 0.19 | 0.95 |
| Sirolimus | non-specific serine-threonine protein kinase inhibitor | 105 | | | |
| Temsirolimus | non-specific serine-threonine protein kinase inhibitor | 105 | | | |
| Maprotiline | norepinephrine transporter inhibitor | 106 | CLOUD006 | 2.2 | 10.8 |
| Imipramine | norepinephrine transporter inhibitor | 106 | CLOUD044 | 1.3 | 6.2 |
| Amoxapine | norepinephrine transporter inhibitor | 106 | CLOUD109 | 1.9 | 9.6 |
| Atomoxetine | norepinephrine transporter inhibitor | 106 | | | |
| Desipramine | norepinephrine transporter inhibitor | 106 | | | |
| Mazindol | norepinephrine transporter inhibitor | 106 | | | |
| Nortriptyline | norepinephrine transporter inhibitor | 106 | | | |
| Protriptyline | norepinephrine transporter inhibitor | 106 | | | |
| Trimipramine | norepinephrine transporter inhibitor | 106 | | | |
| Amitriptyline | norepinephrine transporter inhibitor | 106 | | | |
| Guanadrel | norepinephrine transporter substrate | 107 | CLOUD266 | 28.1 | 140.7 |
| Diethylpropion | norepinephrine transporter substrate | 107 | | | |
| Guanethidine | norepinephrine transporter substrate | 107 | | | |
| Phentermine | norepinephrine transporter substrate | 107 | | | |

Fig. 1 (cont.)

F)

| | | | | | |
|---|---|---|---|---|---|
| Phendimetrazine | norepinephrine transporter substrate; dopamine transporter substrate | 108 | Controlled | | |
| Loperamide | opioid receptor agonist | 109 | CLOUD058 | 0.010 | 0.032 |
| Alfentanil | opioid receptor agonist | 109 | | | |
| Anileridine | opioid receptor agonist | 109 | | | |
| Butorphanol | opioid receptor agonist | 109 | | | |
| Codeine | opioid receptor agonist | 109 | | | |
| Difenoxin | opioid receptor agonist | 109 | | | |
| Dihydrocodeine | opioid receptor agonist | 109 | | | |
| Diphenoxylate | opioid receptor agonist | 109 | | | |
| Fentanyl | opioid receptor agonist | 109 | | | |
| Hydrocodone | opioid receptor agonist | 109 | | | |
| Hydromorphone | opioid receptor agonist | 109 | | | |
| Levomethadyl | opioid receptor agonist | 109 | | | |
| Levorphanol | opioid receptor agonist | 109 | | | |
| Meperidine | opioid receptor agonist | 109 | | | |
| Methadone | opioid receptor agonist | 109 | | | |
| Morphine | opioid receptor agonist | 109 | | | |
| Oxycodone | opioid receptor agonist | 109 | | | |
| Oxymorphone | opioid receptor agonist | 109 | | | |
| Propoxyphene | opioid receptor agonist | 109 | | | |
| Remifentanil | opioid receptor agonist | 109 | | | |
| Sufentanil | opioid receptor agonist | 109 | | | |
| Tramadol | opioid receptor agonist | 109 | | | |
| Tapentadol | opioid receptor agonist; norepinephrine transporter inhibitor | 110 | Controlled | | |
| Buprenorphine | opioid receptor agonist; opioid receptor antagonist | 111 | Controlled | | |
| Dezocine | opioid receptor agonist; opioid receptor antagonist | 111 | Controlled | | |
| Nalbuphine | opioid receptor agonist; opioid receptor antagonist | 111 | Controlled | | |
| Nalmefene | opioid receptor agonist; opioid receptor antagonist | 111 | Controlled | | |
| Pentazocine | opioid receptor agonist; opioid receptor antagonist | 111 | Controlled | | |
| Naltrexone | opioid receptor antagonist | 112 | CLOUD038 | 0.090 | 0.40 |
| Alvimopan | opioid receptor antagonist | 112 | | | |
| Levallorphan | opioid receptor antagonist | 112 | | | |
| Methylnaltrexone | opioid receptor antagonist | 112 | | | |
| Naloxone | opioid receptor antagonist | 112 | | | |

Fig. 1 (cont.)

F)

| | | | | | |
|---|---|---|---|---|---|
| (+/-)-Sulfinpyrazone | organic anion transporter inhibitor | 113 | CLOUD229 | 42.0 | 210.1 |
| Probenecid | organic anion transporter inhibitor | 113 | CLOUD244 | 700.9 | 3504.3 |
| Pamidronic Acid | osteoclastic proton pump inhibitor; protein-tyrosine phosphatase inhibitor | 114 | CLOUD276 | 4.3 | 21.3 |
| Alendronate | osteoclastic proton pump inhibitor; protein-tyrosine phosphatase inhibitor | 114 | | | |
| Etidronic Acid | osteoclastic proton pump inhibitor; protein-tyrosine phosphatase inhibitor | 114 | | | |
| Ibandronate | osteoclastic proton pump inhibitor; protein-tyrosine phosphatase inhibitor | 114 | | | |
| Risedronate | osteoclastic proton pump inhibitor; protein-tyrosine phosphatase inhibitor | 114 | | | |
| Tiludronate | osteoclastic proton pump inhibitor; protein-tyrosine phosphatase inhibitor | 114 | | | |
| Zoledronate | osteoclastic proton pump inhibitor; protein-tyrosine phosphatase inhibitor | 114 | | | |
| Orlistat | pancreatic lipase inhibitor | 115 | CLOUD278 | 0.010 | 0.091 |
| Rosiglitazone | peroxisome proliferator-activated receptor agonist | 116 | CLOUD016 | 0.84 | 4.2 |
| Clofibrate | peroxisome proliferator-activated receptor agonist | 116 | CLOUD247 | 325.5 | 325.5 |
| Fenofibrate | peroxisome proliferator-activated receptor agonist | 116 | | | |
| Gemfibrozil | peroxisome proliferator-activated receptor agonist | 116 | | | |
| Pioglitazone | peroxisome proliferator-activated receptor agonist | 116 | | | |
| Troglitazone | peroxisome proliferator-activated receptor agonist | 116 | | | |
| Sildenafil | phosphodiesterase inhibitor | 117 | CLOUD073 | 0.11 | 0.50 |
| Milrinone | phosphodiesterase inhibitor | 117 | CLOUD079 | 1.2 | 5.9 |
| Dipyridamole | phosphodiesterase inhibitor | 117 | CLOUD122 | 4.0 | 19.8 |
| Anagrelide | phosphodiesterase inhibitor | 117 | | | |
| Cilostazol | phosphodiesterase inhibitor | 117 | | | |
| Dyphylline | phosphodiesterase inhibitor | 117 | | | |
| Inamrinone | phosphodiesterase inhibitor | 117 | | | |
| Pentoxifylline | phosphodiesterase inhibitor | 117 | | | |
| Tadalafil | phosphodiesterase inhibitor | 117 | | | |

Fig. 1 (cont.)

F)

| | | | | | |
|---|---|---|---|---|---|
| Vardenafil | phosphodiesterase inhibitor | 117 | | | |
| Caffeine | phosphodiesterase inhibitor; adenosine receptor antagonist | 118 | CLOUD295 | 51.5 | Not Tested |
| Tranexamic Acid | plasminogen inhibitor | 119 | CLOUD253 | 318.0 | 8.0 |
| Lansoprazole | potassium transporting ATPase inhibitor | 120 | CLOUD141 | 4.6 | 11.1 |
| Dexlansoprazole | potassium transporting ATPase inhibitor | 120 | | | |
| Esomeprazole | potassium transporting ATPase inhibitor | 120 | | | |
| Omeprazole | potassium transporting ATPase inhibitor | 120 | | | |
| Pantoprazole | potassium transporting ATPase inhibitor | 120 | | | |
| Rabeprazole | potassium transporting ATPase inhibitor | 120 | | | |
| Levonorgestrel | progesterone receptor agonist | 121 | CLOUD043 | 0.050 | 0.20 |
| Desogestrel | progesterone receptor agonist | 121 | | | |
| Dienogest | progesterone receptor agonist | 121 | | | |
| Dydrogesterone | progesterone receptor agonist | 121 | | | |
| Ethynodiol | progesterone receptor agonist | 121 | | | |
| Etonogestrel | progesterone receptor agonist | 121 | | | |
| Hydroxyprogesterone | progesterone receptor agonist | 121 | | | |
| Medroxyprogesterone | progesterone receptor agonist | 121 | | | |
| Megestrol | progesterone receptor agonist | 121 | | | |
| Norelgestromin | progesterone receptor agonist | 121 | | | |
| Norethindrone | progesterone receptor agonist | 121 | | | |
| Norethynodrel | progesterone receptor agonist | 121 | | | |
| Norgestimate | progesterone receptor agonist | 121 | | | |
| Progesterone | progesterone receptor agonist | 121 | | | |
| Ulipristal Acetate | progesterone receptor agonist; progesterone receptor antagonist | 122 | CLOUD027 | 0.78 | 3.9 |
| Mifepristone | progesterone receptor antagonist; glucocorticoid receptor agonist | 123 | CLOUD296 | 4.6 | Not Tested |
| Hydralazine | prolyl hydroxylase inhibitor | 124 | CLOUD105 | 3.1 | 15.6 |
| Iloprost | prostaglandin receptor agonist | 125 | CLOUD147 | 0.00021 | 0.0010 |
| Dinoprostone | prostaglandin receptor agonist | 125 | CLOUD270 | 0.00014 | Not Tested |
| Alprostadil | prostaglandin receptor agonist | 125 | | | |

Fig. 1 (cont.)

F)

| | | | | | |
|---|---|---|---|---|---|
| Carboprost | prostaglandin receptor agonist | 125 | | | |
| Epoprostenol | prostaglandin receptor agonist | 125 | | | |
| Misoprostol | prostaglandin receptor agonist | 125 | | | |
| Treprostinil | prostaglandin receptor agonist | 125 | | | |
| Bortezomib | proteasome inhibitor | 126 | CLOUD024 | 0.31 | 1.6 |
| Artemether | protozoal calcium transporting ATPase inhibitor | 127 | CLOUD111 | 0.77 | 3.9 |
| Proguanil | protozoal dihydrofolate reductase inhibitor | 128 | CLOUD036 | 0.59 | 3.0 |
| Eflornithine | protozoal ornithine decarboxylase inhibitor; ornithine decarboxylase inhibitor | 129 | CLOUD207 | 319.5 | 79.9 |
| Nitazoxanide | protozoal pyruvate ferredoxin oxidoreductase substrate | 130 | CLOUD174 | 9.8 | 48.8 |
| Paromomycin | protozoal ribosome inhibitor | 131 | CLOUD197 | 66.6 | 1.6 |
| Sunitinib | receptor protein-tyrosine kinase inhibitor | 132 | CLOUD071 | 0.15 | 0.70 |
| Imatinib | receptor protein-tyrosine kinase inhibitor | 132 | CLOUD114 | 2.8 | 14.0 |
| Gefitinib | receptor protein-tyrosine kinase inhibitor | 132 | CLOUD205 | 6.9 | 10.0 |
| Sorafenib | receptor protein-tyrosine kinase inhibitor | 132 | CLOUD219 | 16.4 | 105.5 |
| Pazopanib | receptor protein-tyrosine kinase inhibitor | 132 | CLOUD234 | 132.6 | 4.4 |
| Dasatinib | receptor protein-tyrosine kinase inhibitor | 132 | | | |
| Erlotinib | receptor protein-tyrosine kinase inhibitor | 132 | | | |
| Lapatinib | receptor protein-tyrosine kinase inhibitor | 132 | | | |
| Nilotinib | receptor protein-tyrosine kinase inhibitor | 132 | | | |
| Cilastatin | renal dipeptidase inhibitor | 133 | CLOUD208 | 153.4 | 153.4 |
| Aliskiren | renin inhibitor | 134 | CLOUD002 | 0.76 | 2.5 |
| Acitretin | retinoic acid receptor agonist | 135 | CLOUD080 | 1.5 | 7.7 |
| Bexarotene | retinoic acid receptor agonist | 135 | | | |
| Etretinate | retinoic acid receptor agonist | 135 | | | |
| Isotretinoin | retinoic acid receptor agonist | 135 | | | |

Fig. 1 (cont.)

F)

| | | | | | |
|---|---|---|---|---|---|
| 6-Mercaptopurine | ribonucleoside-diphosphate reductase inhibitor | 136 | CLOUD102 | 2.0 | 9.9 |
| Hydroxyurea | ribonucleoside-diphosphate reductase inhibitor | 136 | CLOUD179 | 130.0 | 650.0 |
| Clofarabine | ribonucleoside-diphosphate reductase inhibitor | 136 | CLOUD209 | 1.5 | 7.5 |
| Cladribine | ribonucleoside-diphosphate reductase inhibitor | 136 | | | |
| Gemcitabine | ribonucleoside-diphosphate reductase inhibitor | 136 | | | |
| Nelarabine | ribonucleoside-diphosphate reductase inhibitor | 136 | | | |
| Dantrolene | ryanodine receptor antagonist | 137 | CLOUD132 | 4.8 | 23.9 |
| Sumatriptan | serotonin receptor agonist | 138 | CLOUD060 | 0.20 | 1.0 |
| Cisapride | serotonin receptor agonist | 138 | CLOUD067 | 0.17 | 0.90 |
| Buspirone | serotonin receptor agonist | 138 | CLOUD262 | 0.010 | 0.050 |
| Almotriptan | serotonin receptor agonist | 138 | | | |
| Eletriptan | serotonin receptor agonist | 138 | | | |
| Frovatriptan | serotonin receptor agonist | 138 | | | |
| Methysergide | serotonin receptor agonist | 138 | | | |
| Naratriptan | serotonin receptor agonist | 138 | | | |
| Rizatriptan | serotonin receptor agonist | 138 | | | |
| Tegaserod | serotonin receptor agonist | 138 | | | |
| Zolmitriptan | serotonin receptor agonist | 138 | | | |
| Palonosetron | serotonin receptor antagonist | 139 | CLOUD283 | 0.0082 | 10.0 |
| Alosetron | serotonin receptor antagonist | 139 | | | |
| Dolasetron | serotonin receptor antagonist | 139 | | | |
| Granisetron | serotonin receptor antagonist | 139 | | | |
| Nefazodone | serotonin receptor antagonist | 139 | | | |
| Ondansetron | serotonin receptor antagonist | 139 | | | |
| Methotrimeprazine | serotonin receptor antagonist | 139 | | | |
| Ziprasidone | serotonin receptor antagonist | 139 | | | |
| Cyclobenzaprine | serotonin receptor antagonist | 139 | | | |
| Asenapine | serotonin receptor antagonist; dopamine receptor antagonist; alpha adrenergic receptor antagonist | 140 | CLOUD013 | 0.010 | 0.10 |
| Risperidone | serotonin receptor antagonist; dopamine receptor antagonist; alpha adrenergic receptor antagonist | 140 | CLOUD068 | 0.015 | 0.10 |
| Fluvoxamine | serotonin transporter inhibitor | 141 | CLOUD033 | 0.79 | 3.9 |
| Sertraline | serotonin transporter inhibitor | 141 | CLOUD037 | 0.65 | 3.3 |
| Trazodone | serotonin transporter inhibitor | 141 | CLOUD134 | 4.3 | 21.5 |
| Citalopram | serotonin transporter inhibitor | 141 | CLOUD198 | 0.62 | 3.1 |

Fig. 1 (cont.)

F)

| Escitalopram | serotonin transporter inhibitor | 141 | | | |
|---|---|---|---|---|---|
| Fluoxetine | serotonin transporter inhibitor | 141 | | | |
| Paroxetine | serotonin transporter inhibitor | 141 | | | |
| Clomipramine | serotonin transporter inhibitor | 141 | | | |
| Desvenlafaxine | serotonin transporter inhibitor | 141 | | | |
| Duloxetine | serotonin transporter inhibitor | 141 | | | |
| Milnacipran | serotonin transporter inhibitor | 141 | | | |
| Sibutramine | serotonin transporter inhibitor | 141 | | | |
| Venlafaxine | serotonin transporter inhibitor | 141 | | | |
| Chlorphentermine | serotonin transporter substrate | 142 | Controlled | 1.29 | Not Tested |
| Tiagabine | sodium- and chloride-dependent GABA transporter inhibitor | 143 | CLOUD108 | 0.53 | 2.7 |
| Digitoxin | sodium-potassium transporting ATPase inhibitor | 144 | CLOUD077 | 0.030 | 0.20 |
| Acetyldigitoxin | sodium-potassium transporting ATPase inhibitor | 144 | | | |
| Deslanoside | sodium-potassium transporting ATPase inhibitor | 144 | | | |
| Digoxin | sodium-potassium transporting ATPase inhibitor | 144 | | | |
| Dutasteride | steroid 5-alpha reductase inhibitor | 145 | CLOUD070 | 0.0024 | 0.011 |
| Finasteride | steroid 5-alpha reductase inhibitor | 145 | | | |
| Nateglinide | sulfonylurea receptor agonist | 146 | CLOUD163 | 13.2 | 10.0 |
| Chlorpropamide | sulfonylurea receptor agonist | 146 | | | |
| Glibenclamide | sulfonylurea receptor agonist | 146 | | | |
| Glimepiride | sulfonylurea receptor agonist | 146 | | | |
| Glipizide | sulfonylurea receptor agonist | 146 | | | |
| Repaglinide | sulfonylurea receptor agonist | 146 | | | |
| Tolazamide | sulfonylurea receptor agonist | 146 | | | |
| Tolbutamide | sulfonylurea receptor agonist | 146 | | | |
| Levetiracetam | synaptic vesicle glycoprotein 2A modulator | 147 | CLOUD274 | 217.4 | 1086.9 |
| Tetrabenazine | synaptic vesicular amine transporter inhibitor | 148 | CLOUD096 | 10.0 | 10.0 |
| Reserpine | synaptic vesicular amine transporter inhibitor | 148 | | | |
| Methyclothiazide | thiazide sensitive sodium-chloride cotransporter inhibitor | 149 | CLOUD050 | 0.10 | 0.50 |

Fig. 1 (cont.)

F)

| Diazoxide | thiazide sensitive sodium-chloride cotransporter inhibitor | 149 | CLOUD180 | 86.7 | 433.5 |
|---|---|---|---|---|---|
| Bendroflumethiazide | thiazide sensitive sodium-chloride cotransporter inhibitor | 149 | | | |
| Benzthiazide | thiazide sensitive sodium-chloride cotransporter inhibitor | 149 | | | |
| Chlorothiazide | thiazide sensitive sodium-chloride cotransporter inhibitor | 149 | | | |
| Chlorthalidone | thiazide sensitive sodium-chloride cotransporter inhibitor | 149 | | | |
| Cyclothiazide | thiazide sensitive sodium-chloride cotransporter inhibitor | 149 | | | |
| Hydrochlorothiazide | thiazide sensitive sodium-chloride cotransporter inhibitor | 149 | | | |
| Hydroflumethiazide | thiazide sensitive sodium-chloride cotransporter inhibitor | 149 | | | |
| Indapamide | thiazide sensitive sodium-chloride cotransporter inhibitor | 149 | | | |
| Metolazone | thiazide sensitive sodium-chloride cotransporter inhibitor | 149 | | | |
| Polythiazide | thiazide sensitive sodium-chloride cotransporter inhibitor | 149 | | | |
| Quinethazone | thiazide sensitive sodium-chloride cotransporter inhibitor | 149 | | | |
| Trichlormethiazide | thiazide sensitive sodium-chloride cotransporter inhibitor | 149 | | | |
| Argatroban | thrombin inhibitor | 150 | CLOUD008 | 1.4 | 6.9 |
| Eltrombopag | thrombopoietin receptor agonist | 151 | CLOUD279 | 16.5 | 82.5 |
| 5-Fluorouracil | thymidylate synthase inhibitor | 152 | CLOUD031 | 0.62 | 3.1 |
| Capecitabine | thymidylate synthase inhibitor | 152 | | | |
| Floxuridine | thymidylate synthase inhibitor | 152 | | | |
| Flucytosine | thymidylate synthase inhibitor | 152 | | | |
| Liothyronine | thyroid hormone receptor agonist | 153 | CLOUD275 | 0.00003 | 0.00003 |

Fig. 1 (cont.)

F)

| | | | | | |
|---|---|---|---|---|---|
| Dextrothyroxine | thyroid hormone receptor agonist | 153 | | | |
| Levothyroxine | thyroid hormone receptor agonist | 153 | | | |
| Propylthiouracil | thyroid peroxidase inhibitor | 154 | CLOUD175 | 18.0 | 90.0 |
| Methimazole | thyroid peroxidase inhibitor | 154 | | | |
| Hydroxychloroquine | toll-like receptor antagonist | 155 | CLOUD018 | 0.30 | 1.5 |
| Mitoxantrone | topoisomerase inhibitor | 156 | CLOUD063 | 0.67 | 3.4 |
| Irinotecan | topoisomerase inhibitor | 156 | CLOUD117 | 3.4 | 16.8 |
| Etoposide | topoisomerase inhibitor | 156 | | | |
| Teniposide | topoisomerase inhibitor | 156 | | | |
| Topotecan | topoisomerase inhibitor | 156 | | | |
| Docetaxel | tubulin depolymerization inhibitor | 157 | CLOUD139 | 4.5 | 22.7 |
| Cabazitaxel | tubulin depolymerization inhibitor | 157 | | | |
| Ixabepilone | tubulin depolymerization inhibitor | 157 | | | |
| Paclitaxel | tubulin depolymerization inhibitor | 157 | | | |
| Vinblastine | tubulin polymerization inhibitor | 158 | CLOUD152 | 0.020 | 0.12 |
| Colchicine | tubulin polymerization inhibitor | 158 | | | |
| Griseofulvin | tubulin polymerization inhibitor | 158 | | | |
| Vincristine | tubulin polymerization inhibitor | 158 | | | |
| Vinorelbine | tubulin polymerization inhibitor | 158 | | | |
| Metyrosine | tyrosine 3-monooxygenase inhibitor | 159 | CLOUD202 | 71.7 | 71.7 |
| Tolvaptan | vasopressin receptor antagonist | 160 | CLOUD100 | 2.2 | 11.1 |
| Conivaptan | vasopressin receptor antagonist | 160 | | | |
| Ganciclovir | viral DNA polymerase inhibitor | 161 | CLOUD233 | 19.6 | 97.9 |
| Foscarnet | viral DNA polymerase inhibitor | 161 | CLOUD265 | 887.0 | 10.4 |
| Aciclovir | viral DNA polymerase inhibitor | 161 | | | |
| Cidofovir | viral DNA polymerase inhibitor | 161 | | | |
| Didanosine | viral DNA polymerase inhibitor | 161 | | | |
| Entecavir | viral DNA polymerase inhibitor | 161 | | | |
| Famciclovir | viral DNA polymerase inhibitor | 161 | | | |
| Lamivudine | viral DNA polymerase inhibitor | 161 | | | |
| Telbivudine | viral DNA polymerase inhibitor | 161 | | | |
| Valaciclovir | viral DNA polymerase inhibitor | 161 | | | |
| Valganciclovir | viral DNA polymerase inhibitor | 161 | | | |

Fig. 1 (cont.)

F)

| | | | | | |
|---|---|---|---|---|---|
| Zidovudine | viral DNA polymerase inhibitor | 161 | | | |
| Ribavirin | viral RNA polymerase inhibitor | 162 | CLOUD178 | 15.1 | 16.0 |
| Raltegravir | viral integrase inhibitor | 163 | CLOUD211 | 4.5 | 10.0 |
| Amantadine | viral matrix protein 2 inhibitor | 164 | CLOUD260 | 4.0 | 19.8 |
| Rimantadine | viral matrix protein 2 inhibitor | 164 | | | |
| Oseltamivir | viral neuraminidase inhibitor | 165 | CLOUD021 | 0.21 | 1.0 |
| Amprenavir | viral protease inhibitor | 166 | CLOUD172 | 15.5 | 77.6 |
| Atazanavir | viral protease inhibitor | 166 | | | |
| Darunavir | viral protease inhibitor | 166 | | | |
| Fosamprenavir | viral protease inhibitor | 166 | | | |
| Indinavir | viral protease inhibitor | 166 | | | |
| Lopinavir | viral protease inhibitor | 166 | | | |
| Nelfinavir | viral protease inhibitor | 166 | | | |
| Ritonavir | viral protease inhibitor | 166 | | | |
| Saquinavir | viral protease inhibitor | 166 | | | |
| Tipranavir | viral protease inhibitor | 166 | | | |
| Zalcitabine | viral reverse transcriptase inhibitor | 167 | CLOUD078 | 0.47 | 2.4 |
| Abacavir | viral reverse transcriptase inhibitor | 167 | CLOUD146 | 13.5 | 55.7 |
| Efavirenz | viral reverse transcriptase inhibitor | 167 | CLOUD221 | 28.8 | 28.8 |
| Adefovir | viral reverse transcriptase inhibitor | 167 | | | |
| Delavirdine | viral reverse transcriptase inhibitor | 167 | | | |
| Emtricitabine | viral reverse transcriptase inhibitor | 167 | | | |
| Etravirine | viral reverse transcriptase inhibitor | 167 | | | |
| Nevirapine | viral reverse transcriptase inhibitor | 167 | | | |
| Stavudine | viral reverse transcriptase inhibitor | 167 | | | |
| Tenofovir | viral reverse transcriptase inhibitor | 167 | | | |
| Phenprocoumon | vitamin K epoxide reductase inhibitor | 168 | CLOUD167 | 12.8 | 64.2 |
| Anisindione | vitamin K epoxide reductase inhibitor | 168 | | | |
| Dicumarol | vitamin K epoxide reductase inhibitor | 168 | | | |
| Phenindione | vitamin K epoxide reductase inhibitor | 168 | | | |
| Warfarin | vitamin K epoxide reductase inhibitor | 168 | | | |

Fig. 1 (cont.)

F)

| Nisoldipine | voltage-gated calcium channel blocker | 169 | CLOUD059 | 0.0026 | 0.013 |
|---|---|---|---|---|---|
| Gabapentin | voltage-gated calcium channel blocker | 169 | CLOUD189 | 122.6 | 122.6 |
| Trimethadione | voltage-gated calcium channel blocker | 169 | CLOUD288 | 5588.9 | Not Tested |
| Amlodipine | voltage-gated calcium channel blocker | 169 | | | |
| Bepridil | voltage-gated calcium channel blocker | 169 | | | |
| Clevidipine | voltage-gated calcium channel blocker | 169 | | | |
| Diltiazem | voltage-gated calcium channel blocker | 169 | | | |
| Ethosuximide | voltage-gated calcium channel blocker | 169 | | | |
| Felodipine | voltage-gated calcium channel blocker | 169 | | | |
| Flavoxate | voltage-gated calcium channel blocker | 169 | | | |
| Isradipine | voltage-gated calcium channel blocker | 169 | | | |
| Nicardipine | voltage-gated calcium channel blocker | 169 | | | |
| Nifedipine | voltage-gated calcium channel blocker | 169 | | | |
| Nimodipine | voltage-gated calcium channel blocker | 169 | | | |
| Paramethadione | voltage-gated calcium channel blocker | 169 | | | |
| Pregabalin | voltage-gated calcium channel blocker | 169 | | | |
| Verapamil | voltage-gated calcium channel blocker | 169 | | | |
| Lubiprostone | voltage-gated chloride channel activator | 170 | CLOUD123 | 0.00013 | 0.00064 |
| Ibutilide | voltage-gated potassium channel blocker | 171 | CLOUD035 | 0.020 | 0.080 |
| Bretylium Tosylate | voltage-gated potassium channel blocker | 171 | CLOUD140 | 9.9 | 84.1 |
| Amiodarone | voltage-gated potassium channel blocker | 171 | | | |
| Dofetilide | voltage-gated potassium channel blocker | 171 | | | |

Fig. 1 (cont.)

F)

| | | | | | |
|---|---|---|---|---|---|
| Sotalol | voltage-gated potassium channel blocker | 171 | | | |
| Dronedarone | voltage-gated potassium channel blocker; voltage-gated sodium channel blocker; voltage-gated calcium channel blocker | 172 | CLOUD049 | 0.26 | 1.3 |
| Lacosamide | voltage-gated sodium channel blocker | 173 | CLOUD145 | 49.9 | 217.8 |
| Lamotrigine | voltage-gated sodium channel blocker | 173 | CLOUD155 | 54.7 | 273.3 |
| Mephenytoin | voltage-gated sodium channel blocker | 173 | CLOUD181 | 68.7 | 343.8 |
| Benzonatate | voltage-gated sodium channel blocker | 173 | | | |
| Carbamazepine | voltage-gated sodium channel blocker | 173 | | | |
| Disopyramide | voltage-gated sodium channel blocker | 173 | | | |
| Ethotoin | voltage-gated sodium channel blocker | 173 | | | |
| Flecainide | voltage-gated sodium channel blocker | 173 | | | |
| Fosphenytoin | voltage-gated sodium channel blocker | 173 | | | |
| Indecainide | voltage-gated sodium channel blocker | 173 | | | |
| Mexiletine | voltage-gated sodium channel blocker | 173 | | | |
| Moricizine | voltage-gated sodium channel blocker | 173 | | | |
| Oxcarbazepine | voltage-gated sodium channel blocker | 173 | | | |
| Phenacemide | voltage-gated sodium channel blocker | 173 | | | |
| Phenytoin | voltage-gated sodium channel blocker | 173 | | | |
| Procainamide | voltage-gated sodium channel blocker | 173 | | | |
| Propafenone | voltage-gated sodium channel blocker | 173 | | | |
| Quinidine | voltage-gated sodium channel blocker | 173 | | | |
| Tocainide | voltage-gated sodium channel blocker | 173 | | | |

Fig. 1 (cont.)

F)

| | | | | | |
|---|---|---|---|---|---|
| Topiramate | voltage-gated sodium channel blocker; ionotropic glutamate receptor antagonist | 174 | CLOUD184 | 15.3 | 76.6 |
| Zonisamide | voltage-gated sodium channel blocker; voltage-gated calcium channel blocker | 175 | CLOUD235 | 141.4 | 141.4 |
| Allopurinol | xanthine dehydrogenase-oxidase inhibitor | 176 | CLOUD191 | 139.6 | 139.6 |
| Febuxostat | xanthine dehydrogenase-oxidase inhibitor | 176 | CLOUD215 | 35.6 | 177.9 |
| Chloroquine | Unknown | | CLOUD003 | 0.94 | 4.7 |
| Diphenidol | Unknown | | CLOUD029 | 0.52 | 2.6 |
| Pentamidine | Unknown | | CLOUD047 | 1.5 | 7.4 |
| Riluzole | Unknown | | CLOUD052 | 0.85 | 4.3 |
| Niclosamide | Unknown | | CLOUD083 | 1.1 | 5.3 |
| Diethylcarbamazine | Unknown | | CLOUD094 | 1.3 | 6.3 |
| Thalidomide | Unknown | | CLOUD121 | 3.9 | 19.4 |
| Mefloquine | Unknown | | CLOUD129 | 2.6 | 13.2 |
| Lumefantrine | Unknown | | CLOUD130 | 17.0 | 82.3 |
| Trimethobenzamide | Unknown | | CLOUD131 | 5.2 | 25.7 |
| Ranolazine | Unknown | | CLOUD149 | 14.0 | 70.2 |
| Lithium Citrate | Unknown | | CLOUD150 | 1200.0 | 5783.4 |
| Praziquantel | Unknown | | CLOUD151 | 0.64 | 3.2 |
| Metaxalone | Unknown | | CLOUD153 | 7.7 | 40.7 |
| Mesalazine | Unknown | | CLOUD168 | 7.8 | 32.6 |
| Mitotane | Unknown | | CLOUD169 | 62.5 | 312.5 |
| Thiabendazole | Unknown | | CLOUD173 | 89.4 | 447.3 |
| Chlorphenesin | Unknown | | CLOUD183 | 83.9 | 444.2 |
| 4-Aminosalicylic Acid | Unknown | | CLOUD194 | 130.6 | 130.6 |
| Halofantrine | Unknown | | CLOUD199 | 12.8 | 63.9 |
| Chlorzoxazone | Unknown | | CLOUD213 | 214.1 | 899.3 |
| Rufinamide | Unknown | | CLOUD217 | 202.1 | 50.5 |
| Mebutamate | Unknown | | CLOUD228 | 28.8 | 144.2 |
| Quinine | Unknown | | CLOUD232 | 21.6 | 107.9 |
| Glatiramer Acetate | Unknown | | CLOUD236 | 10.0 | 50.0 |
| Tinidazole | Unknown | | CLOUD238 | 192.9 | 192.9 |
| Felbamate | Unknown | | CLOUD239 | 205.7 | 205.7 |
| Auranofin | Unknown | | CLOUD255 | 1.5 | 7.3 |
| Phensuximide | Unknown | | CLOUD263 | 52.9 | 264.3 |
| Pyrvinium Chloride Dihydrate | Unknown | | CLOUD271 | 10.0 | 10.0 |
| Benzquinamide | Unknown | | CLOUD290 | Unavailable | Not Tested |
| Piperacetazine | Unknown | | CLOUD291 | Unavailable | Not Tested |
| Ethchlorvynol | Unknown | | Unavailable | | |

Fig. 1 (cont.)

F)

| Ethinamate | Unknown | | Unavailable | | |
|---|---|---|---|---|---|
| Pemoline | Unknown | | Unavailable | | |

Fig. 1 (cont.)

G)

| PRODRUG NAME | PRODRUG CLOUD ID | ACTIVE FORM NAME | ACTIVE FORM CLOUD ID | PLASMA [µM] | SCREEN [µM] |
|---|---|---|---|---|---|
| Cisapride | CLOUD067 | Norcisapride | CLOUD014 | 0.080 | 0.30 |
| Olmesartan Medoxomil | CLOUD093 | Olmesartan | CLOUD028 | 2.0 | 10.1 |
| Furazolidone | CLOUD135 | 3-Amino-2-Oxazolidinone | CLOUD034 | 9.8 | 49.0 |
| Spironolactone | CLOUD072 | Canrenone | CLOUD048 | 0.73 | 3.0 |
| Tamoxifen | CLOUD064 | Endoxifen | CLOUD101 | 1.4 | 6.8 |
| Artemether | CLOUD111 | Dihydroartemisinin | CLOUD103 | 2.6 | 10.4 |
| Nitazoxanide | CLOUD174 | Tizoxanide | CLOUD120 | 9.8 | 48.8 |
| Minoxidil | CLOUD040 | Minoxidil Sulfate | CLOUD127 | 0.86 | 4.3 |
| Proguanil | CLOUD036 | Cycloguanil | CLOUD128 | 0.59 | 3.4 |
| Flutamide | CLOUD142 | Hydroxyflutamide | CLOUD136 | 5.4 | 27.1 |
| Ezetimibe | CLOUD066 | Ezetimibe Glucuronide | CLOUD154 | 0.010 | 0.047 |
| Ribavirin | CLOUD178 | Ribavirin 5'-Triphosphate | CLOUD176 | 6.6 | 33.0 |
| Leflunomide | CLOUD243 | Teriflunomide | CLOUD203 | 66.6 | 66.9 |
| Metronidazole | CLOUD170 | Hydroxymetronidazole | CLOUD210 | 58.4 | 58.4 |
| Clofibrate | CLOUD247 | Clofibric Acid | CLOUD212 | 368.0 | 1840.1 |
| Oseltamivir | CLOUD021 | Oseltamivir Acid | CLOUD220 | 2.3 | 10.0 |
| Irinotecan | CLOUD117 | 7-Ethyl-10-Hydroxy-Camptothecin | CLOUD237 | 5.0 | 25.1 |
| Pyrazinamide | CLOUD245 | Pyrazinoic Acid | CLOUD248 | 604.4 | 604.2 |
| Buspirone | CLOUD262 | 6-Hydroxybuspirone | CLOUD257 | 0.010 | 0.050 |
| Disulfiram | CLOUD062 | Sodium Diethyldithiocarbamate Trihydrate | CLOUD259 | 2.7 | 13.2 |
| Amodiaquine | CLOUD015 | Desethylamodiaquine | CLOUD268 | 0.15 | Not Tested |
| Zalcitabine | CLOUD078 | Dideoxycytidine 5'-Triphosphate | CLOUD269 | 0.22 | 2.4 |
| Clofarabine | CLOUD209 | Clofarabine Triphosphate | CLOUD282 | 3.0 | 10.0 |
| Isosorbide Dinitrate | CLOUD007 | Nitrosoglutathione | CLOUD284 | 0.021 | 1.5 |
| Cytarabine | CLOUD057 | Cytosine Arabinoside Triphosphate | CLOUD294 | 10 | Not Tested |
| Abacavir | CLOUD146 | (-)-Carbovir Triphosphate | Unavailable | | |

Fig. 1 (cont.)

G)

| | | | | | |
|---|---|---|---|---|---|
| Azacitidine | CLOUD115 | Azacitidine Triphosphate | Unavailable | | |
| Thiotepa | CLOUD277 | Aziridine | Unavailable | | |
| Clopidogrel | CLOUD019 | Clopidogrel Acid | Unavailable | | |
| Dextromethorphan | CLOUD287 | Dextrorphan | Unavailable | | |
| Acetohexamide | CLOUD240 | Hydroxyhexamide | Unavailable | | |
| Trazodone | CLOUD134 | m-Chlorophenylpiperazine | Unavailable | | |
| Altretamine | CLOUD182 | N-(Hydroxymethyl)Melamine | Unavailable | | |
| Oxamniquine | CLOUD289 | Oxamniquine Sulfate Ester | Unavailable | | |
| Romidepsin | CLOUD292 | Romidepsin Reduced | Unavailable | | |

Fig. 2
A)
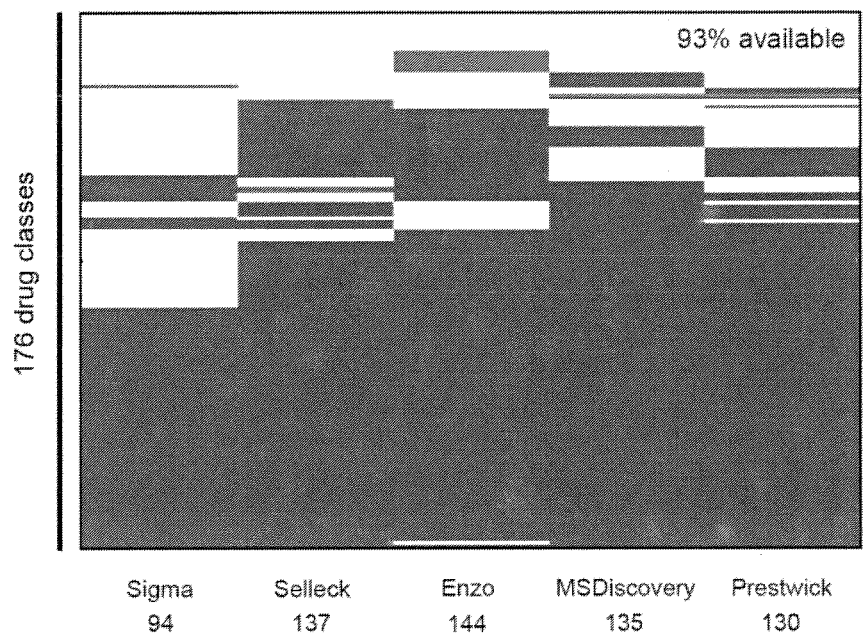
B)
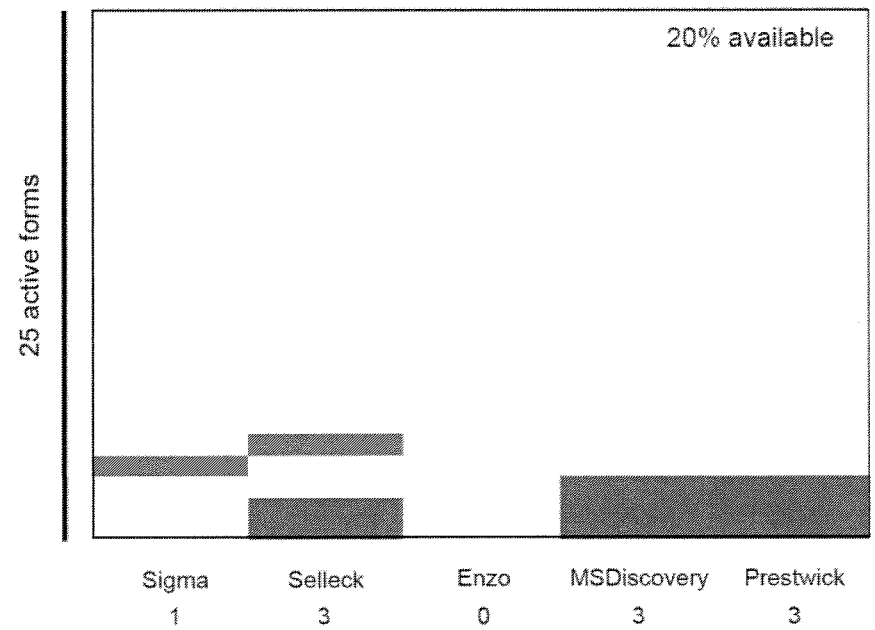

Fig. 3
A)
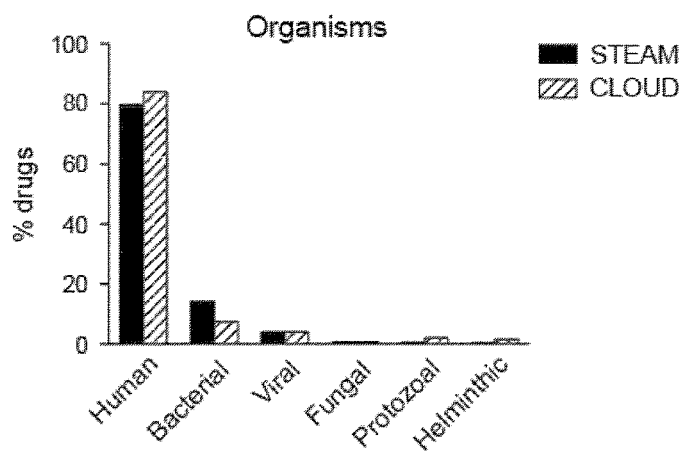
B)
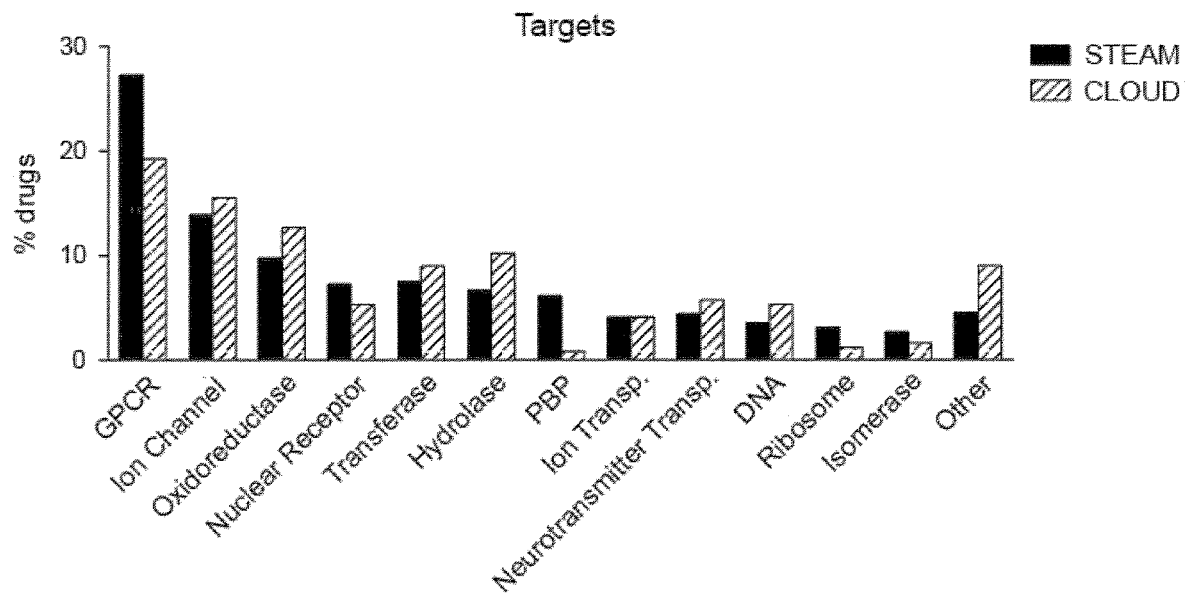

Fig. 5
A)
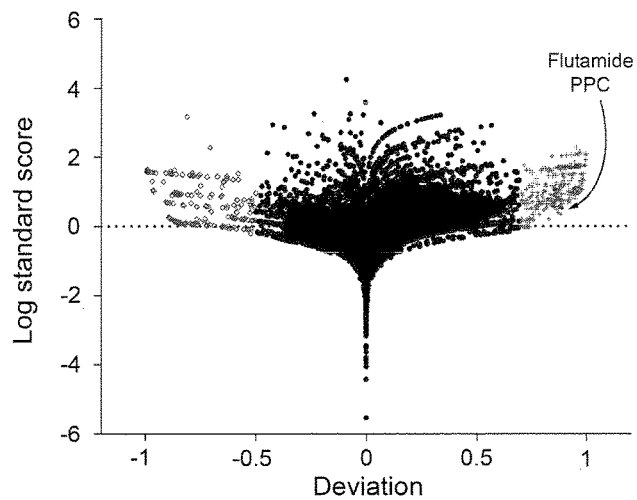
B)
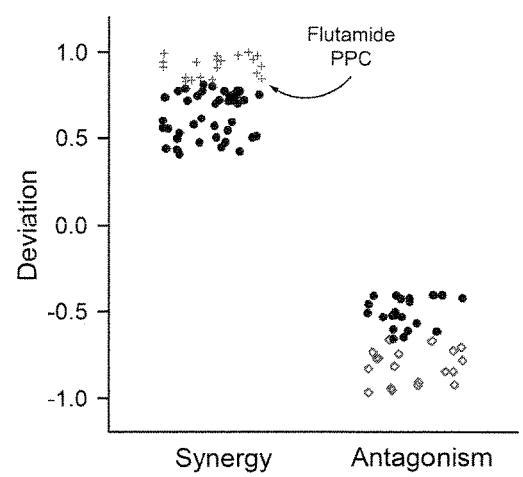
C)
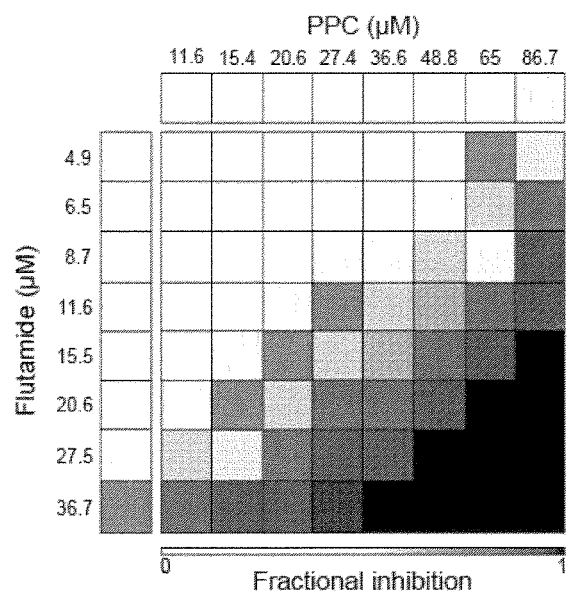
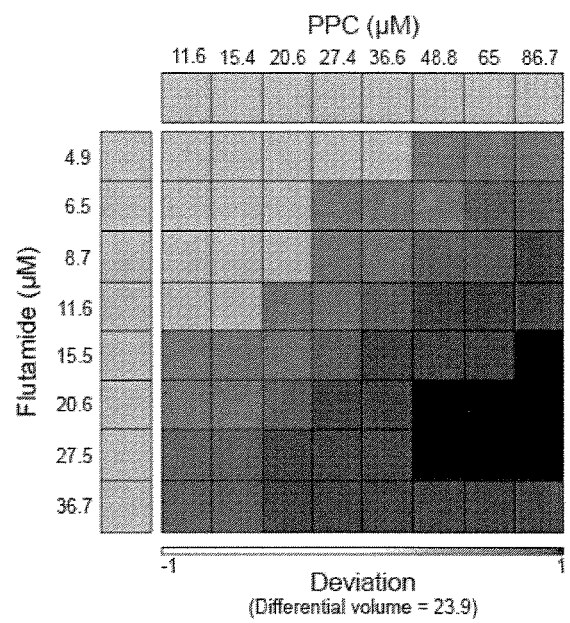

Fig. 5 (cont.)
D)
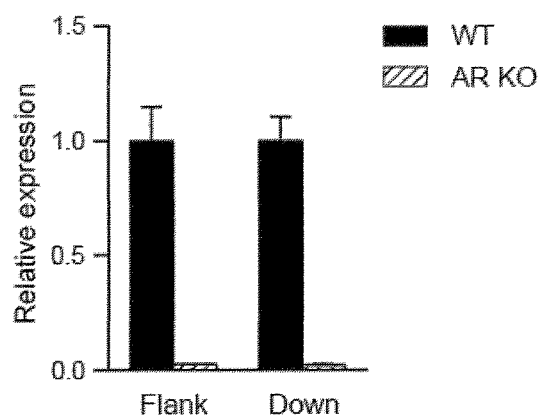
E)
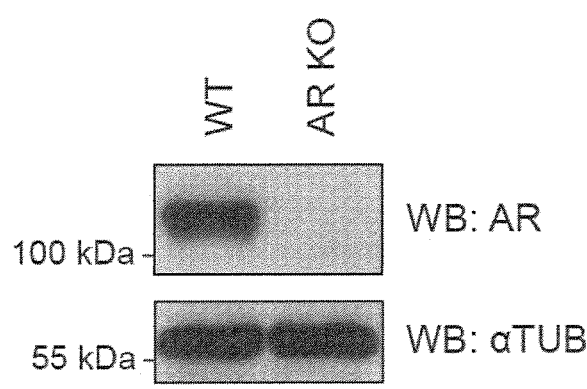
F)
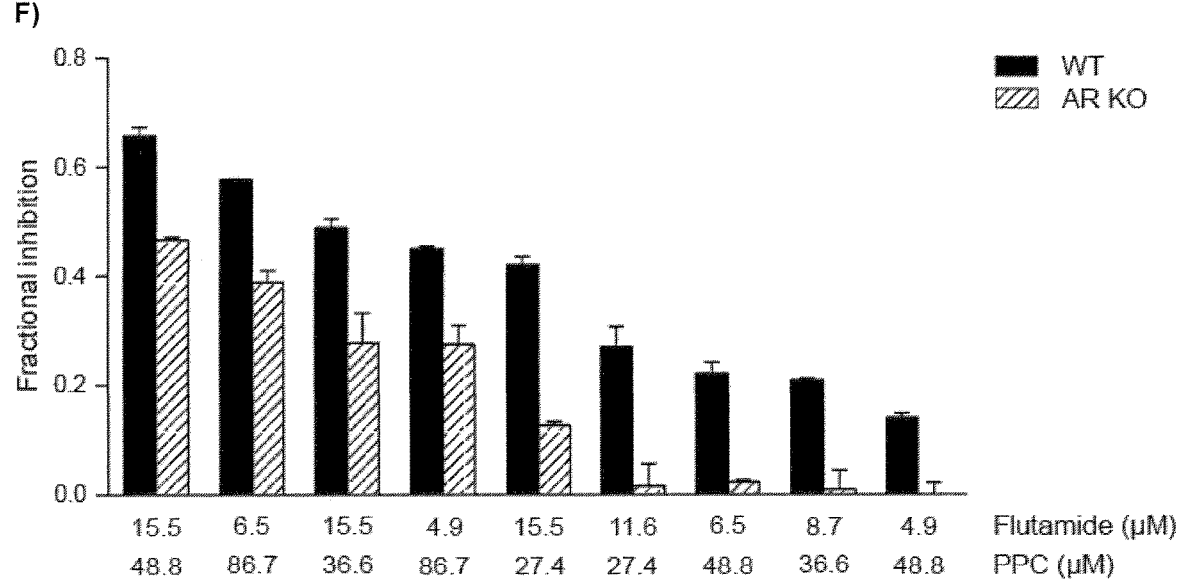

Fig. 6

| CLOUD IDs | Drug Names | Deviation |
|---|---|---|
| CLOUD039, CLOUD136 | Vecuronium Bromide, Hydroxyflutamide | 1 |
| CLOUD014, CLOUD176 | Norcisapride, Ribavirin 5'-Triphosphate | 0.995912687 |
| CLOUD054, CLOUD195 | Triamterene, Trilostane | 0.985785511 |
| CLOUD214, CLOUD224 | Sulbactam, Probucol | 0.981322192 |
| CLOUD130, CLOUD162 | Lumefantrine, Carglumic Acid | 0.980507133 |
| CLOUD214, CLOUD154 | Sulbactam, Ezetimibe Glucuronide | 0.958560109 |
| CLOUD084, CLOUD123 | Aripiprazole, Lubiprostone | 0.958377114 |
| CLOUD237, CLOUD217 | 7-Ethyl-10-Hydroxy-Camptothecin, Rufinamide | 0.951243909 |
| CLOUD051, CLOUD130 | Testosterone, Lumefantrine | 0.945625479 |
| CLOUD035, CLOUD244 | Ibutilide, Probenecid | 0.942451961 |
| CLOUD287, CLOUD035 | Dextromethorphan, Ibutilide | 0.918739023 |
| CLOUD278, CLOUD023 | Orlistat, Dopamine | 0.917548529 |
| CLOUD287, CLOUD153 | Dextromethorphan, Metaxalone | 0.912380773 |
| CLOUD285, CLOUD227 | Pentolinium Tartrate, Acetohydroxamic Acid | 0.881143836 |
| CLOUD287, CLOUD037 | Dextromethorphan, Sertraline | 0.857435409 |
| CLOUD280, CLOUD082 | Ivermectin, Isoproterenol | 0.856788814 |
| CLOUD167, CLOUD142 | Phenprocoumon, Flutamide | 0.849005958 |
| CLOUD285, CLOUD229 | Pentolinium Tartrate, (+/-)-Sulfinpyrazone | 0.845810578 |
| CLOUD286, CLOUD082 | Nabilone, Isoproterenol | 0.839761824 |
| CLOUD272, CLOUD164 | Acamprosate, Temozolomide | 0.832155715 |
| CLOUD175, CLOUD259 | Propylthiouracil, Sodium Diethyldithiocarbamate Trihydrate | -0.658897198 |
| CLOUD071, CLOUD165 | Sunitinib, Mycophenolic Acid | -0.669775256 |
| CLOUD054, CLOUD174 | Triamterene, Nitazoxanide | -0.703148114 |
| CLOUD114, CLOUD235 | Imatinib, Zonisamide | -0.722769812 |
| CLOUD006, CLOUD114 | Maprotiline, Imatinib | -0.730463871 |
| CLOUD165, CLOUD183 | Mycophenolic Acid, Chlorphenesin | -0.741019759 |
| CLOUD247, CLOUD062 | Clofibrate, Disulfiram | -0.766918525 |
| CLOUD041, CLOUD139 | Busulfan, Docetaxel | -0.767767513 |
| CLOUD114, CLOUD229 | Imatinib, (+/-)-Sulfinpyrazone | -0.769152987 |
| CLOUD114, CLOUD241 | Imatinib, Dichlorphenamide | -0.779417168 |
| CLOUD053, CLOUD252 | Doxorubicin, Fosfomycin | -0.812327477 |
| CLOUD013, CLOUD114 | Asenapine, Imatinib | -0.826735938 |
| CLOUD012, CLOUD114 | Carbachol, Imatinib | -0.84301566 |
| CLOUD114, CLOUD231 | Imatinib, Novobiocin | -0.843243104 |
| CLOUD133, CLOUD238 | Epinephrine, Tinidazole | -0.904028167 |
| CLOUD112, CLOUD066 | Vorinostat, Ezetimibe | -0.918948331 |
| CLOUD246, CLOUD165 | Baclofen, Mycophenolic Acid | -0.923029586 |
| CLOUD133, CLOUD235 | Epinephrine, Zonisamide | -0.938159734 |
| CLOUD211, CLOUD165 | Raltegravir, Mycophenolic Acid | -0.951892852 |
| CLOUD216, CLOUD259 | Cefmenoxime, Sodium Diethyldithiocarbamate Trihydrate | -0.962208076 |

Fig. 7
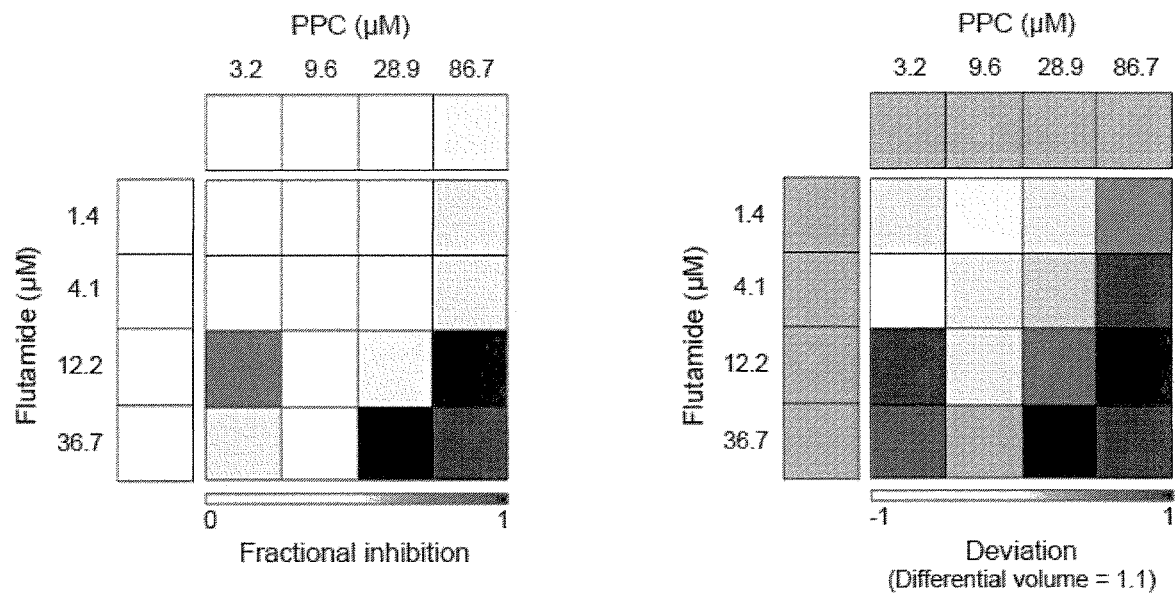
Fig. 8
A)
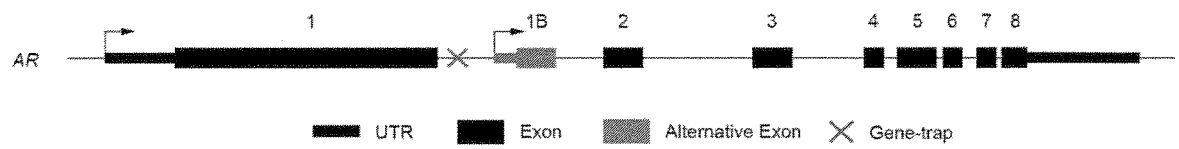
B)
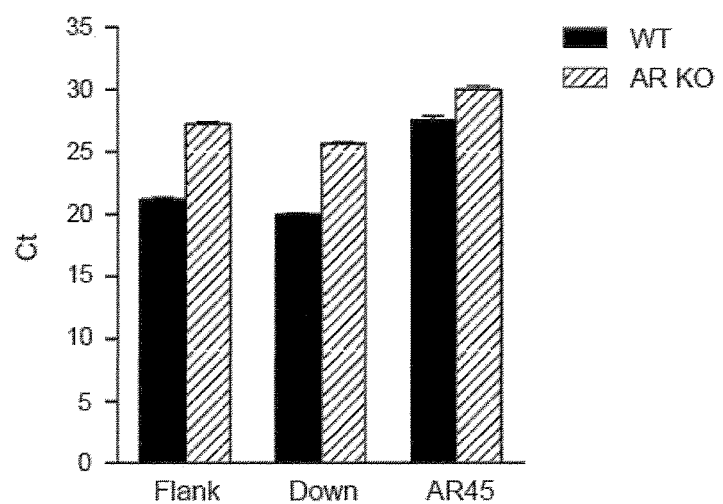

Fig. 9
A)
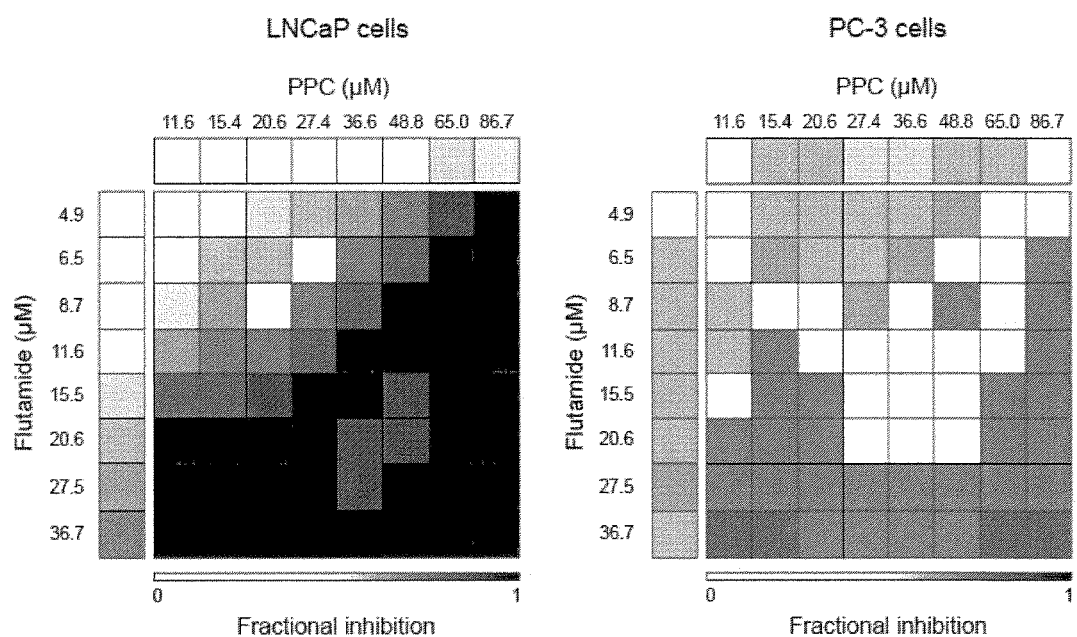
B)
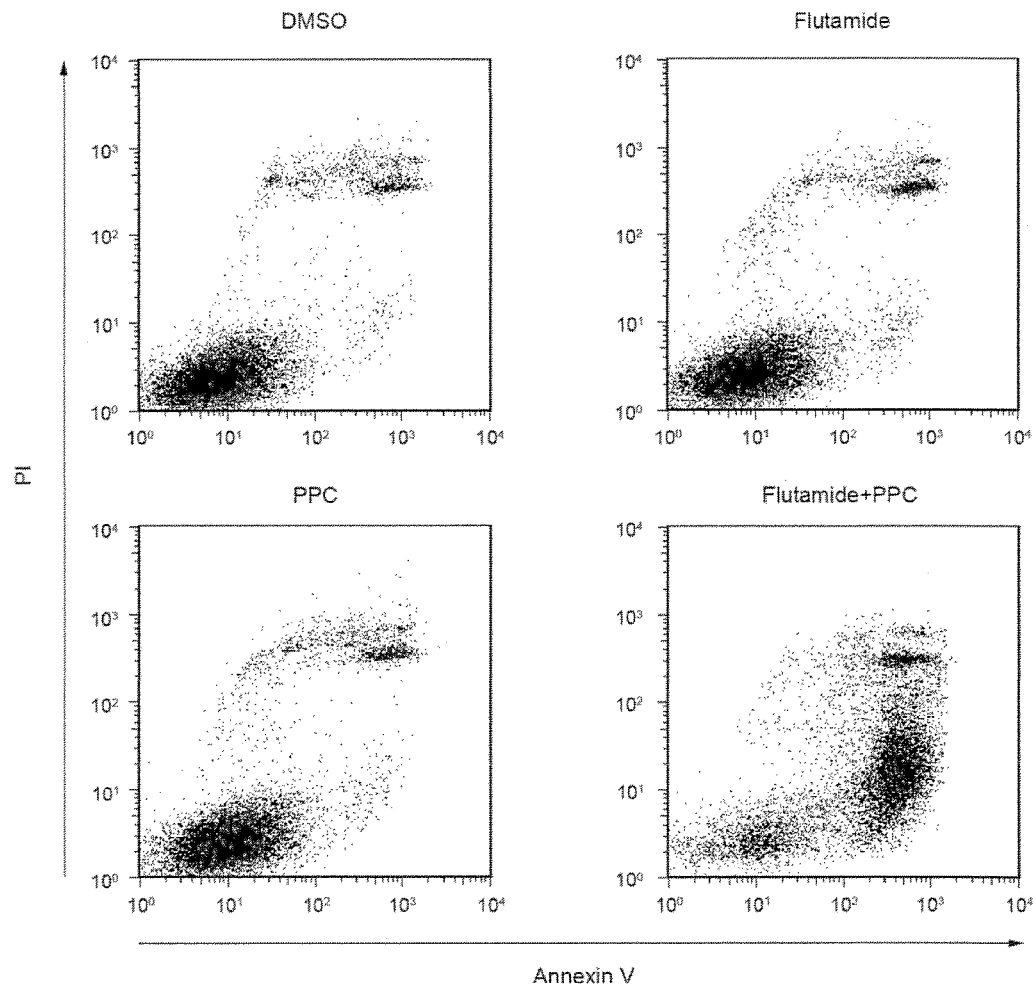

A)

B)

Figure 13:
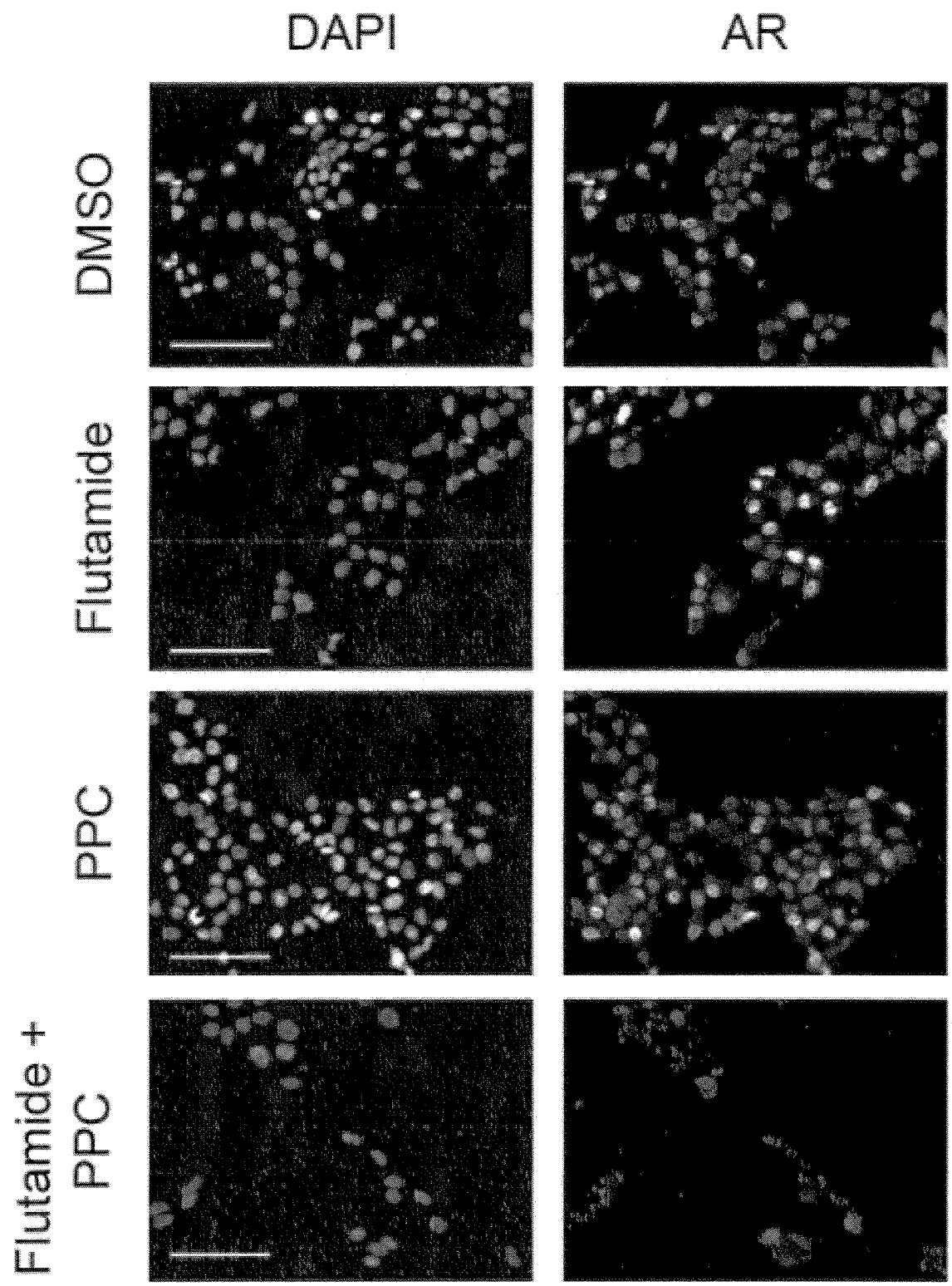
Figure 13:
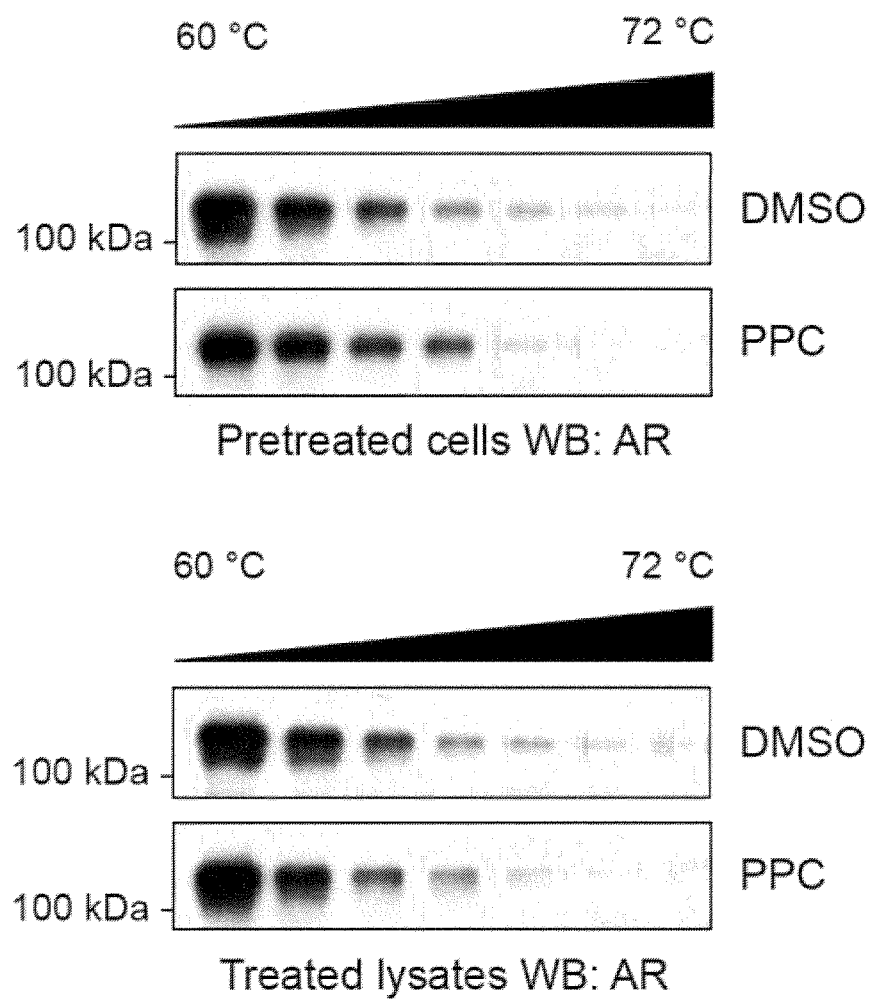
Figure 13:
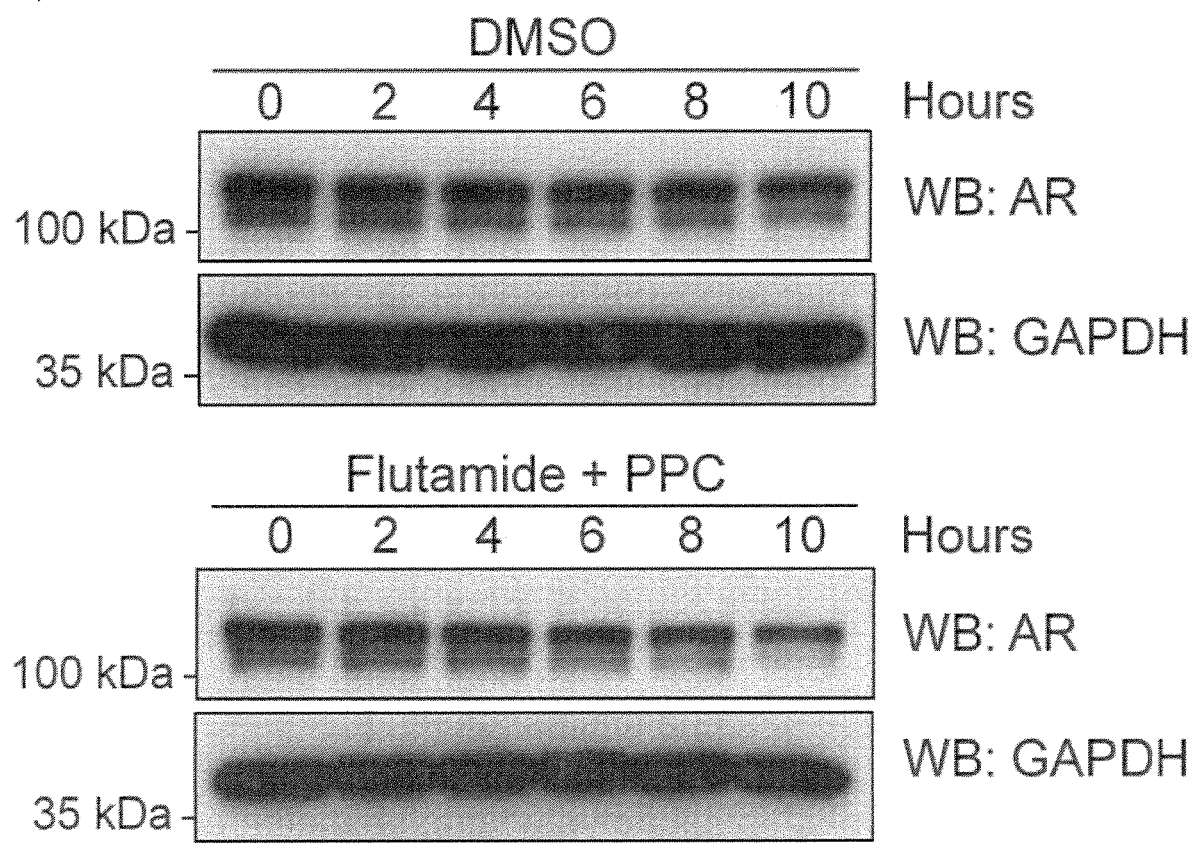
Figure 13:
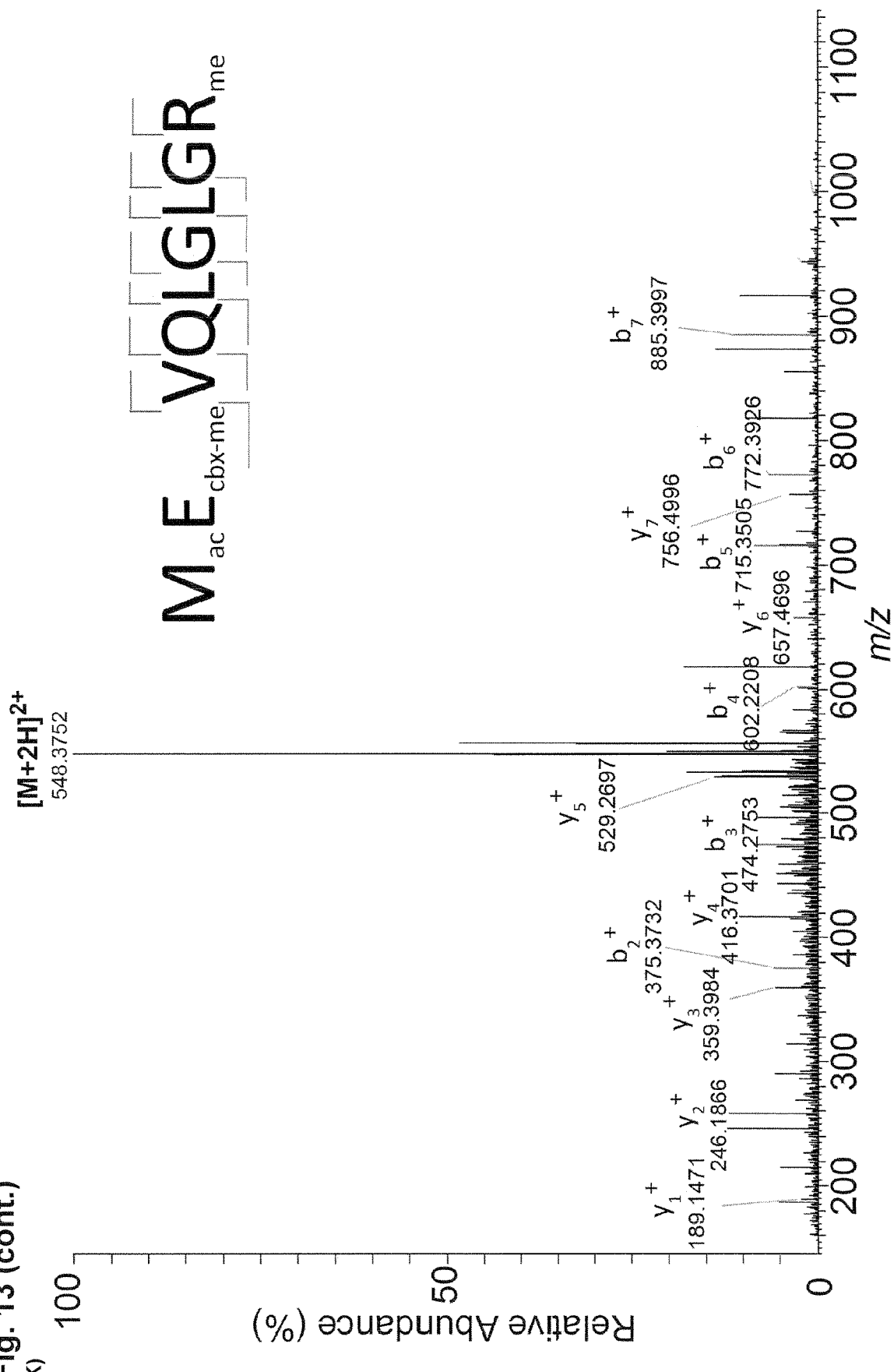

Fig. 13
A)
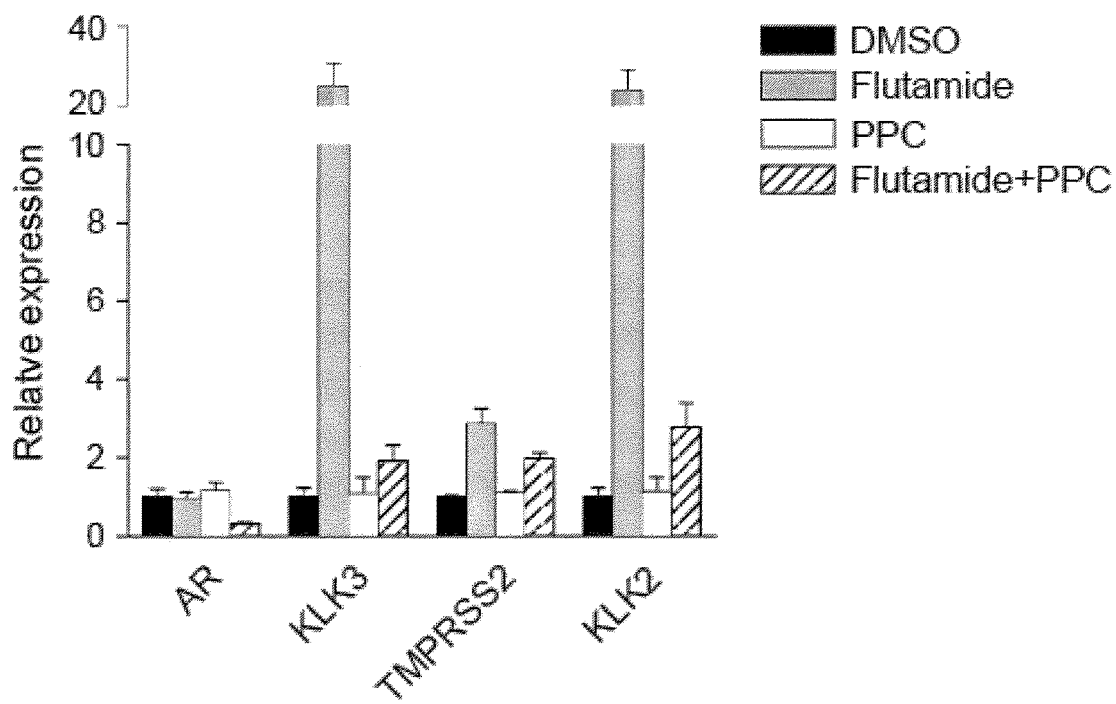
B)
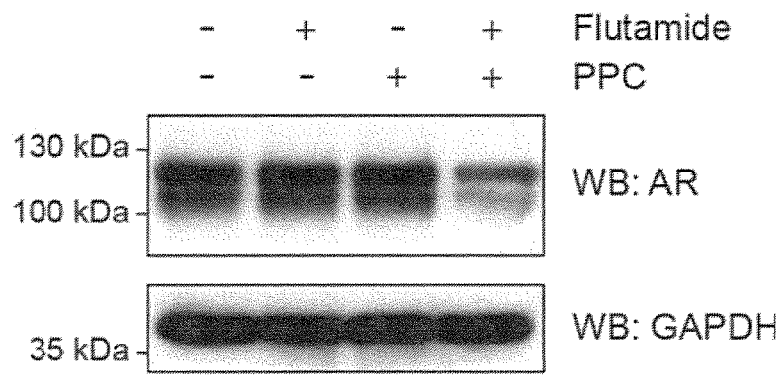

C)

D)

Fig. 13 (cont.)
E)
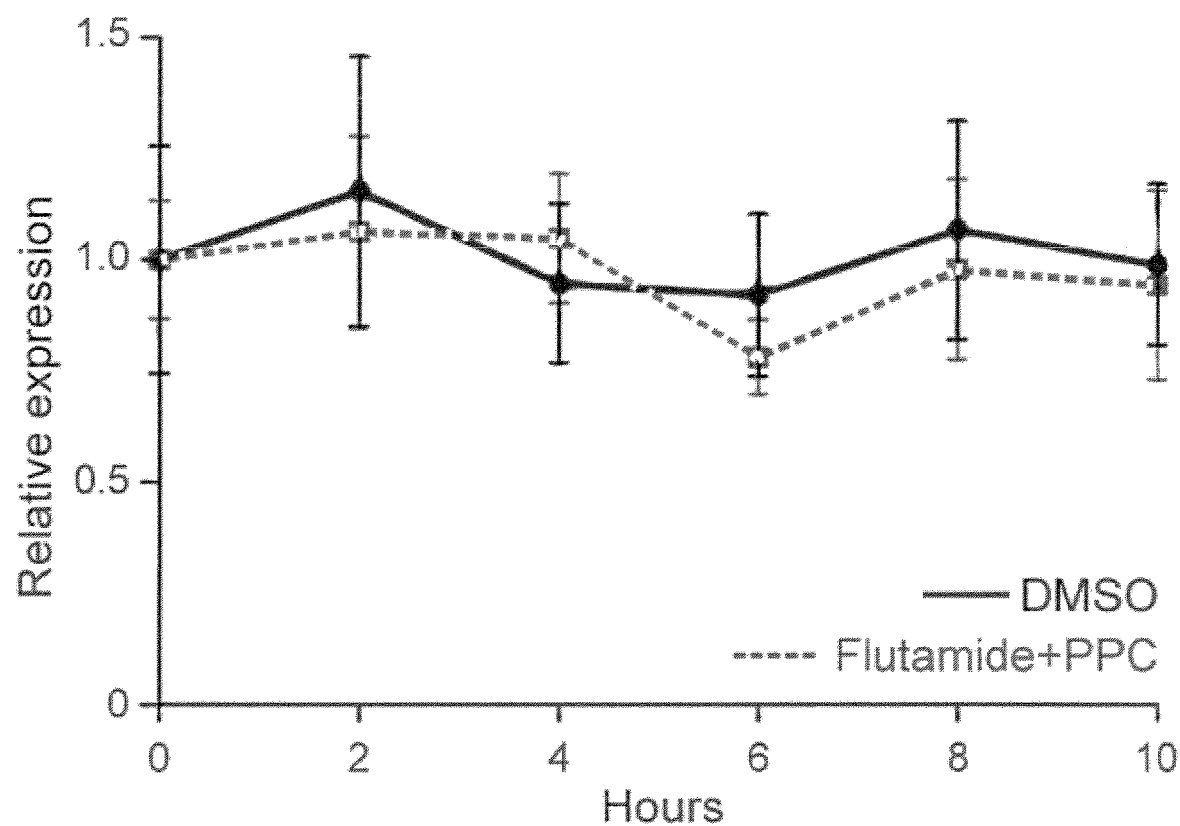
F)
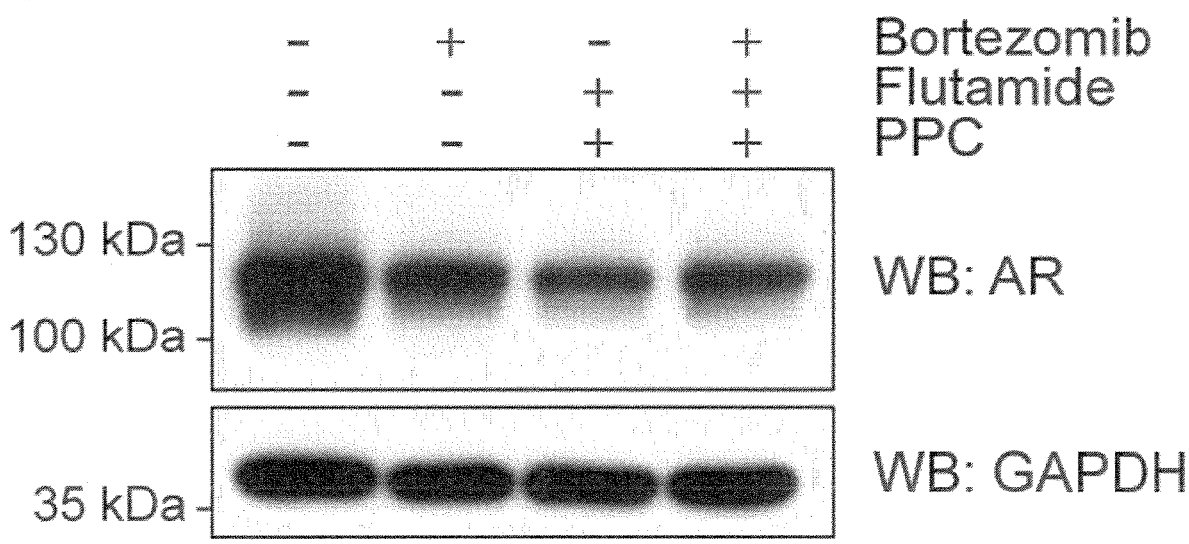

G)

Fig. 13 (cont.)
H)
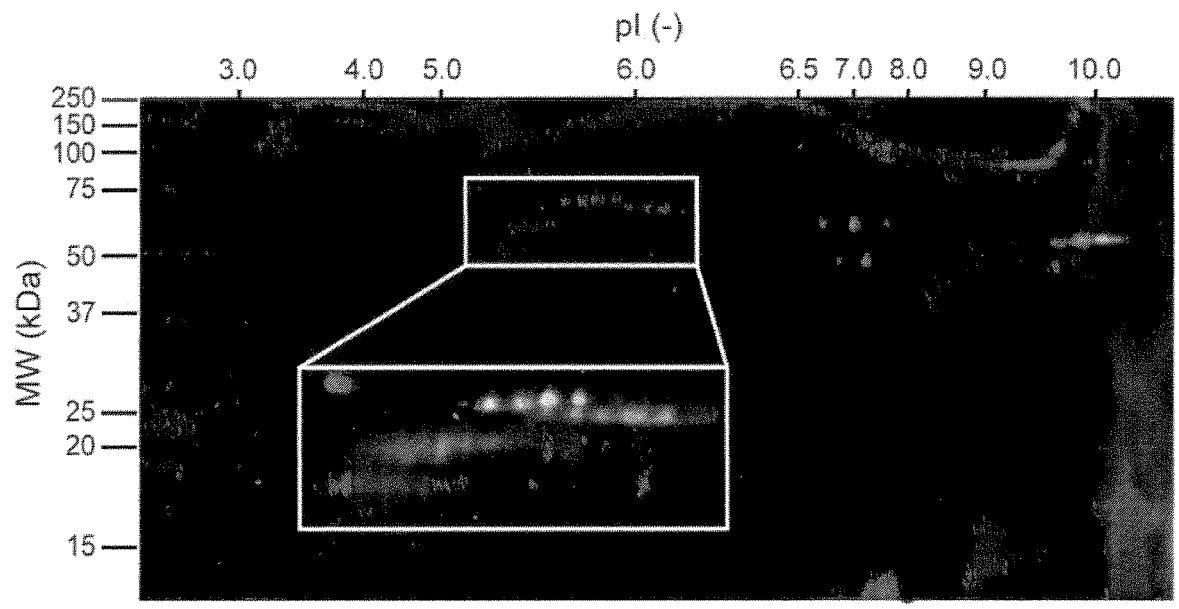
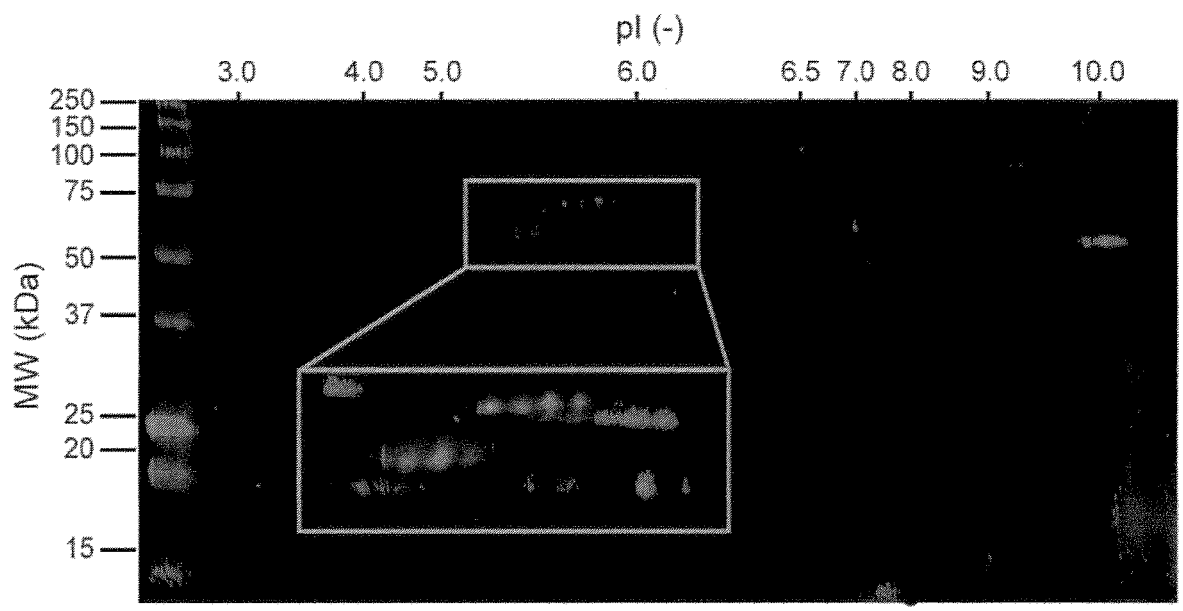

Fig. 13 (cont.)
I)
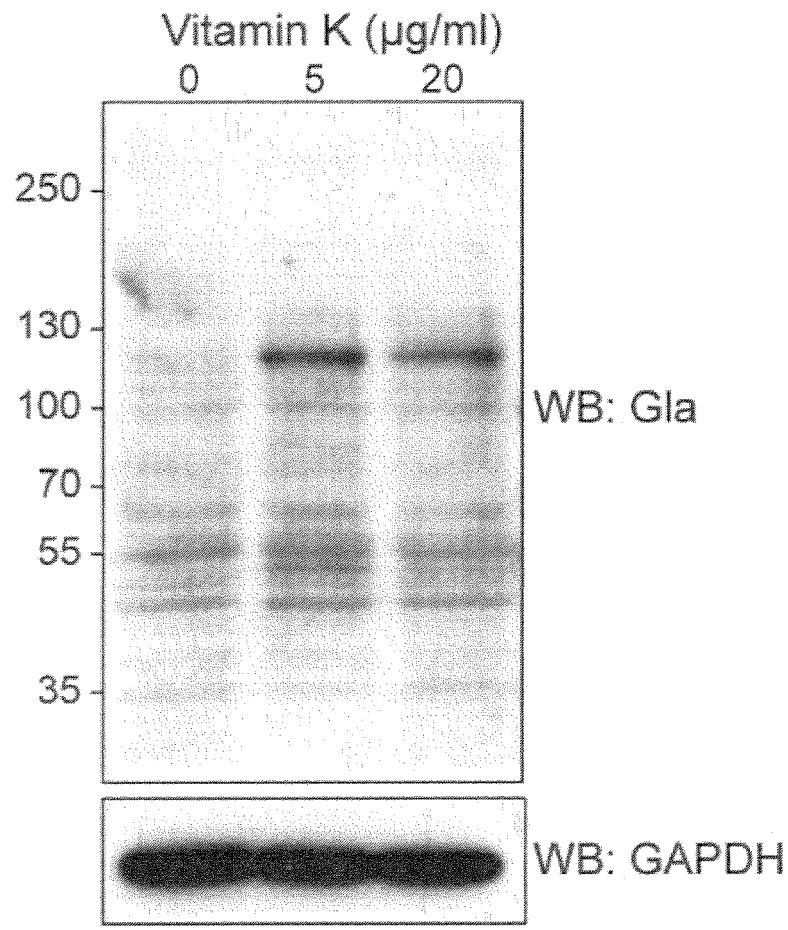
J)
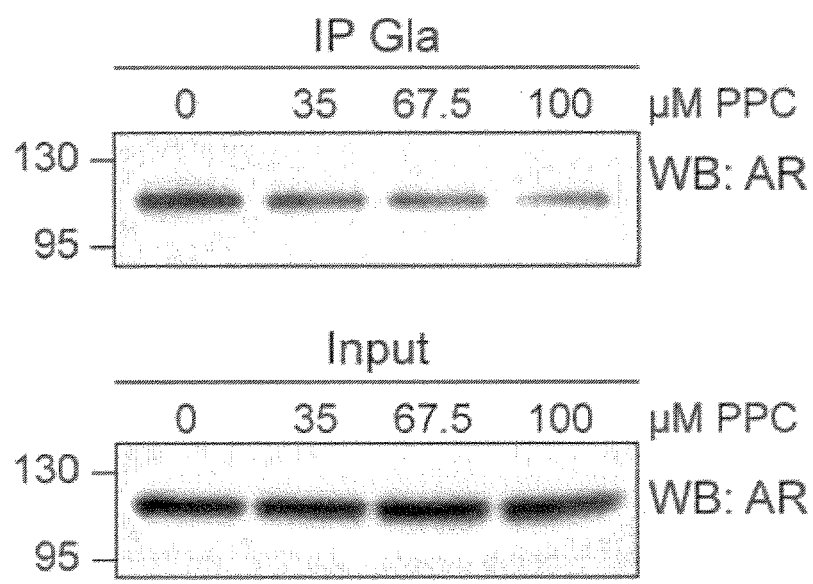

K)

Fig. 14
A)
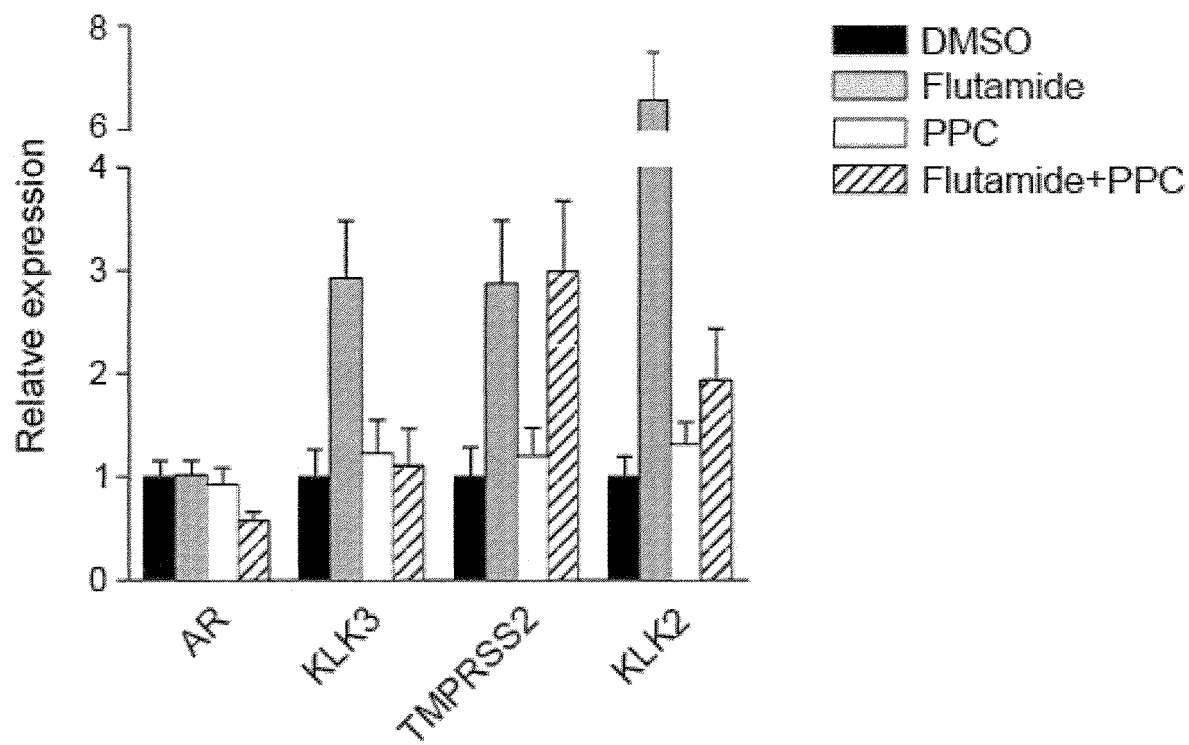
B)
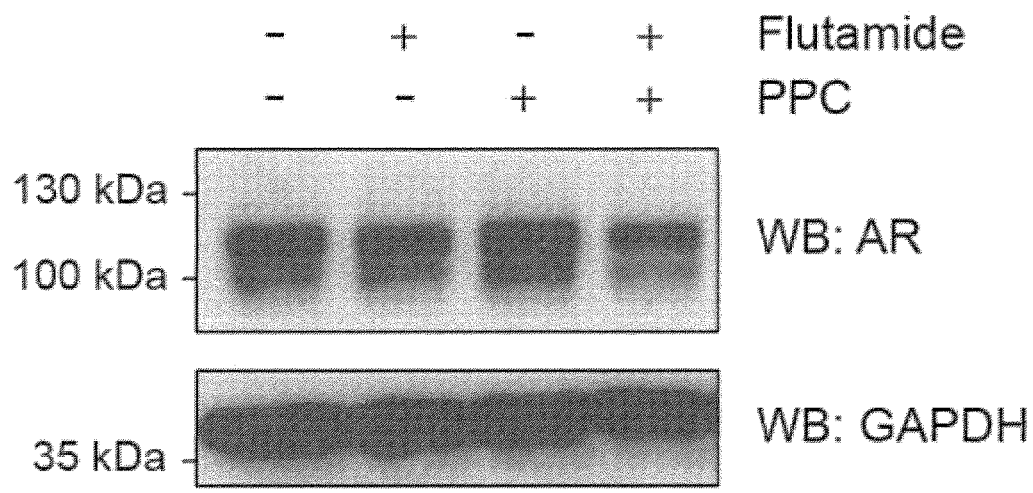

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
gaaagcgact tcaccgcac                                                    19

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
aaaacatggt ccctggcagt                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
tgtacacgtg gtcaagtggg                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tgtgcatgcg gtactcattg                                                   20

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
actctggctt cacagtttgg a                                                 21

```
<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
cgcacaggta cttctgtttc c                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7
ggtgaccaag ttcatgctgt g                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
gtgtccttga tccacttccg                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ctgccaaggt gcttctcatt                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
ctgtcaccct ggcaagaatc                                                20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
ctgtcagagc ctgccaagat                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 12
gcaagaactc ctctggttcg                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ctgtctggcg gcaccaccat                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
gcaactaagt catagtccgc                                              20
```

COMBINATION OF AN ANTIANDROGEN WITH A VITAMIN K ANTAGONIST OR WITH A GAMMA-GLUTAMYL CARBOXYLASE INHIBITOR FOR THE THERAPY OF ANDROGEN RECEPTOR POSITIVE CANCER

This application is a national phase application under 35 U.S.C. § 371 of International Application No. PCT/EP2016/058990, filed Apr. 22, 2016, which claims benefit of European Application No. 15164648.6, filed Apr. 22, 2015, the entire contents of each of which are hereby incorporated by reference.

The present invention relates to the combination of an antiandrogen with a vitamin K antagonist or with a γ-glutamyl carboxylase inhibitor for use in the treatment or prevention of an androgen receptor positive cancer, such as prostate cancer, or a hyperactive androgen receptor signaling disease/disorder. The invention also relates to a vitamin K antagonist or a γ-glutamyl carboxylase inhibitor for use in resensitizing an antiandrogen-resistant prostate cancer to the treatment with an antiandrogen. The invention further provides a pharmaceutical composition comprising an antiandrogen, a vitamin K antagonist or a γ-glutamyl carboxylase inhibitor, and a pharmaceutically acceptable excipient.

Drug discovery is a challenging process easily spanning 10-15 years (Paul S M et al., *Nat Rev Drug Discov*, 2010, 9:203-14). In spite of the recent advances in screening and sequencing technologies, the number of new molecular entities (NMEs) approved every year still hobbles below expectations (Mullard A, *Nat Rev Drug Discov*, 2014, 13:85-9; Scannell J W et al., *Nat Rev Drug Discov*, 2012, 11:191-200). Both industry and academia have tried to bypass the hurdles in the drug discovery process by repositioning clinical compounds for additional therapeutic indications, so-called drug repurposing (Ashburn T T et al., *Nat Rev Drug Discov*, 2004, 3:673-83).

Patient diversity and drug resistance still represent significant obstacles in long-term pharmacological treatment of diseases such as cancer or infection (Holohan C et al., *Nat Rev Cancer*, 2013, 13:714-26; Clavel F et al., *N Engl J Med*, 2004, 350:1023-35). Multicomponent therapeutics have been shown to be an effective alternative in these circumstances (Bock C et al., *Nat Rev Cancer*, 2012, 12:494-501), providing a new strategy for more personalized medicine. Approved drugs proven to be safe, effective and bioavailable with their well-defined targets and mechanisms of action are an ideal starting points for generating new multicomponent regimes, and provide a fast-track to new clinical applications.

These unique features have prompted academic efforts to embark on the challenge of cataloguing and collecting all drugs approved for human or veterinary use (Chong C R et al., *Nat Chem Biol*, 2006, 2:415-6; Huang R et al., *Sci Transl Med*, 2011, 3:80 ps16). However, access to these comprehensive libraries is limited to scientists affiliated to corresponding institutions or to external collaborators when screenings are performed on site. Moreover, a systematic pairwise combinatorial high-throughput screen (HTS) of all 14,814 molecules currently in the NCGC pharmaceutical collection (Huang R et al., *Sci Transl Med*, 2011, 3:80 ps16) would generate more than 100 million data points, an effort beyond the capacity of screening facilities. Smaller libraries containing between 780 and 1600 approved drugs are commercially available, however they do not cover all drug classes.

In the context of the present invention, a set of representative FDA-approved drugs was computationally derived and used to generate a collection that optimally captures the chemical and biological diversity of all clinical compounds while fitting to a single 384-well screening plate. This collection was annotated with reported human maximum plasma concentrations to encourage HTS at pharmacologically relevant doses. Moreover, for all substances administered as prodrugs the respective active form was included. This collection of clinical compounds was named the CeMM Library of Unique Drugs (CLOUD). The non-redundant nature of this library allows for the systematic investigation of all combinations of CLOUD compounds.

In a combinatorial HTS using the CLOUD library, it was surprisingly found that antiandrogens such as flutamide interact with vitamin K antagonists such as phenprocoumon to effect a synergistically enhanced inhibition of androgen receptor (AR) signaling, as further described in the appended examples.

Androgen receptor signaling is known to play a crucial role in the pathogenesis of prostate cancer and is also involved in the development of other androgen receptor positive cancers (Chen Y et al., *Lancet Oncol*, 2009, 10:981-91; Mills I G, *Nat Rev Cancer*, 2014, 14:187-98; Taplin M E, *Nat Clin Pract Oncol*, 2007, 4:236-44; Wirth M P et al., *Eur Urol*, 2007, 51(2):306-13). Further diseases/disorders involving hyperactive androgen receptor signaling include, e.g., hyperandrogenism (Ibanez L et al., *J Clin Endocrinol Metab*, 2003, 88:3333-3338), spinal-bulbar muscular atrophy (Matsumoto T et al., *Annu Rev Physiol*, 2013, 75:201-224), benign prostatic hyperplasia (Izumi K et al., *Am J Pathol*, 2013, 182:1942-1949), hypersexuality, paraphilia (Guay D R, *Clin Ther*, 2009, 31:1-31), acne, seborrhea, hirsutism (Lai J J et al., *Arch Dermatol Res*, 2013, 304:499-510), androgenic alopecia, hidradenitis suppurativa, and polycystic ovary syndrome (Lin et al., *Int J Gynaecol Obstet*, 2013, 120:115-118). The inhibition of androgen receptor signaling with antiandrogens that antagonize the androgen receptor has been used or proposed for the treatment of such conditions. The synergistically enhanced inhibition of androgen receptor signaling which is achieved by the combination of an antiandrogen and a vitamin K antagonist in accordance with the present invention thus provides an improved therapy of androgen receptor positive cancer, including in particular prostate cancer, as well as hyperactive androgen receptor signaling diseases/disorders.

The androgen receptor normally resides in the cytoplasm bound to chaperones such as HSP90 (Brinkmann A O et al., *J Steroid Biochem Mol Biol*, 1999, 69:307-13). Upon binding of dihydrotestosterone (DHT) the androgen receptor changes its conformation and translocates to the nucleus, where it binds androgen responsive elements (AREs) driving the transcription of canonical targets such as KLK3 (also known as prostate specific antigen PSA), TMPRSS2 and KLK2 (Tran C et al., *Science*, 2009, 324:787-90; Murtha P et al., *Biochemistry (Mosc.)*, 1993, 32:6459-64). Flutamide is a non-steroidal antiandrogen approved for the treatment of prostate cancer (Chen Y et al., *Lancet Oncol*, 2009, 10:981-91), acting as a DHT-competitive AR antagonist (Liao S et al., *Endocrinology*, 1974, 94:1205-9). However, mutations in the AR ligand binding domain such as T877A modulate the interaction with antiandrogens, switch their activity from an antagonistic to an agonistic one (Veldscholte J et al., *J Steroid Biochem Mol Biol*, 1992, 41:665-9; Gaddipati J P et al., *Cancer Res*, 1994, 54:2861-4) and have been described as a common resistance mechanism to antiandrogen therapy in prostate cancer patients (Feldman B J et al., *Nat Rev*

Cancer, 2001, 1:34-45). Thus, even though patients usually respond well to antiandrogen (mono)therapy initially, cancer cells inevitably develop resistance mechanisms hampering the efficiency of the treatment (Chen C D et al., *Nat Med*, 2004, 10:33-9).

Watanabe A et al., *Drug Metab Dispos*, 2009, 37(7):1513-20 investigates the hydrolysis of flutamide and reports that it is hydrolyzed exclusively by human arylacetamide deacetylase. In a specific experiment, flutamide, disulfiram and various hydrolases were used in a biochemical assay to examine the potential involvement of monoacylglycerol lipase in the hydrolysis of flutamide. However, Watanabe et al. fails to teach or suggest any therapeutic use of the combination of flutamide and disulfiram, or any pharmaceutical composition comprising these two agents, let alone the use of the combination of these agents in the treatment of an androgen receptor positive cancer.

Vitamin K is the cofactor of the enzyme γ-glutamyl carboxylase (GGCX), which catalyzes the γ-carboxylation of glutamic acid residues in proteins involved in the coagulation cascade (Stenflo J et al., *Proc Natl Acad Sci USA*, 1974, 71:2730-3; Rost S et al., *Nature*, 2004, 427:537-41). In this reaction, GGCX oxidizes vitamin K hydroquinone to vitamin K epoxide (Suttie J W, *Annu Rev Biochem*, 1985, 54:459-77). Vitamin K epoxide reductase complex subunit 1 (VKORC1) converts oxidized vitamin K back to the reduced form (Li T et al., *Nature*, 2004, 427:541-44; Rieder M J et al., *N Engl J Med*, 2005, 352:2285-93) sustaining the cellular pool of the cofactor. Phenprocoumon (PPC), a coumarin anticoagulant used for the treatment of thrombosis, inhibits VKORC1 and therefore vitamin K-dependent γ-carboxylation required to activate the coagulation cascade (Paikin J S et al., *Nat Rev Cardiol*, 2010, 7:498-509).

Therapeutic uses of certain vitamin K antagonists are described in Pottegård A et al., *Int J Cancer*, 2013, 132(11): 2606-12. Ketola K et al., *PLoS One*, 2012, 7(12):e51470 relates to the use of disulfiram in combination with sunitinib for the treatment of prostate cancer. Further therapeutic applications of disulfiram are disclosed in US 2014/0037715, Kapoor S, *Chem Biol Interact*, 2013, 204(3):200, and Lin J et al., *Prostate*, 2011, 71(4):333-43.

It has been shown in the context of the present invention that vitamin K antagonists such as phenprocoumon modulate the interaction of antiandrogens such as flutamide with the androgen receptor, as detailed in the appended examples. In particular, phenprocoumon was found to restrain the induction of androgen receptor canonical targets by flutamide in a prostate cancer cell line carrying an androgen receptor T877A mutation where flutamide normally behaves as an agonist. The combination of the two approved drugs leads to AR degradation and apoptosis. Importantly, it has been shown that the N-terminal domain of AR is γ-carboxylated and this post-translational modification is inhibited by phenprocoumon, thereby discovering the molecular basis for the drug synergy. These findings indicate that vitamin K antagonists such as phenprocoumon can be repurposed in the clinic to address resistance of androgen positive cancers (particularly prostate cancer) to antiandrogens mediated by androgen receptor mutations such as T877A. Thus, the combination of an antiandrogen and a vitamin K antagonist as provided by the present invention is not only advantageous because of its synergistically enhanced inhibitory effect on androgen receptor signaling but also because it can be used for the therapy of antiandrogen-resistant cancer (particularly androgen-resistant prostate cancer). The combination of an antiandrogen and a vitamin K antagonist allows to prevent or reduce the development of antiandrogen resistance through androgen receptor mutations such as T877A in androgen positive cancers, thus providing a particularly advantageous therapeutic approach for the treatment of androgen positive cancers, including prostate cancer. The present invention thus solves the problem of providing an improved therapy for androgen positive cancer, including in particular prostate cancer, as well as hyperactive androgen receptor signaling diseases/disorders.

Accordingly, the present invention provides a combination of an antiandrogen and a vitamin K antagonist for use in treating or preventing an androgen receptor positive cancer or a hyperactive androgen receptor signaling disease/disorder.

The invention also provides an antiandrogen for use in treating or preventing an androgen receptor positive cancer or a hyperactive androgen receptor signaling disease/disorder, wherein the antiandrogen is to be administered in combination with a vitamin K antagonist.

The invention likewise relates to a vitamin K antagonist for use in treating or preventing an androgen receptor positive cancer or a hyperactive androgen receptor signaling disease/disorder, wherein the vitamin K antagonist is to be administered in combination with an antiandrogen.

The invention further provides a pharmaceutical composition comprising an antiandrogen, a vitamin K antagonist, and a pharmaceutically acceptable excipient. Moreover, the invention relates to the aforementioned pharmaceutical composition for use in treating or preventing an androgen receptor positive cancer or a hyperactive androgen receptor signaling disease/disorder.

Furthermore, the present invention provides a vitamin K antagonist for use in resensitizing an antiandrogen-resistant prostate cancer to the treatment with an antiandrogen. The invention likewise refers to a vitamin K antagonist for use in resensitizing an androgen receptor positive cancer (e.g., prostate cancer) that is resistant to antiandrogen monotherapy, particularly an androgen receptor positive cancer (e.g., prostate cancer) having one or more androgen receptor mutations (such as, e.g., T877A, T877S, W741C, F876L and/or H874Y), to the treatment with an antiandrogen.

Antiandrogens constitute an established class of pharmacological agents that antagonize, block or prevent androgen receptor signaling. The term "antiandrogen" thus refers, in particular, to an androgen receptor antagonist (AR antagonist) and/or an androgen receptor signaling antagonist (AR signaling antagonist). The antiandrogen to be used in accordance with the present invention may be a steroidal antiandrogen or a non-steroidal antiandrogen, and is preferably a non-steroidal antiandrogen. Exemplary antiandrogens which can be used in accordance with the invention include, in particular, flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, chlormadinone acetate, delanterone, dienogest, drospirenone, epitestosterone, inocoterone, metogest, nomegestrol, nomegestrol acetate, nordinone, norgestimate, osaterone, oxendolone, rosterolone, topterone, zanoterone, RU-58642, RU-58841, and pharmaceutically acceptable salts and solvates of any one of these agents. Preferably, the antiandrogen to be used in accordance with the present invention is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, and pharmaceutically acceptable salts and solvates thereof. More preferably, the antiandrogen is selected from flutamide, nilutamide, bicalutamide, enzalutamide, 2-hydroxyflutamide, BMS-641988, ARN-509, and pharmaceutically acceptable salts and solvates thereof. Even more preferably, the antiandrogen is selected from flutamide, nilutamide, bicalutamide, enzalutamide, 2-hydroxyflutamide, BMS-641988, and ARN-509. Yet even more preferably, the antiandrogen is flutamide or bicalutamide. Still more preferably, the antiandrogen is flutamide.

Vitamin K antagonists are a class of pharmacological agents that suppress or reduce the action of vitamin K by inhibiting the conversion of oxidized vitamin K (i.e., vitamin K 2,3-epoxide) to its active reduced form (i.e., vitamin K hydroquinone), particularly by inhibiting the enzyme vitamin K epoxide reductase (EC 1.17.4.4; previously EC 1.1.4.1) or vitamin K epoxide reductase complex subunit 1 (VKORC1). The term "vitamin K antagonist" thus refers, in particular, to a vitamin K epoxide reductase inhibitor, and preferably refers to a vitamin K epoxide reductase complex subunit 1 inhibitor (VKORC1 inhibitor). The vitamin K antagonist to be used in accordance with the present invention may be, e.g., a 4-hydroxycoumarin derivative or a 1,3-indandione derivative. Preferably, the vitamin K antagonist is selected from phenprocoumon, dicoumarol, acenocoumarol, warfarin, ethyl biscoumacetate, anisindione, phenindione, clorindione, fluindione, 1-N-methyl-5-thiotetrazole, 5,5'-dithiobis(1-methyltetrazole), disulfiram, and N-ethylmaleimide. More preferably, the vitamin K antagonist is selected from phenprocoumon, dicoumarol, acenocoumarol, warfarin, ethyl biscoumacetate, anisindione, phenindione, clorindione, fluindione, 1-N-methyl-5-thiotetrazole, 5,5'-dithiobis(1-methyltetrazole), and N-ethylmaleimide. Even more preferably, the vitamin K antagonist is phenprocoumon or warfarin. A particularly preferred vitamin K antagonist is phenprocoumon. A further particularly preferred vitamin K antagonist is warfarin. Yet even more preferably, the vitamin K antagonist is phenprocoumon. Pharmaceutically acceptable salts and solvates of vitamin K antagonists can also be used.

Since vitamin K is required as a cofactor by the enzyme γ-glutamyl carboxylase (GGCX) (EC 4.1.1.90), which catalyzes the carboxylation of glutamate (Glu) residues in certain proteins to γ-carboxyglutamate (Gla) residues with the concomitant oxidation of the reduced hydroquinone form of vitamin K to vitamin K epoxide, it is contemplated that a γ-glutamyl carboxylase inhibitor (GGCX inhibitor) can also be used in place of (or in addition to) a vitamin K antagonist in the combination with an antiandrogen according to the present invention. An exemplary γ-glutamyl carboxylase inhibitor is, for instance, calumenin (Wajih N et al., *J Biol Chem*, 2004, 279:25276-83). Accordingly, the invention encompasses the use of an antiandrogen in combination with (i) a vitamin K antagonist or (ii) a γ-glutamyl carboxylase inhibitor or (iii) both a vitamin K antagonist and a γ-glutamyl carboxylase inhibitor.

Thus, the invention also relates to a combination of an antiandrogen and a γ-glutamyl carboxylase inhibitor for use in treating or preventing an androgen receptor positive cancer or a hyperactive androgen receptor signaling disease/disorder. The invention further provides an antiandrogen for use in treating or preventing an androgen receptor positive cancer or a hyperactive androgen receptor signaling disease/disorder, wherein the antiandrogen is to be administered in combination with a γ-glutamyl carboxylase inhibitor. The invention likewise provides a γ-glutamyl carboxylase inhibitor for use in treating or preventing an androgen receptor positive cancer or a hyperactive androgen receptor signaling disease/disorder, wherein the γ-glutamyl carboxylase inhibitor is to be administered in combination with an antiandrogen. The present invention furthermore relates to a pharmaceutical composition comprising an antiandrogen, a γ-glutamyl carboxylase inhibitor, and a pharmaceutically acceptable excipient. The invention also relates to this pharmaceutical composition for use in treating or preventing an androgen receptor positive cancer or a hyperactive androgen receptor signaling disease/disorder. Moreover, the invention provides a γ-glutamyl carboxylase inhibitor for use in resensitizing an antiandrogen-resistant prostate cancer to the treatment with an antiandrogen. The invention also relates to a γ-glutamyl carboxylase inhibitor for use in resensitizing an androgen receptor positive cancer (e.g., prostate cancer) that is resistant to antiandrogen monotherapy, particularly an androgen receptor positive cancer (e.g., prostate cancer) having one or more androgen receptor mutations (such as, e.g., T877A, T877S, W741C, F876L and/or H874Y), to the treatment with an antiandrogen.

The present invention furthermore relates to the use of an antiandrogen in combination with a vitamin K antagonist or with a γ-glutamyl carboxylase inhibitor for the preparation of a medicament for treating or preventing an androgen receptor positive cancer or a hyperactive androgen receptor signaling disease/disorder. The invention likewise provides the use of an antiandrogen for the preparation of a medicament for treating or preventing an androgen receptor positive cancer or a hyperactive androgen receptor signaling disease/disorder, wherein the antiandrogen is to be administered in combination with a vitamin K antagonist or a γ-glutamyl carboxylase inhibitor. The invention also relates to the use of a vitamin K antagonist for the preparation of a medicament for treating or preventing an androgen receptor positive cancer or a hyperactive androgen receptor signaling disease/disorder, wherein the vitamin K antagonist is to be administered in combination with an antiandrogen. The invention further relates to the use of a γ-glutamyl carboxylase inhibitor for the preparation of a medicament for treating or preventing an androgen receptor positive cancer or a hyperactive androgen receptor signaling disease/disorder, wherein the γ-glutamyl carboxylase inhibitor is to be administered in combination with an antiandrogen. Moreover, the invention refers to the use of a vitamin K antagonist for the preparation of a medicament for resensitizing an antiandrogen-resistant prostate cancer to the treatment with an antiandrogen. The invention also relates to the use of a γ-glutamyl carboxylase inhibitor for the preparation of a medicament for resensitizing an antiandrogen-resistant prostate cancer to the treatment with an antiandrogen. The invention further relates to the use of a vitamin K antagonist or a γ-glutamyl carboxylase inhibitor for the preparation of a medicament for resensitizing an androgen receptor positive cancer (e.g., prostate cancer) that is resistant to antiandrogen monotherapy, particularly an androgen receptor positive cancer (e.g., prostate cancer) having one or more androgen receptor mutations (such as, e.g., T877A, T877S, W741C F876L and/or H874Y), to the treatment with an antiandrogen.

The present invention likewise relates to a method of treating or preventing an androgen receptor positive cancer or a hyperactive androgen receptor signaling disease/disorder, the method comprising administering an antiandrogen in combination with a vitamin K antagonist or in combination with a γ-glutamyl carboxylase inhibitor to a subject in need thereof. In particular, the invention relates to a method of treating or preventing an androgen receptor positive cancer (such as prostate cancer) or a hyperactive androgen receptor signaling disease/disorder, the method comprising administering an antiandrogen in combination with a vitamin K antagonist to a subject in need thereof. The invention also relates to a method of treating or preventing an androgen receptor positive cancer (such as prostate cancer) or a hyperactive androgen receptor signaling disease/disorder, the method comprising administering an antiandrogen in combination with a γ-glutamyl carboxylase inhibitor to a subject in need thereof. Furthermore, the invention provides a method of resensitizing an antiandrogen-resistant prostate cancer to the treatment with an antiandrogen, the method comprising administering a vitamin K antagonist or a γ-glutamyl carboxylase inhibitor (preferably a vitamin K antagonist) to a subject in need thereof.

The androgen receptor positive cancer to be treated or prevented in accordance with the present invention is a cancer in which the androgen receptor is expressed. This cancer is preferably an androgen receptor dependent cancer, i.e., a cancer whose survival and/or progression is dependent on androgen receptor signaling. It is preferred that the androgen receptor positive cancer (or the androgen receptor dependent cancer) to be treated or prevented is selected from prostate cancer, breast cancer (e.g., estrogen receptor α (ERα)-negative breast cancer), endometrial cancer, liver cancer, laryngeal cancer, osteosarcoma, glioblastoma, chondrosarcoma, Ewing's sarcoma, and testicular cancer. More preferably, the androgen receptor positive cancer (or the androgen receptor dependent cancer) to be treated or prevented is selected from prostate cancer, osteosarcoma, glioblastoma, chondrosarcoma, and Ewing's sarcoma. Most preferably, the cancer to be treated or prevented is prostate cancer.

It is furthermore particularly envisaged that the androgen receptor positive cancer (or the androgen receptor dependent cancer) to be treated or prevented is antiandrogen-resistant, i.e., is resistant to the monotherapeutic treatment with an antiandrogen (such as, e.g., flutamide or bicalutamide). Thus, the androgen receptor positive cancer (or the androgen receptor dependent cancer) may be, e.g., flutamide-resistant and/or bicalutamide-resistant. In particular, the antiandrogen-resistant cancer may be an androgen receptor positive cancer (or an androgen receptor dependent cancer) expressing a mutant androgen receptor, such as an androgen receptor having a T877A mutation. It is thus preferred that the androgen receptor positive cancer (or the androgen receptor dependent cancer) to be treated or prevented has one or more androgen receptor mutations, which are preferably selected from an androgen receptor T877A mutation, an androgen receptor T877S mutation, an androgen receptor W741C mutation, an androgen receptor F876L mutation, and an androgen receptor H874Y mutation, and more preferably has an androgen receptor T877A mutation. Any cancer referred to in this paragraph is preferably selected from prostate cancer, breast cancer, endometrial cancer, liver cancer, laryngeal cancer, osteosarcoma, glioblastoma, chondrosarcoma, Ewing's sarcoma, and testicular cancer, more preferably from prostate cancer, osteosarcoma, glioblastoma, chondrosarcoma, and Ewing's sarcoma, and is most preferably prostate cancer.

Thus, it is particularly preferred that the cancer to be treated or prevented is an antiandrogen-resistant prostate cancer, i.e., a prostate cancer that is resistant to the monotherapeutic treatment with an antiandrogen (e.g., a flutamide-resistant prostate cancer or a bicalutamide-resistant prostate cancer). In particular, the antiandrogen-resistant prostate cancer may be a prostate cancer expressing a mutant androgen receptor, such as an androgen receptor having a T877A mutation. The prostate cancer to be treated or prevented may thus be a prostate cancer having one or more androgen receptor mutations, which are preferably selected from an androgen receptor T877A mutation, an androgen receptor T877S mutation, an androgen receptor W741C mutation, an androgen receptor F876L mutation, and an androgen receptor H874Y mutation, and is more preferably a prostate cancer having an androgen receptor T877A mutation.

It is likewise preferred that the antiandrogen-resistant prostate cancer to be resensitized to the treatment with an antiandrogen using a vitamin K antagonist or a γ-glutamyl carboxylase inhibitor (preferably using a vitamin K antagonist) has one or more androgen receptor mutations selected from an androgen receptor T877A mutation, an androgen receptor T877S mutation, an androgen receptor W741C mutation, an androgen receptor F876L mutation, and an androgen receptor H874Y mutation, and more preferably has an androgen receptor T877A mutation.

The hyperactive androgen receptor signaling disease/disorder to be treated or prevented in accordance with the present invention is preferably selected from hyperandrogenism, spinal-bulbar muscular atrophy ("SBMA" or Kennedy's disease), benign prostatic hyperplasia, hypersexuality, paraphilia, acne, seborrhea, hirsutism, androgenic alopecia, hidradenitis suppurativa, and polycystic ovary syndrome. It is furthermore preferred that the subject to be treated expresses mutant androgen receptor having one or more mutations selected from an androgen receptor T877A mutation, an androgen receptor T877S mutation, an androgen receptor W741C mutation, an androgen receptor F876L mutation, and an androgen receptor H874Y mutation, more preferably a mutant androgen receptor having an androgen receptor T877A mutation.

As described above, the present invention relates to the combination of an antiandrogen with a vitamin K antagonist (or with a γ-glutamyl carboxylase inhibitor) for use in treating or preventing an androgen receptor positive cancer or a hyperactive androgen receptor signaling disease/disorder. The antiandrogen and the vitamin K antagonist (or the antiandrogen and the γ-glutamyl carboxylase inhibitor) can be provided in separate pharmaceutical formulations. Such separate formulations can be administered either simultaneously or sequentially (e.g., the formulation comprising the antiandrogen may be administered first, followed by the administration of the formulation comprising the vitamin K antagonist or the γ-glutamyl carboxylase inhibitor, or vice versa). However, the antiandrogen and the vitamin K antagonist (or the antiandrogen and the γ-glutamyl carboxylase inhibitor) can also be provided in a single pharmaceutical formulation. Accordingly, the invention also relates to a pharmaceutical composition comprising an antiandrogen, a vitamin K antagonist (or a γ-glutamyl carboxylase inhibitor), and a pharmaceutically acceptable excipient. This novel pharmaceutical composition is useful, in particular, for the treatment or prevention of an androgen receptor positive cancer (such as prostate cancer) or a hyperactive androgen receptor signaling disease/disorder.

The generation of the CeMM Library of Unique Drugs (CLOUD) is described in detail in the appended Example 1. Approved drugs are highly optimized molecules that can be used to address important biological questions. Moreover, a comprehensive library of clinical compounds can generate new leads for drug repurposing through single-molecule and combinatorial HTS. When attempting to physically obtain a complete set of all approved drugs for screening purposes, the inventors realized that no commercially available compound collection covers all drug classes and that combinatorial screenings of even relatively small libraries would overload the infrastructure of most screening platforms. Therefore, an extensive literature search was performed and a set of FDA-approved drugs was cheminformatically selected, representing the entire target and chemical space of all clinical compounds. Using a clustering algorithm on systemically active approved drugs with known targets, only structurally unique molecules were selected. Approved drugs with unknown targets and the active forms of prodrugs were added to these compounds to allow for both biochemical and cellular screens. This compound set was called the CeMM Library of Unique Drugs (CLOUD). In contrast to existing collections, all CLOUD drugs fit to a single 384-well plate, are screened at their respective plasma concentration, and include active forms of compounds clinically administered as prodrugs. The non-redundant nature of the CLOUD allows for combinatorial screenings of drugs already used in clinical settings, entailing a strong translational potential.

In an HTS of all pairwise combinations of CLOUD drugs a synergistic interaction between the antiandrogen flutamide and the vitamin K antagonist phenprocoumon was surprisingly found. Importantly, it was demonstrated that this synergy is conserved among other members of the drug classes these compounds represent in the CLOUD library, validating the reductionist approach of the CLOUD as a non-redundant collection of all FDA-approved drugs. Flutamide is an AR antagonist approved for the treatment of prostate cancer while phenprocoumon, which has been approved as an anticoagulant for treatment of thrombosis, inhibits vitamin K-dependent protein γ-carboxylation. As described in Example 3, it has been shown that the combination of these drugs impairs the growth of AR-dependent LNCaP prostate cancer cells leading to apoptosis. LNCaP cells carry a T877A mutation in the AR ligand binding domain that causes an AR antagonist such as flutamide to switch from an AR antagonist to an agonist. The same mutation has been validated as a resistance mechanism to AR antagonists in prostate cancer patients. Importantly, the results provided herein indicate that resistance of T877A mutant AR to flutamide can be overcome by the concomitant administration of phenprocoumon. It has been concluded that in the presence of phenprocoumon, flutamide switches back to an antagonistic behavior inducing only marginally the transcription of AR signaling canonical targets (see Example 4). Mechanistically, a reduction in AR protein stability and amount was observed upon treatment of LNCaP cells with the combination. Degradation occurs, at least in part, via the proteasome as bortezomib could partly rescue AR protein depletion in the presence of flutamide and phenprocoumon. However, as AR regulates its own expression (Grad J M et al., Endocrinology, 2001, 142(3):1107-16), transcriptional changes are likely contributing to the overall decrease in protein abundance. Without being bound by theory, the downregulation of this important nuclear receptor is considered to operate as the main death trigger in AR-dependent LNCaP cells, eventually leading to apoptosis.

The post-translational modification of glutamic acid residues by γ-glutamyl carboxylase has been so far described for a restricted group of proteins involved in the coagulation cascade. It has only been found in the context of the present invention that γ-carboxylation occurs also on at least two glutamic acid residues of the AR N-terminal domain. This modification alters the thermal stability and isoelectric point of the receptor. The findings provided herein support a model where phenprocoumon precludes γ-carboxylation of AR while binding of flutamide to the uncarboxylated receptor would result in a conformational change that induces protein degradation.

It has thus been shown that a vitamin K antagonist such as phenprocoumon modulates the interaction of T877A mutated androgen receptor with an antiandrogen such as flutamide. This combination induces proteasomal degradation of the androgen receptor and apoptosis in AR-dependent prostate cancer cells. T877A mutated AR has been reported in prostate cancer patients and associated with resistance to flutamide. These results indicate that vitamin K antagonists like phenprocoumon can be clinically repurposed for the formulation of more specific prostate cancer treatments and could be employed to tackle resistance to antiandrogens in the therapy of prostate cancer.

The scope of the invention embraces the use of all pharmaceutically acceptable salt forms of the compounds of the drug combination provided herein (including the antiandrogen, the vitamin K antagonist and/or the γ-glutamyl carboxylase inhibitor) which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthaienesulfonate (napsylate), 3-phenylsulfonate, or camphorsulfonate salts; glycerophosphate salts; and acidic amino acid salts such as aspartate or glutamate salts.

Moreover, the scope of the invention embraces the use of the compounds of the drug combination provided herein (including the antiandrogen, the vitamin K antagonist and/or the γ-glutamyl carboxylase inhibitor) in any solvated form, including, e.g., solvates with water, for example hydrates, or with organic solvents such as, e.g., methanol, ethanol or acetonitrile, i.e., as a methanolate, ethanolate or acetonitrilate, respectively, or in the form of any polymorph.

Furthermore, where the compounds of the drug combination of the invention (including the antiandrogen, the vitamin K antagonist and/or the γ-glutamyl carboxylase inhibitor) exist in the form of different isomers, in particular stereoisomers (including, e.g., geometric isomers (or cis/trans isomers), enantiomers and diastereomers) or tautomers, all such isomers of the corresponding compounds are contemplated to be used in accordance with the invention, either in admixture or in pure or substantially pure form. As for stereoisomers, the invention embraces the use of isolated optical isomers of the respective compounds as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization.

The compounds of the drug combination provided herein (including the antiandrogen, the vitamin K antagonist and/or the γ-glutamyl carboxylase inhibitor) may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers.

The pharmaceutical compositions can be formulated by techniques known to the person skilled in the art, such as the techniques published in "Remington: The Science and Practice of Pharmacy", Pharmaceutical Press, 22$^{nd}$ edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds or the above described pharmaceutical compositions may be administered to a subject by any convenient route of administration, whether systemically/peripherally or at the site of desired action, including but not limited to one or more of: oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, said compounds or pharmaceutical compositions can be administered in the form of a suppository or pessary, or may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (see, e.g., U.S. Pat. No. 3,773,919), copolymers of L-glutamic acid and gamma-ethyl-L-glutamate (Sidman, U. et al., *Biopolymers* 22:547-556 (1983)), poly(2-hydroxyethyl methacrylate) (R. Langer et al., *J. Biomed. Mater. Res.* 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., *Proc. Natl. Acad. Sci.* (USA) 82:3688-3692 (1985); Hwang et al., *Proc. Natl. Acad. Sci.* (USA) 77:4030-4034 (1980); EP0052322; EP0036676; EP088046; EP0143949; EP0142641; JP 83-118008; U.S. Pat. Nos. 4,485,045; 4,544,545; and EP0102324.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of said compounds for pulmonary administration, particularly inhalation. Such dry powders may be prepared by spray drying under conditions which result in a substantially amorphous glassy or a substantially crystalline bioactive powder. Accordingly, dry powders of the compounds described herein can be made according to the emulsification/spray drying process disclosed in WO 99/16419 or WO 01/85136. Spray drying of solution formulations of said compounds can be carried out, e.g., as described generally in the "Spray Drying Handbook", 5th ed., K. Masters, John Wiley & Sons, Inc., NY (1991), in WO 97/41833, or in WO 03/053411.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

The present invention thus relates to the compounds or the pharmaceutical compositions provided herein, wherein the corresponding compounds, combinations of compounds, or pharmaceutical compositions are to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsuiar, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route. A particularly preferred route of administration is oral administration.

Accordingly, it is preferred that the antiandrogen and the vitamin K antagonist, or the antiandrogen and the γ-glutamyl carboxylase inhibitor, or the pharmaceutical composition comprising the antiandrogen and the vitamin K antagonist, or the pharmaceutical composition comprising the antiandrogen and the γ-glutamyl carboxylase inhibitor, are/is to be administered orally.

Typically, a physician will determine the actual dosage of the different compounds to be used in accordance with the present invention which will be most suitable for an individual subject. The specific dose level and frequency of dosage of these compounds for any particular individual subject may be varied and will depend upon a variety of factors including the activity of the corresponding specific compounds employed, the metabolic stability and length of action of these compounds, the age, body weight, general health, sex, diet, mode and time of administration, rate of excretion, drug combination, the severity of the particular condition, and the individual subject undergoing therapy. In particular, the dosage of the vitamin K antagonist (such as, e.g., phenprocoumon or warfarin) should be adjusted in consideration of the international normalized ratio (INR) and the prothrombin time (PT) of the individual subject to be treated in order to account for inter-individual variability which is primarily due to genetic SNPs in the CYP2C9 and VKORC1 genes, as known in the art and as described, e.g., in: Ansell J et al., Pharmacology and management of the vitamin K antagonists: American College of Chest Physicians Evidence-Based Clinical Practice Guidelines (8th Edition), *Chest,* 2008, 133(6 Suppl):160S-198S; Cushman M et al., Clinical practice guide on anticoagulant dosing and management of anticoagulant-associated bleeding complications in adults, *Am Soc Hematol,* 2011; and/or Hirsh J et al., Antithrombotic and thrombolytic therapy: American College of Chest Physicians Evidence-Based Clinical Practice Guidelines (8th Edition), Chest, 2008, 133(6 Suppl): 110S-112S.

A proposed, yet non-limiting dose of the compounds to be used in accordance with the present invention for oral administration to an adult human (e.g., a human of approximately 70 kg body weight) may be 0.1 to 2000 mg (preferably 1 mg to 1000 mg, more preferably 10 mg to 500 mg) of the antiandrogen per unit dose and 0.1 to 2000 mg (preferably 1 mg to 1000 mg) of the vitamin K antagonist (or the γ-glutamyl carboxylase inhibitor) per unit dose. The unit dose of each drug may be administered, e.g., 1 to 3 times per day. The unit dose of each drug may also be administered 1 to 7 times per week, e.g., with not more than one administration per day. It will be appreciated that it may be necessary to make routine variations to the dosage depending on the age and weight of the patient/subject as well as the severity of the condition to be treated. The precise dose and also the route of administration will ultimately be at the discretion of the attendant physician or veterinarian.

The combination of an antiandrogen with a vitamin K antagonist or with a γ-glutamyl carboxylase inhibitor according to the present invention can also be used in combination with other therapeutic agents, including in particular other anticancer agents, for the treatment or prevention of an androgen receptor positive cancer, such as prostate cancer. When the above-mentioned drug combination according to the present invention is used in combination with a further therapeutic agent active against the same disease, the dose of each compound may differ from that when the compound is used alone. The combination of the drug combination of the present invention with a further therapeutic agent may comprise the administration of the further therapeutic agent simultaneously/concomitantly or sequentially/separately with the compounds of the drug combination according to the invention.

Preferably, the further therapeutic agent to be administered in combination with the compounds of the drug combination of the present invention is an anticancer drug. The anticancer drug may be selected from: a tumor angiogenesis inhibitor (e.g., a protease inhibitor, an epidermal growth factor receptor kinase inhibitor, or a vascular endothelial growth factor receptor kinase inhibitor); a cytotoxic drug (e.g., an antimetabolite, such as purine and pyrimidine analog antimetabolites); an antimitotic agent (e.g., a microtubule stabilizing drug or an antimitotic alkaloid); a platinum coordination complex; an anti-tumor antibiotic; an alkylating agent (e.g., a nitrogen mustard or a nitrosourea); an endocrine agent (e.g., an adrenocorticosteroid, an androgen, an anti-androgen, an estrogen, an antiestrogen, an aromatase inhibitor, a gonadotropin-releasing hormone agonist, or a somatostatin analog); or a compound that targets an enzyme or receptor that is overexpressed and/or otherwise involved in a specific metabolic pathway that is misregulated in the tumor cell (e.g., ATP and GTP phosphodiesterase inhibitors, histone deacetylase inhibitors, protein kinase inhibitors (such as serine, threonine and tyrosine kinase inhibitors, e.g., Abelson protein tyrosine kinase inhibitors) and the various growth factors, their receptors and corresponding kinase inhibitors (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (e.g., cyclooxygenase-1 or cyclooxygenase-2 inhibitors), topoisomerase inhibitors (e.g., topoisomerase I inhibitors or topoisomerase II inhibitors), poly ADP ribose polymerase inhibitors (PARP inhibitors), and epidermal growth factor receptor (EGFR) inhibitors/antagonists.

An alkylating agent which can be used as an anticancer drug in combination with the compounds of the drug combination of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazine (such as temozolomide).

A platinum coordination complex which can be used as an anticancer drug in combination with the compounds of the drug combination of the present invention may be, for example, cisplatin, carboplatin, nedaplatin, oxaliplatin, satraplatin, or triplatin tetranitrate.

A cytotoxic drug which can be used as an anticancer drug in combination with the compounds of the drug combination of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with the compounds of the drug combination of the present invention may be, for example, a taxane (such as docetaxel, larotaxel, ortataxel, paclitaxel/taxol, or tesetaxel), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with the compounds of the drug combination of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with the compounds of the drug combination of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an anticancer drug in combination with the compounds of the drug combination of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

A PARP inhibitor which can be used as an anticancer drug in combination with the compounds of the drug combination of the present invention may be, for example, BMN-673, olaparib, rucaparib, veliparib, CEP 9722, MK 4827, BGB-290, or 3-aminobenzamide.

An EGFR inhibitor/antagonist which can be used as an anticancer drug in combination with the compounds of the drug combination of the present invention may be, for example, gefitinib, erlotinib, lapatinib, afatinib, neratinib, ABT-414, dacomitinib, AV-412, PD 153035, vandetanib, PKI-166, pelitinib, canertinib, icotinib, poziotinib, BMS-690514, CUDC-101, AP26113, XL647, cetuximab, panitumumab, zalutumumab, nimotuzumab, or matuzumab.

Further anticancer drugs may also be used in combination with the compounds of the drug combination of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine; elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, vorinostat, or iniparib.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the compounds of the drug combination of the present invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP1071752) and anti-TNF antibodies (see, e.g., Taylor P C. Antibody therapy for rheumatoid arthritis. Curr Opin Pharmacol. 2003. 3(3):323-328). Further antibodies, antibody fragments, antibody constructs and/or modified antibodies to be used in co-therapy approaches with the compounds of the drug combination of the invention can be found, e.g., in: Taylor P C. Curr Opin Pharmacol. 2003. 3(3):323-328; or Roxana A. Maedica. 2006. 1(1):63-65.

An anticancer drug which can be used in combination with the compounds of the drug combination of the present invention may, in particular, be an immunooncology therapeutic (such as an antibody (e.g., a monoclonal antibody or a polyclonal antibody), an antibody fragment, an antibody construct (e.g., a single-chain construct), or a modified antibody (e.g., a CDR-grafted antibody, a humanized antibody, or a "full humanized" antibody) targeting any one of CTLA-4, PD-1/PD-L1, TIM3, LAG3, OX4, CSF1R, IDO, or CD40. Such immunooncology therapeutics include, e.g., an anti-CTLA-4 antibody (particularly an antagonistic or pathway-blocking anti-CTLA-4 antibody; e.g., ipilimumab or tremelimumab), an anti-PD-1 antibody (particularly an antagonistic or pathway-blocking anti-PD-1 antibody; e.g., nivolumab (BMS-936558), pembrolizumab (MK-3475), pidilizumab (CT-011), AMP-224, or APE02058), an anti-PD-L1 antibody (particularly a pathway-blocking anti-PD-L1 antibody; e.g., BMS-936559, MEDI4736, MPDL3280A (RG7446), MDX-1105, or MEDI6469), an anti-TIM3 antibody (particularly a pathway-blocking anti-TIM3 antibody), an anti-LAG3 antibody (particularly an antagonistic or pathway-blocking anti-LAG3 antibody; e.g., BMS-986016, IMP701, or IMP731), an anti-OX4 antibody (particularly an agonistic anti-OX4 antibody; e.g., MEDI0562), an anti-CSF1R antibody (particularly a pathway-blocking anti-CSF1R antibody; e.g., IMC-CS4 or RG7155), an anti-IDO antibody (particularly a pathway-blocking anti-DO antibody), or an anti-CD40 antibody (particularly an agonistic anti-CD40 antibody; e.g., CP-870,893 or Chi Lob 7/4). Further immunooncology therapeutics are known in the art and are described, e.g., in: Kyi C et al., FEBS Lett, 2014, 588(2):368-76; Intlekofer A M et al., J Leukoc Biol, 2013, 94(1):25-39; Callahan M K et al., J Leukoc Biol, 2013, 94(1):41-53; Ngiow S F et al., Cancer Res, 2011, 71(21): 6567-71; and Blattman J N et al., Science, 2004, 305(5681): 200-5.

The combinations with further anticancer drugs referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compounds of the drug combination of the present invention or the further therapeutic agent may be administered first. When administration is simultaneous, the combination may be administered either in the same pharmaceutical composition or in different pharmaceutical compositions. When combined in the same formulation, it will be appreciated that the different compounds must be stable and compatible with each other and the other components of the formulation. When formulated separately, they may be provided in any convenient formulation.

The compounds of the drug combination of the present invention can also be administered in combination with physical therapy, such as radiotherapy. Radiotherapy may commence before, after, or simultaneously with administration of the compounds of the drug combination of the present invention. For example, radiotherapy may commence 1-10 minutes, 1-10 hours or 24-72 hours after administration of the corresponding compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a combination of an antiandrogen with a vitamin K antagonist or with a γ-glutamyl carboxylase inhibitor, as described herein above, for use in treating or preventing an androgen receptor positive cancer (particularly prostate cancer), wherein the compounds of this drug combination (i.e., the antiandrogen and either the vitamin K antagonist or the γ-glutamyl carboxylase inhibitor, or a pharmaceutical composition comprising these agents) are to be administered in combination with a further anticancer drug and/or in combination with radiotherapy.

The subject or patient to be treated in accordance with the present invention may be an animal (e.g., a non-human animal), a vertebrate animal, a mammal, a rodent (e.g., a guinea pig, a hamster, a rat, or a mouse), a canine (e.g., a dog), a feline (e.g., a cat), a porcine (e.g., a pig), an equine (e.g., a horse), a primate or a simian (e.g., a monkey or an ape, such as a marmoset, a baboon, a gorilla, a chimpanzee, an orangutan, or a gibbon), or a human. In accordance with the present invention, it is envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal; and more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig). Most preferably, the subject/patient to be treated in accordance with the present invention is a human. For the treatment or prevention of prostate cancer, it is most preferred that the subject to be treated is a male human. Furthermore, it is particularly preferred that the subject to be treated in accordance with the present invention (e.g., a human) does not suffer from a thrombotic or thromboembolic disorder. Likewise, it is preferred that the subject to be treated (e.g., a human) has not been diagnosed as suffering from a thrombotic or thromboembolic disorder and/or is not suspected to suffer from a thrombotic or thromboembolic disorder. It is also preferred that the subject to be treated in accordance with the present invention (e.g., a human) does not simultaneously undergo any treatment of a thrombotic or thromboembolic disorder.

The term "treatment" of a disorder or disease as used herein (e.g., "treatment" of an androgen receptor positive cancer or a hyperactive androgen receptor signaling disease/disorder) is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The term "prevention" of a disorder or disease as used herein (e.g., "prevention" of an androgen receptor positive cancer or a hyperactive androgen receptor signaling disease/disorder) is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of the drug combination of the present invention before any clinical and/or pathological symptoms are diagnosed or determined or can be diagnosed or determined by the attending physician.

It is to be understood that the present invention specifically relates to each and every combination of features and embodiments described herein, including any combination of general and/or preferred features/embodiments.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: The CeMM Library of Unique Drugs. (A) Schematic representation of the filtering and clustering procedure leading to the 309 CLOUD drugs. (B) Examples of STEAM drug clusters and selected representative CLOUD drugs. The cluster of dihydrofolate reductase inhibitors centers on methotrexate which was then selected for the CLOUD (top); the two structurally very different histone deacetylase inhibitors are both kept in the CLOUD (bottom). (C) Violations of Lipinski's rule of five by STEAM and CLOUD drugs. (D) Maximum plasma concentration ranges of all CLOUD drugs. (E) Pairwise DIPS scores within 69 STEAM clusters. 58 clusters show median pairwise DIPS score above the overall median DIPS score (grey bars) while only 11 clusters have median DIPS scores below the overall median (diagonally striped bars). (F) List of STEAM and CLOUD drugs. (G) Prodrugs and active forms in the CLOUD.

FIG. 2: The CLOUD compared to other commercial libraries. (A) Heatmap showing drug classes covered by commercially available libraries containing FDA-approved drugs. All commercial libraries together cover 93% of CLOUD drug classes. (B) Heatmap showing active forms of 25 CLOUD prodrugs listed in commercially available libraries. All commercial libraries together cover only 20% of CLOUD active forms.

FIG. 3: STEAM and CLOUD distribution of organisms and targets. Percentage of STEAM and CLOUD drugs for a specific organism (A) or target class (B) are indicated.

Figure 4:
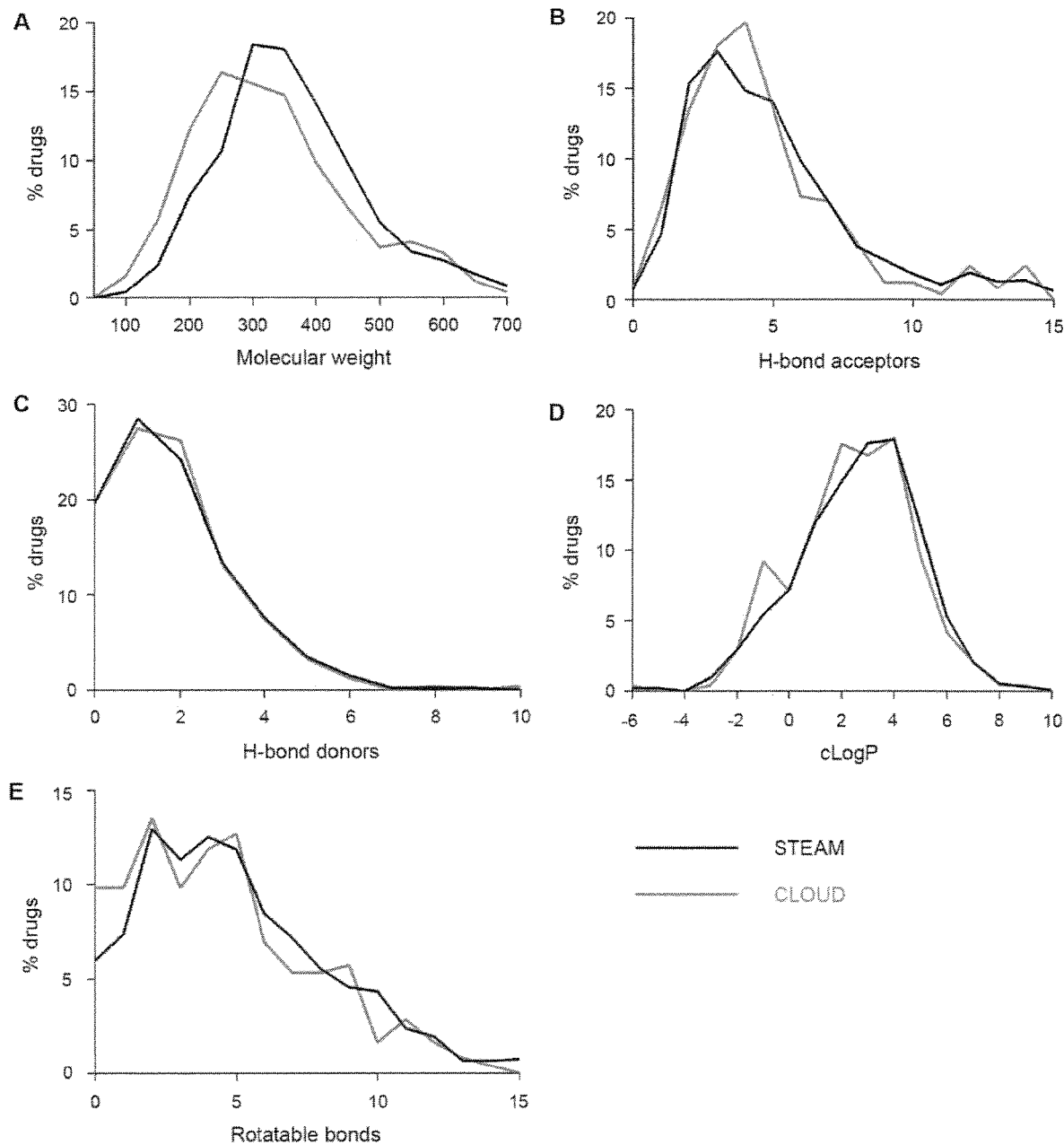

FIG. 4: Physicochemical properties of STEAM and CLOUD drugs. (A-E) Distribution of STEAM and CLOUD drugs physicochemical properties as indicated.

FIG. 5: A combinatorial HTS of the CLOUD uncovers the synergy between flutamide and phenprocoumon (PPC). (A) Butterfly plot summarizing the results from the screen. Dots represent combinations of two CLOUD drugs. The deviation from Bliss independence and the Log of the standard score of the deviation are illustrated. Synergies with a deviation>0.7 (indicated by "+") and antagonisms with a deviation<−0.5 (empty circles) are indicated. The combination of flutamide and PPC is highlighted. (B) Synergies and antagonisms validated in the counter-screen are reported. The top 20 synergies ("+") and antagonisms (empty circles) are indicated. The combination of flutamide and PPC is highlighted. (C) Dose-response matrix of KBM7 cells treated with flutamide and PPC at the indicated concentrations for 3 days. The average fractional inhibition of viability of two biological replicates (left) and deviations from Bliss (right) are reported. The differential volume is the sum of all deviations. (D) RT-qPCR confirming knockout of the AR in the AR KO KBM7 clone. Primers flanking or downstream of the gene-trap were used. Data are normalized to actin expression and KBM7 WT values are set to 1. Error bars are s.d. of three biological replicates. (E) Western blotting confirming knockout of the AR in the AR KO KBM7 clone. Tubulin was used as a loading control. (F) Viability assay showing resistance of the AR KO KBM7 clone to the combination of flutamide and PPC compared to KBM7 WT after 3 days treatment at the indicated concentrations. Error bars are s.d. of two biological replicates.

FIG. 6: Top 20 synergies and antagonisms.

FIG. 7: Screen dose-response matrix for flutamide and phenprocoumon (PPC). Left, dose-response matrix showing fractional inhibition of KMB7 cells viability treated with flutamide and PPC at the indicated concentrations for 3 days. Average of two biological replicates is reported. Right, matrix showing deviations from Bliss. The differential volume is the sum of all deviation values within the matrix.

FIG. 8: AR KO KBM7 clone. (A) Schematic representation of the human AR gene. The gene-trap insertion site is indicated by a cross. The transcriptional start site of the main isoform (exon 1) and AR45 isoform (alternative exon 1B) are also indicated. (B) Ct values showing residual transcription of the main AR and the AR45 isoform in AR KO KBM7 cells.

Figure 10:
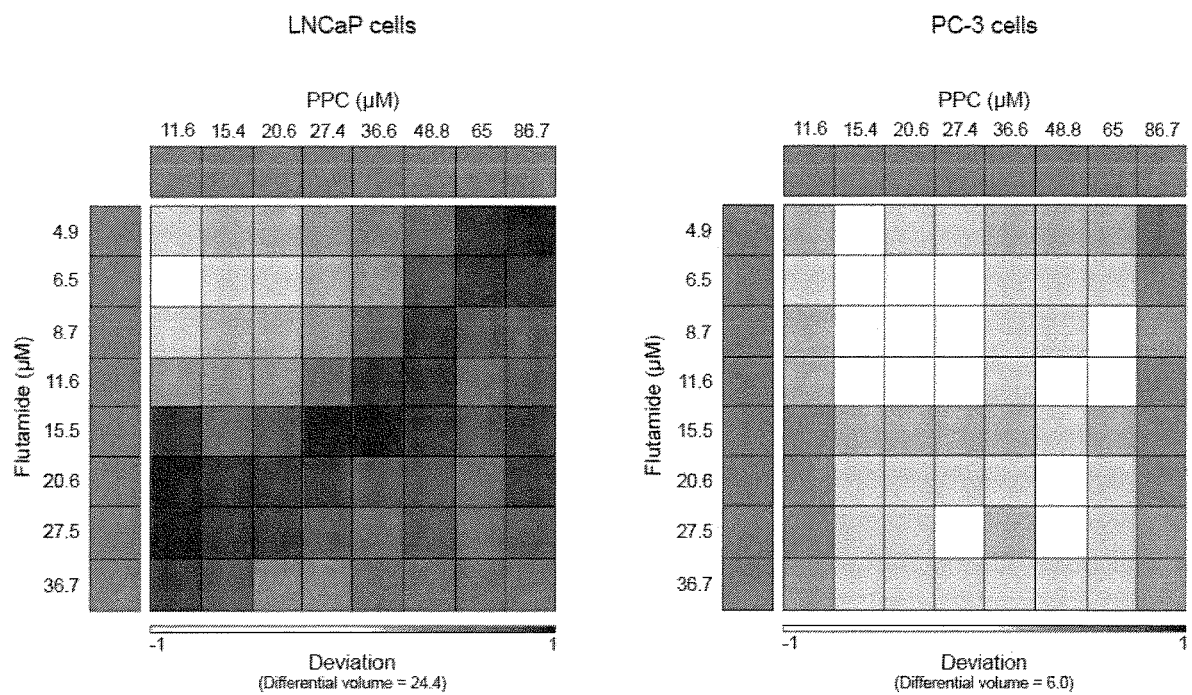

FIG. 9: The combination of flutamide and phenprocoumon (PPC) impairs the growth of LNCaP prostate cancer cells. (A) Dose-response matrix of LNCaP cells (left) and PC-3 cells (right) treated with flutamide and PPC at the indicated concentrations for 3 days. The average fractional inhibition of viability of two biological replicates is reported. The corresponding deviations and differential volumes are illustrated in FIG. 10. (B) Annexin V/propidium iodide staining of LNCaP cells treated with DMSO, 15 µM flutamide, 35 µM PPC or the combination for 3 days. Only the combination of the two drugs induces cellular apoptosis.

FIG. 10: Differential volumes of LNCaP and PC-3. Dose-response matrices showing deviation values and differential volumes of LNCaP cells (left) and PC-3 cells (right) treated with flutamide and phenprocoumon (PPC) at the indicated concentrations for 3 days. Values refer to the fractional inhibition dose-response matrices reported in FIG. 9A.

Figure 11:
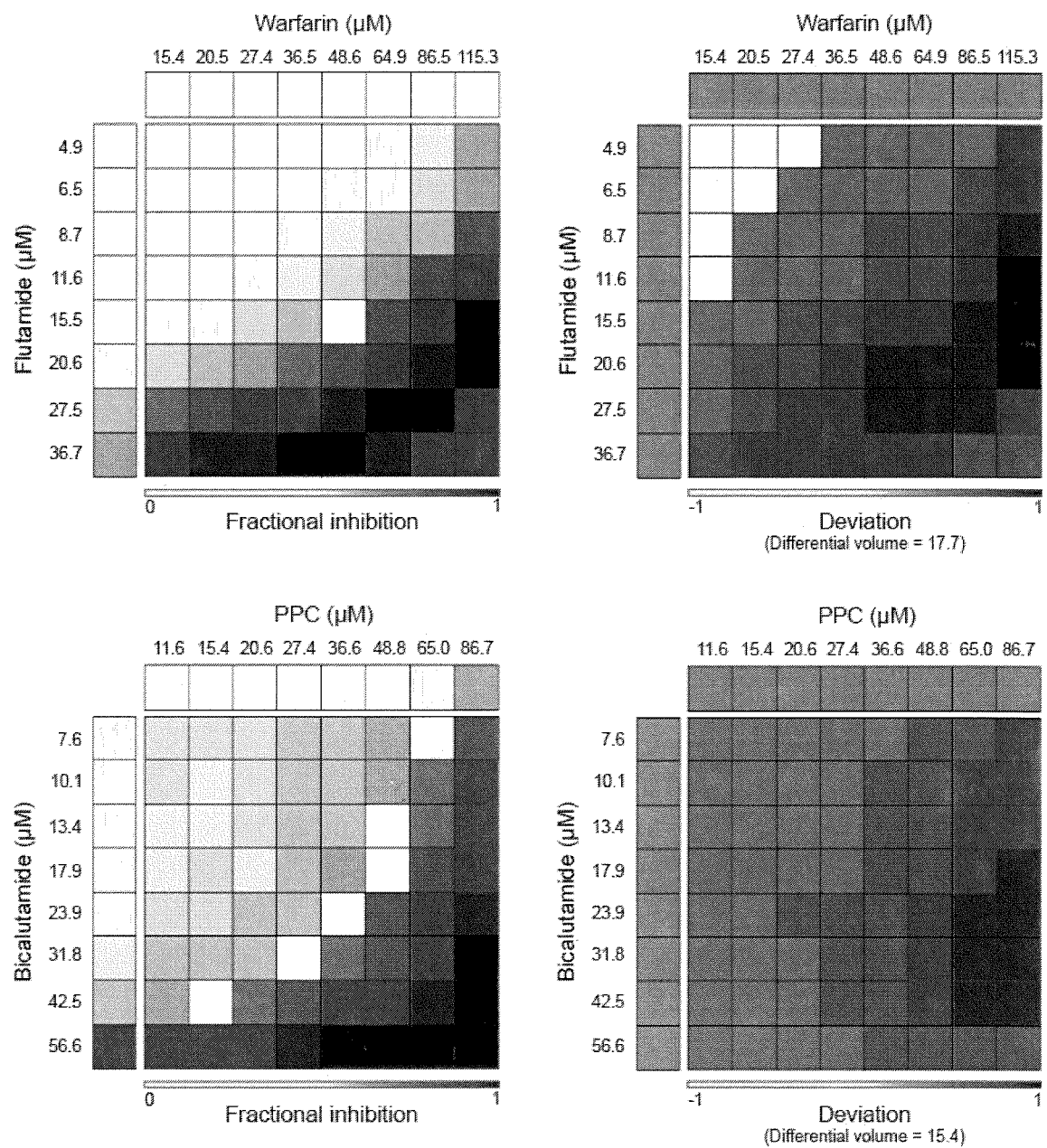
Figure 11:
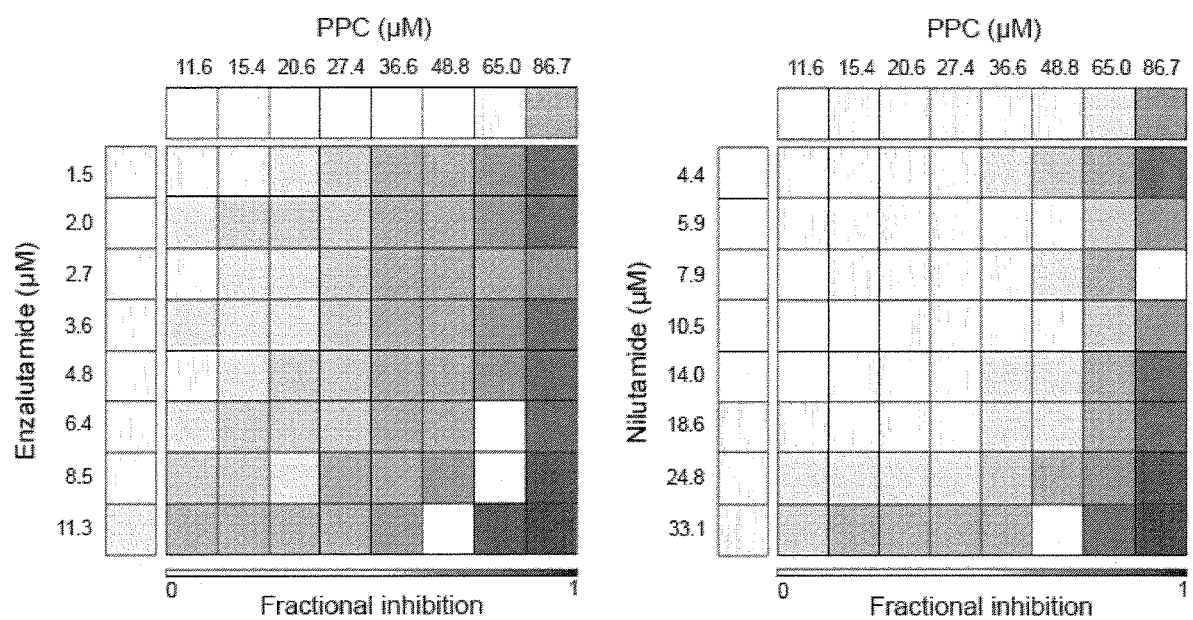

FIG. 11: Dose-response matrices of LNCaP cells treated with different VKORC1 inhibitors and antiandrogens. LNCaP cells were treated with flutamide and warfarin (A) or with phenprocoumon (PPC) in combination with other antiandrogens (A and B) at the indicated concentrations for 3 days.

Figure 12:
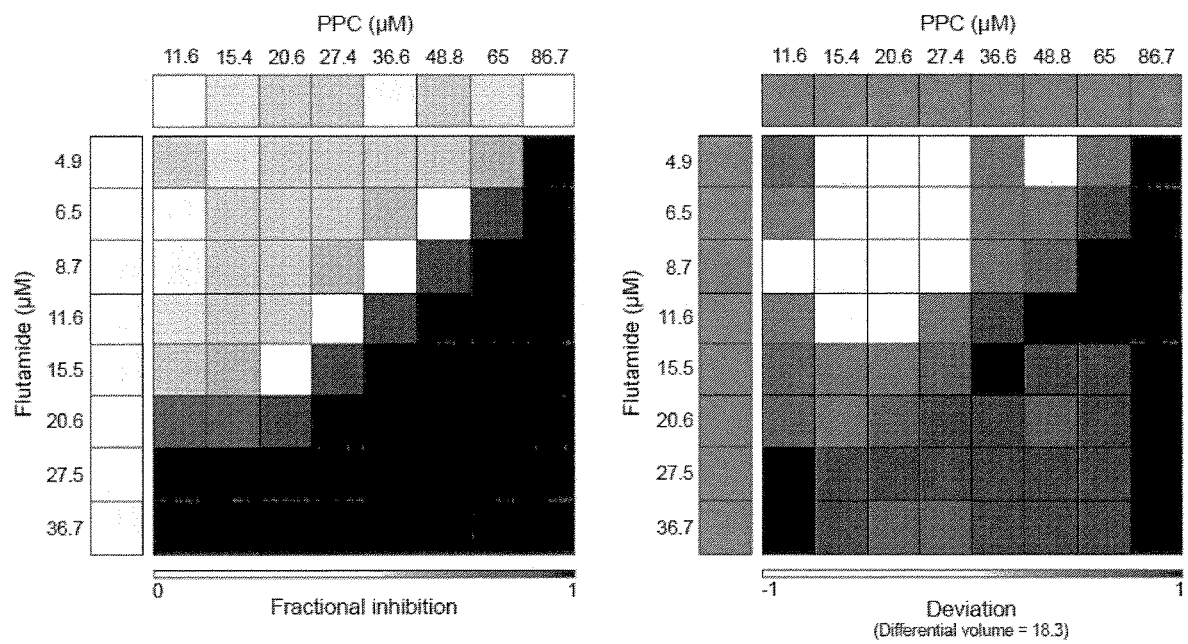

FIG. 12: Dose-response matrix of LNCaP cells in the absence of androgens. LNCaP cells were cultured for 3 days in steroid-deprived medium and then treated with flutamide and phenprocoumon (PPC) at the indicated concentrations for 3 days.

FIG. 13: Antagonistic switch of flutamide in the presence of phenprocoumon (PPC). The combination of flutamide and phenprocoumon induces AR degradation. (A) RT-qPCR analysis of the expression levels of AR and canonical targets of the AR signaling in LNCaP cells cultured in steroid-deprived medium and treated with 15 µM flutamide, 35 µM PPC or the combination for 24 hours. Data are normalized to actin expression and DMSO treatment is set to 1. Error bars are s.d. of three biological replicates. (B) Western blotting of LNCaP cells treated as in (A) showing reduction of AR protein levels in LNCaP cells treated with the combination of flutamide and PPC. GAPDH was used as a loading control. (C) immunofluorescence analysis of LNCaP cells treated with 15 µM flutamide, 35 µM PPC or the combination for 24 hours showing reduced AR protein levels only upon treatment with the combination. Scale bar=100 µm. (D) Cellular thermal shift assay (CETSA) of LNCaP cells treated with either DMSO or 35 µM PPC for 2 days (top) and LNCaP cell lysates treated with either DMSO or 100 µM PPC for 30 min (bottom). (E) RT-qPCR measurements of AR transcript levels in LNCaP cells cultured in steroid-deprived medium and treated with either DMSO or the combination of flutamide and phenprocoumon (PPC). After 24 hours, 4 µM Actinomycin D was added to the medium and samples were harvested at the indicated time points. Data are normalized to actin expression and to the initial time point. Error bars are s.d. of three biological replicates. (F) Western blotting of LNCaP cells treated with 30 nM bortezomib, 15 µM flutamide, 35 µM PPC as indicated. GAPDH was used as a loading control. (G) Western blotting of LNCaP cells treated with either DMSO (top) or the combination of flutamide and phenprocoumon (PPC) (bottom). After 24 hours, 2.5 µg/ml cycloheximide was added the medium and samples were harvested at the indicated time points. GAPDH was used as a loading control. (H) 2D difference gel electrophoresis (DIGE) of AR immunoprecipitated from LNCaP cells treated with DMSO (top panel) or phenprocoumon (PPC) (bottom panel). (I) Western blotting for global γ-carboxylation in LNCaP cells treated with increasing concentrations of vitamin K. (J) Immunoprecipitation of γ-carboxylated AR from LNCaP lysates treated with increasing amounts of phenprocoumon (PPC). (K) MS/MS spectrum of the methylated γ-carboxylated AR(1-9) peptide derived from LNCaP cells treated with vitamin K.

FIG. 14: Androgen receptor (AR) and AR canonical targets downregulation. (A) RT-qPCR experiment showing restrained expression of KLK3 and KLK2 as well as downregulation of AR in LNCaP cells treated with 15 µM flutamide and 35 µM PPC for 8 hours. (B) Western blotting experiment showing downregulation of the AR in LNCaP cells treated with 15 µM flutamide and 35 µM PPC for 8 hours.

Figure 15:
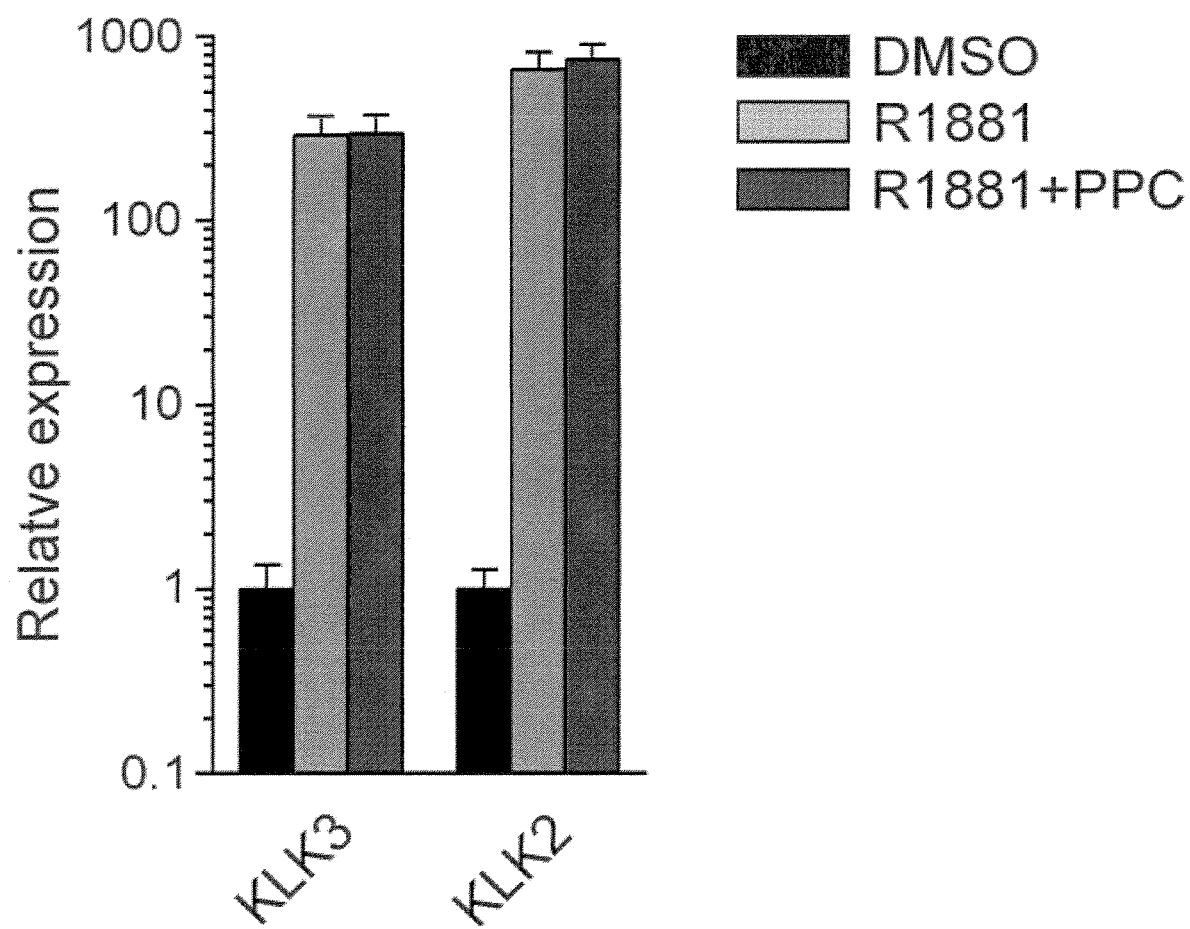

FIG. 15: Androgen receptor (AR) signaling activation by R1881. RT-qPCR experiment showing unaltered expression of KLK3 and KLK2 in LNCaP cells treated with 10 nM R1881±35 µM phenprocoumon (PPC) for 24 hours.

The present invention particularly relates to the following items:

1. An antiandrogen for use in treating or preventing an androgen receptor positive cancer or a hyperactive androgen receptor signaling disease/disorder, wherein the antiandrogen is to be administered in combination with a vitamin K antagonist or a γ-glutamyl carboxylase inhibitor.
2. A vitamin K antagonist for use in treating or preventing an androgen receptor positive cancer or a hyperactive androgen receptor signaling disease/disorder, wherein the vitamin K antagonist is to be administered in combination with an antiandrogen.
3. A γ-glutamyl carboxylase inhibitor for use in treating or preventing an androgen receptor positive cancer or a hyperactive androgen receptor signaling disease/disorder, wherein the γ-glutamyl carboxylase inhibitor is to be administered in combination with an antiandrogen.
4. A combination of (i) an antiandrogen and (ii) a vitamin K antagonist or a γ-glutamyl carboxylase inhibitor, for use in treating or preventing an androgen receptor positive cancer or a hyperactive androgen receptor signaling disease/disorder.
5. A pharmaceutical composition comprising: an antiandrogen; a vitamin K antagonist or a γ-glutamyl carboxylase inhibitor; and a pharmaceutically acceptable excipient.
6. The pharmaceutical composition of item 5 for use in treating or preventing an androgen receptor positive cancer or a hyperactive androgen receptor signaling disease/disorder.
7. The antiandrogen for use according to item 1 or the vitamin K antagonist for use according to item 2 or the γ-glutamyl carboxylase inhibitor for use according to item 3 or the combination for use according to item 4 or the pharmaceutical composition for use according to item 6, wherein said use is in treating or preventing an androgen receptor positive cancer.
8. The antiandrogen for use according to item 1 or 7 or the vitamin K antagonist for use according to item 2 or 7 or the γ-glutamyl carboxylase inhibitor for use according to item 3 or 7 or the combination for use according to item 4 or 7 or the pharmaceutical composition for use according to item 6 or 7, wherein said androgen receptor positive cancer is selected from prostate cancer, breast cancer, endometrial cancer, liver cancer, laryngeal cancer, osteosarcoma, glioblastoma, chondrosarcoma, Ewing's sarcoma, and testicular cancer.
9. The antiandrogen for use according to item 1 or 7 or the vitamin K antagonist for use according to item 2 or 7 or the γ-glutamyl carboxylase inhibitor for use according to item 3 or 7 or the combination for use according to item 4 or 7 or the pharmaceutical composition for use according to item 6 or 7, wherein said androgen receptor positive cancer is prostate cancer.

10. The antiandrogen for use according to any one of items 1 or 7 to 9 or the vitamin K antagonist for use according to any one of items 2 or 7 to 9 or the γ-glutamyl carboxylase inhibitor for use according to any one of items 3 or 7 to 9 or the combination for use according to any one of items 4 or 7 to 9 or the pharmaceutical composition for use according to any one of items 6 to 9, wherein said androgen receptor positive cancer is an antiandrogen-resistant prostate cancer.

11. The antiandrogen for use according to any one of items 8 to 10 or the vitamin K antagonist for use according to any one of items 8 to 10 or the γ-glutamyl carboxylase inhibitor for use according to any one of items 8 to 10 or the combination for use according to any one of items 8 to 10 or the pharmaceutical composition for use according to any one of items 8 to 10, wherein said prostate cancer has one or more androgen receptor mutations selected from an androgen receptor T877A mutation, an androgen receptor T877S mutation, an androgen receptor W741C mutation, an androgen receptor F876L mutation, and an androgen receptor H874Y mutation.

12. The antiandrogen for use according to item 11 or the vitamin K antagonist for use according to item 11 or the γ-glutamyl carboxylase inhibitor for use according to item 11 or the combination for use according to item 11 or the pharmaceutical composition for use according to item 11, wherein said prostate cancer has an androgen receptor T877A mutation.

13. A vitamin K antagonist for use in resensitizing an antiandrogen-resistant prostate cancer to the treatment with an antiandrogen.

14. A γ-glutamyl carboxylase inhibitor for use in resensitizing an antiandrogen-resistant prostate cancer to the treatment with an antiandrogen.

15. The vitamin K antagonist for use according to item 13 or the γ-glutamyl carboxylase inhibitor for use according to item 14, wherein said prostate cancer has one or more androgen receptor mutations selected from an androgen receptor T877A mutation, an androgen receptor T877S mutation, an androgen receptor W741C mutation, an androgen receptor F876L mutation, and an androgen receptor H874Y mutation.

16. The vitamin K antagonist for use according to item 15 or the γ-glutamyl carboxylase inhibitor for use according to item 15, wherein said prostate cancer has an androgen receptor T877A mutation.

17. The antiandrogen for use according to item 1 or the vitamin K antagonist for use according to item 2 or the γ-glutamyl carboxylase inhibitor for use according to item 3 or the combination for use according to item 4 or the pharmaceutical composition for use according to item 6, wherein said use is in treating or preventing a hyperactive androgen receptor signaling disease/disorder.

18. The antiandrogen for use according to item 1 or 17 or the vitamin K antagonist for use according to item 2 or 17 or the γ-glutamyl carboxylase inhibitor for use according to item 3 or 17 or the combination for use according to item 4 or 17 or the pharmaceutical composition for use according to item 6 or 17, wherein said hyperactive androgen receptor signaling disease/disorder is selected from hyperandrogenism, spinal-bulbar muscular atrophy, benign prostatic hyperplasia, hypersexuality, paraphilia, acne, seborrhea, hirsutism, androgenic alopecia, hidradenitis suppurativa, and polycystic ovary syndrome.

19. The antiandrogen for use according to any one of items 1, 17 or 18 or the vitamin K antagonist for use according to any one of items 2, 17 or 18 or the γ-glutamyl carboxylase inhibitor for use according to any one of items 3, 17 or 18 or the combination for use according to any one of items 4, 17 or 18 or the pharmaceutical composition for use according to any one of items 6, 17 or 18, wherein the subject to be treated expresses mutant androgen receptor having one or more mutations selected from an androgen receptor T877A mutation, an androgen receptor 1877S mutation, an androgen receptor W741C mutation, an androgen receptor F876L mutation, and an androgen receptor H874Y mutation.

20. The antiandrogen for use according to item 19 or the vitamin K antagonist for use according to item 19 or the γ-glutamyl carboxylase inhibitor for use according to item 19 or the combination for use according to item 19 or the pharmaceutical composition for use according to item 19, wherein the subject to be treated expresses mutant androgen receptor having an androgen receptor T877A mutation.

21. The antiandrogen for use according to any one of items 1, 7 to 12 or 17 to 20 or the vitamin K antagonist for use according to any one of items 2, 7 to 13 or 15 to 20 or the γ-glutamyl carboxylase inhibitor for use according to any one of items 3, 7 to 12 or 14 to 20 or the combination for use according to any one of items 4, 7 to 12 or 17 to 20 or the pharmaceutical composition of item 5 or the pharmaceutical composition for use according to any one of items 6 to 12 or 17 to 20, wherein the antiandrogen is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, chlormadinone acetate, delanterone, dienogest, drospirenone, epitestosterone, inocoterone, metogest, nomegestrol, nomegestrol acetate, nordinone, norgestimate, osaterone, oxendolone, rosterolone, topterone, zanoterone, RU-58642, RU-58841, and a pharmaceutically acceptable salt or solvate of any one of these agents.

22. The antiandrogen for use according to item 21 or the vitamin K antagonist for use according to item 21 or the γ-glutamyl carboxylase inhibitor for use according to item 21 or the combination for use according to item 21 or the pharmaceutical composition of item 5 or the pharmaceutical composition for use according to item 21, wherein the antiandrogen is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, and a pharmaceutically acceptable salt or solvate of any one of these agents.

23. The antiandrogen for use according to item 21 or the vitamin K antagonist for use according to item 21 or the γ-glutamyl carboxylase inhibitor for use according to item 21 or the combination for use according to item 21 or the pharmaceutical composition of item 5 or the pharmaceutical composition for use according to item 21, wherein the antiandrogen is selected from flutamide, nilutamide, bicalutamide, enzalutamide, 2-hydroxyflutamide, BMS-641988, and ARN-509.

24. The antiandrogen for use according to item 21 or the vitamin K antagonist for use according to item 21 or the γ-glutamyl carboxylase inhibitor for use according to item 21 or the combination for use according to item 21 or the pharmaceutical composition of item 5 or the pharmaceutical composition for use according to item 21, wherein the antiandrogen is flutamide.

25. The antiandrogen for use according to any one of items 1, 7 to 12 or 17 to 24 or the vitamin K antagonist for use according to any one of items 2, 7 to 13 or 15 to 24 or the combination for use according to any one of items 4, 7 to 12 or 17 to 24 or the pharmaceutical composition of item 5 or the pharmaceutical composition for use according to any one of items 6 to 12 or 17 to 24, wherein the vitamin K antagonist is selected from phenprocoumon, dicoumarol, acenocoumarol, warfarin, ethyl biscoumacetate, anisindione, phenindione, clorindione, fluindione, 1-N-methyl-5-thiotetrazole, 5,5'-dithiobis(1-methyltetrazole), disulfiram, and N-ethylmaleimide.

26. The antiandrogen for use according to item 25 or the vitamin K antagonist for use according to item 25 or the combination for use according to item 25 or the pharmaceutical composition of item 5 or the pharmaceutical composition for use according to item 25, wherein the vitamin K antagonist is phenprocoumon.

27. The antiandrogen for use according to item 25 or the vitamin K antagonist for use according to item 25 or the combination for use according to item 25 or the pharmaceutical composition of item 5 or the pharmaceutical composition for use according to item 25, wherein the vitamin K antagonist is warfarin.

28. The antiandrogen for use according to any one of items 1, 7 to 12 or 17 to 24 or the γ-glutamyl carboxylase inhibitor for use according to any one of items 3, 7 to 12 or 14 to 24 or the combination for use according to any one of items 4, 7 to 12 or 17 to 24 or the pharmaceutical composition of item 5 or the pharmaceutical composition for use according to any one of items 6 to 12 or 17 to 24, wherein the γ-glutamyl carboxylase inhibitor is calumenin.

29. The antiandrogen for use according to any one of items 1, 7 to 12 or 17 to 27, wherein the antiandrogen is to be administered in combination with the vitamin K antagonist.

30. The combination for use according to any one of items 4, 7 to 12 or 17 to 27, wherein the combination is a combination of the antiandrogen and the vitamin K antagonist.

31. The pharmaceutical composition of any one of items 5 or 21 to 27 or the pharmaceutical composition for use according to any one of items 6 to 12 or 17 to 27, wherein the pharmaceutical composition comprises the antiandrogen, the vitamin K antagonist, and the pharmaceutically acceptable excipient.

32. The antiandrogen for use according to any one of items 1, 7 to 12, 17 to 27 or 29 or the vitamin K antagonist for use according to any one of items 2, 7 to 13 or 15 to 27 or the combination for use according to any one of items 4, 7 to 12, 17 to 27 or 30, wherein the antiandrogen and the vitamin K antagonist are provided in a single pharmaceutical formulation.

33. The antiandrogen for use according to any one of items 1, 7 to 12, 17 to 27 or 29 or the vitamin K antagonist for use according to any one of items 2, 7 to 13 or 15 to 27 or the combination for use according to any one of items 4, 7 to 12, 17 to 27 or 30, wherein the antiandrogen and the vitamin K antagonist are provided in separate pharmaceutical formulations.

34. The antiandrogen for use according to item 32 or 33 or the vitamin K antagonist for use according to item 32 or 33 or the combination for use according to item 32 or 33, wherein the antiandrogen and the vitamin K antagonist are to be administered simultaneously.

35. The antiandrogen for use according to item 33 or the vitamin K antagonist for use according to item 33 or the combination for use according to item 33, wherein the antiandrogen and the vitamin K antagonist are to be administered sequentially.

36. The antiandrogen for use according to any one of items 1, 7 to 12, 17 to 24 or 28 or the γ-glutamyl carboxylase inhibitor for use according to any one of items 3, 7 to 12, 14 to 24 or 28 or the combination for use according to any one of items 4, 7 to 12, 17 to 24 or 28, wherein the antiandrogen and the γ-glutamyl carboxylase inhibitor are to be administered simultaneously, either in a single pharmaceutical formulation or in separate pharmaceutical formulations.

37. The antiandrogen for use according to any one of items 1, 7 to 12, 17 to 24 or 28 or the γ-glutamyl carboxylase inhibitor for use according to any one of items 3, 7 to 12, 14 to 24 or 28 or the combination for use according to any one of items 4, 7 to 12, 17 to 24 or 28, wherein the antiandrogen and the γ-glutamyl carboxylase inhibitor are to be administered sequentially in separate pharmaceutical formulations.

38. The antiandrogen for use according to any one of items 1, 7 to 12, 17 to 29 or 32 to 37 or the vitamin K antagonist for use according to any one of items 2, 7 to 13, 15 to 27 or 32 to 35 or the γ-glutamyl carboxylase inhibitor for use according to any one of items 3, 7 to 12, 14 to 24, 28, 36 or 37 or the combination for use according to any one of items 4, 7 to 12, 17 to 28, 30 or 32 to 37 or the pharmaceutical composition for use according to any one of items 6 to 12, 17 to 28 or 31, wherein the antiandrogen and either the vitamin K antagonist or the γ-glutamyl carboxylase inhibitor, or the pharmaceutical composition comprising the antiandrogen and either the vitamin K antagonist or the γ-glutamyl carboxylase inhibitor, are/is to be administered orally.

39. The antiandrogen for use according to any one of items 1, 7 to 12, 21 to 29 or 32 to 38 or the vitamin K antagonist for use according to any one of items 2, 7 to 13, 15, 16, 21 to 27, 32 to 35 or 38 or the γ-glutamyl carboxylase inhibitor for use according to any one of items 3, 7 to 12, 14 to 16, 21 to 24, 28 or 36 to 38 or the combination for use according to any one of items 4, 7 to 12, 21 to 28, 30 or 32 to 38 or the pharmaceutical composition for use according to any one of items 6 to 12, 21 to 28, 31 or 38, wherein the antiandrogen and either the vitamin K antagonist or the γ-glutamyl carboxylase inhibitor, or the pharmaceutical composition comprising the antiandrogen and either the vitamin K antagonist or the γ-glutamyl carboxylase inhibitor, are/is to be administered in combination with a further anticancer drug and/or in combination with radiotherapy.

40. The antiandrogen for use according to any one of items 1, 7 to 12, 17 to 29 or 32 to 39 or the vitamin K antagonist for use according to any one of items 2, 7 to 13, 15 to 27, 32 to 35, 38 or 39 or the γ-glutamyl carboxylase inhibitor for use according to any one of items 3, 7 to 12, 14 to 24, 28 or 36 to 39 or the combination for use according to any one of items 4, 7 to 12, 17 to 28, 30 or 32 to 39 or the pharmaceutical composition for use according to any one of items 6 to 12, 17 to 28, 31, 38 or 39, wherein the subject to be treated is a human.

41. The antiandrogen for use according to any one of items 1, 7 to 12, 17 to 29 or 32 to 40 or the vitamin K antagonist for use according to any one of items 2, 7 to 13, 15 to 27, 32 to 35 or 38 to 40 or the γ-glutamyl carboxylase inhibitor for use according to any one of items 3, 7 to 12, 14 to 24, 28 or 36 to 40 or the combination for use according to any one of items 4, 7 to 12, 17 to 28, 30 or 32 to 40 or the pharmaceutical composition for use according to any one of items 6 to 12, 17 to 28, 31 or 38 to 40, wherein the subject to be treated does not suffer from a thrombotic or thromboembolic disorder.

42. Use of an antiandrogen for the preparation of a medicament for treating or preventing an androgen receptor positive cancer or a hyperactive androgen receptor signaling disease/disorder, wherein the antiandrogen is to be administered in combination with a vitamin K antagonist or a γ-glutamyl carboxylase inhibitor.

43. Use of a vitamin K antagonist for the preparation of a medicament for treating or preventing an androgen receptor positive cancer or a hyperactive androgen receptor signaling disease/disorder, wherein the vitamin K antagonist is to be administered in combination with an antiandrogen.

44. Use of a γ-glutamyl carboxylase inhibitor for the preparation of a medicament for treating or preventing an androgen receptor positive cancer or a hyperactive androgen receptor signaling disease/disorder, wherein the γ-glutamyl carboxylase inhibitor is to be administered in combination with an antiandrogen.

45. Use of a combination of (i) an antiandrogen and (ii) a vitamin K antagonist or a γ-glutamyl carboxylase inhibitor, for the preparation of a medicament for treating or preventing an androgen receptor positive cancer or a hyperactive androgen receptor signaling disease/disorder.

46. The use of any one of items 42 to 45, wherein said medicament is for treating or preventing an androgen receptor positive cancer.

47. The use of any one of items 42 to 46, wherein said androgen receptor positive cancer is selected from prostate cancer, breast cancer, endometrial cancer, liver cancer, laryngeal cancer, osteosarcoma, glioblastoma, chondrosarcoma, Ewing's sarcoma, and testicular cancer.

48. The use of any one of items 42 to 46, wherein said androgen receptor positive cancer is prostate cancer.

49. The use of any one of items 42 to 48, wherein said androgen receptor positive cancer is an antiandrogen-resistant prostate cancer.

50. The use of any one of items 47 to 49, wherein said prostate cancer has one or more androgen receptor mutations selected from an androgen receptor T877A mutation, an androgen receptor T877S mutation, an androgen receptor W741C mutation, an androgen receptor F876L mutation, and an androgen receptor H874Y mutation.

51. The use of item 50, wherein said prostate cancer has an androgen receptor T877A mutation.

52. Use of a vitamin K antagonist for the preparation of a medicament for resensitizing an antiandrogen-resistant prostate cancer to the treatment with an antiandrogen.

53. Use of a γ-glutamyl carboxylase inhibitor for the preparation of a medicament for resensitizing an antiandrogen-resistant prostate cancer to the treatment with an antiandrogen.

54. The use of item 52 or 53, wherein said prostate cancer has one or more androgen receptor mutations selected from an androgen receptor T877A mutation, an androgen receptor T877S mutation, an androgen receptor W741C mutation, an androgen receptor F876L mutation, and an androgen receptor H874Y mutation.

55. The use of item 54, wherein said prostate cancer has an androgen receptor T877A mutation.

56. The use of any one of items 42 to 45, wherein said medicament is for treating or preventing a hyperactive androgen receptor signaling disease/disorder.

57. The use of any one of items 42 to 45 or 56, wherein said hyperactive androgen receptor signaling disease/disorder is selected from hyperandrogenism, spinal-bulbar muscular atrophy, benign prostatic hyperplasia, hypersexuality, paraphilia, acne, seborrhea, hirsutism, androgenic alopecia, hidradenitis suppurativa, and polycystic ovary syndrome.

58. The use of any one of items 42 to 45, 56 or 57, wherein the subject to be treated expresses mutant androgen receptor having one or more mutations selected from an androgen receptor T877A mutation, an androgen receptor T877S mutation, an androgen receptor W741C mutation, an androgen receptor F876L mutation, and an androgen receptor H874Y mutation.

59. The use of item 58, wherein the subject to be treated expresses mutant androgen receptor having an androgen receptor T877A mutation.

60. The use of any one of items 42 to 59, wherein the antiandrogen is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, chlormadinone acetate, delanterone, dienogest, drospirenone, epitestosterone, inocoterone, metogest, nomegestrol, nomegestrol acetate, nordinone, norgestimate, osaterone, oxendolone, rosterolone, topterone, zanoterone, RU-58642, RU-58841, and a pharmaceutically acceptable salt or solvate of any one of these agents.

61. The use of item 60, wherein the antiandrogen is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, and a pharmaceutically acceptable salt or solvate of any one of these agents.

62. The use of item 60, wherein the antiandrogen is selected from flutamide, nilutamide, bicalutamide, enzalutamide, 2-hydroxyflutamide, BMS-641988, and ARN-509.

63. The use of item 60, wherein the antiandrogen is flutamide.

64. The use of any one of items 42, 43, 45 to 52 or 54 to 63, wherein the vitamin K antagonist is selected from phenprocoumon, dicoumarol, acenocoumarol, warfarin, ethyl biscoumacetate, anisindione, phenindione, clorindione, fluindione, 1-N-methyl-5-thiotetrazole, 5,5'-dithiobis(1-methyltetrazole), disulfiram, and N-ethylmaleimide.

65. The use of item 64, wherein the vitamin K antagonist is phenprocoumon.

66. The use of item 64, wherein the vitamin K antagonist is warfarin.

67. The use of any one of items 42, 44 to 51 or 53 to 63, wherein the γ-glutamyl carboxylase inhibitor is calumenin.

68. The use of any one of items 42, 45 to 51 or 56 to 66, wherein the antiandrogen is to be administered in combination with the vitamin K antagonist.

69. The use of any one of items 45 to 51 or 56 to 66, wherein the combination is a combination of the antiandrogen and the vitamin K antagonist.

70. The use of any one of items 42, 43, 45 to 51, 56 to 66, 68 or 69, wherein the antiandrogen and the vitamin K antagonist are provided in a single pharmaceutical formulation.

71. The use of any one of items 42, 43, 45 to 51, 56 to 66, 68 or 69, wherein the antiandrogen and the vitamin K antagonist are provided in separate pharmaceutical formulations.
72. The use of item 70 or 71, wherein the antiandrogen and the vitamin K antagonist are to be administered simultaneously.
73. The use of item 71, wherein the antiandrogen and the vitamin K antagonist are to be administered sequentially.
74. The use of any one of items 42, 44 to 51, 56 to 63 or 67, wherein the antiandrogen and the γ-glutamyl carboxylase inhibitor are to be administered simultaneously, either in a single pharmaceutical formulation or in separate pharmaceutical formulations.
75. The use of any one of items 42, 44 to 51, 56 to 63 or 67, wherein the antiandrogen and the γ-glutamyl carboxylase inhibitor are to be administered sequentially in separate pharmaceutical formulations.
76. The use of any one of items 42 to 75, wherein the antiandrogen and either the vitamin K antagonist or the γ-glutamyl carboxylase inhibitor are to be administered orally.
77. The use of any one of items 42 to 76, wherein the antiandrogen and either the vitamin K antagonist or the γ-glutamyl carboxylase inhibitor are to be administered in combination with a further anticancer drug and/or in combination with radiotherapy.
78. The use of any one of items 42 to 77, wherein the subject to be treated is a human.
79. The use of any one of items 42 to 78, wherein the subject to be treated does not suffer from a thrombotic or thromboembolic disorder.
80. A method of treating an androgen receptor positive cancer or a hyperactive androgen receptor signaling disease/disorder, the method comprising administering an antiandrogen in combination with a vitamin K antagonist or with a γ-glutamyl carboxylase inhibitor to a subject in need thereof.
81. The method of item 80, wherein said method comprises administering an antiandrogen in combination with a vitamin K antagonist to a subject in need thereof.
82. The method of item 80, wherein said method comprises administering an antiandrogen in combination with a γ-glutamyl carboxylase inhibitor to a subject in need thereof.
83. The method of item 80, which is a method of treating an androgen receptor positive cancer.
84. The method of item 83, wherein said androgen receptor positive cancer is selected from prostate cancer, breast cancer, endometrial cancer, liver cancer, laryngeal cancer, osteosarcoma, glioblastoma, chondrosarcoma, Ewing's sarcoma, and testicular cancer.
85. The method of item 83, wherein said androgen receptor positive cancer is prostate cancer.
86. The method of item 83, wherein said androgen receptor positive cancer is an antiandrogen-resistant prostate cancer.
87. The method of item 86, wherein said prostate cancer has one or more androgen receptor mutations selected from an androgen receptor T877A mutation, an androgen receptor T877S mutation, an androgen receptor W741C mutation, an androgen receptor F876L mutation, and an androgen receptor H874Y mutation.
88. The method of item 86, wherein said prostate cancer has an androgen receptor T877A mutation.
89. The method of item 80, which is a method of treating or preventing a hyperactive androgen receptor signaling disease/disorder.
90. The method of item 89, wherein said hyperactive androgen receptor signaling disease/disorder is selected from hyperandrogenism, spinal-bulbar muscular atrophy, benign prostatic hyperplasia, hypersexuality, paraphilia, acne, seborrhea, hirsutism, androgenic alopecia, hidradenitis suppurativa, and polycystic ovary syndrome.
91. The method of item 90, wherein the subject to be treated expresses mutant androgen receptor having one or more mutations selected from an androgen receptor T877A mutation, an androgen receptor T877S mutation, an androgen receptor W741C mutation, an androgen receptor F876L mutation, and an androgen receptor H874Y mutation.
92. The method of item 90, wherein the subject to be treated expresses mutant androgen receptor having an androgen receptor T877A mutation.
93. The method of item 80, wherein the antiandrogen is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, chlormadinone acetate, delanterone, dienogest, drospirenone, epitestosterone, inocoterone, metogest, nomegestrol, nomegestrol acetate, nordinone, norgestimate, osaterone, oxendolone, rosterolone, topterone, zanoterone, RU-58642, RU-58841, and a pharmaceutically acceptable salt or solvate of any one of these agents.
94. The method of item 80, wherein the antiandrogen is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, and a pharmaceutically acceptable salt or solvate of any one of these agents.
95. The method of item 80, wherein the antiandrogen is selected from flutamide, nilutamide, bicalutamide, enzalutamide, 2-hydroxyflutamide, BMS-641988, and ARN-509.
96. The method of item 80, wherein the antiandrogen is flutamide.
97. The method of item 80, wherein the vitamin K antagonist is selected from phenprocoumon, dicoumarol, acenocoumarol, warfarin, ethyl biscoumacetate, anisindione, phenindione, clorindione, fluindione, 1-N-methyl-5-thiotetrazole, 5,5'-dithiobis(1-methyltetrazole), disulfiram, and N-ethylmaleimide.
98. The method of item 80, wherein the vitamin K antagonist is phenprocoumon.
99. The method of item 80, wherein the vitamin K antagonist is warfarin.
100. The method of item 80, wherein the γ-glutamyl carboxylase inhibitor is calumenin.
101. The method of item 81, wherein the antiandrogen and the vitamin K antagonist are provided in a single pharmaceutical formulation.
102. The method of item 81, wherein the antiandrogen and the vitamin K antagonist are provided in separate pharmaceutical formulations.
103. The method of item 101, wherein the antiandrogen and the vitamin K antagonist are to be administered simultaneously.

104. The method of item 102, wherein the antiandrogen and the vitamin K antagonist are to be administered simultaneously.

105. The method of item 102, wherein the antiandrogen and the vitamin K antagonist are to be administered sequentially.

106. The method of item 82, wherein the antiandrogen and the γ-glutamyl carboxylase inhibitor are to be administered simultaneously, either in a single pharmaceutical formulation or in separate pharmaceutical formulations.

107. The method of item 82, wherein the antiandrogen and the γ-glutamyl carboxylase inhibitor are to be administered sequentially in separate pharmaceutical formulations.

108. The method of item 80, wherein the antiandrogen and either the vitamin K antagonist or the γ-glutamyl carboxylase inhibitor are administered orally.

109. The method of item 80, wherein the antiandrogen and either the vitamin K antagonist or the γ-glutamyl carboxylase inhibitor are administered in combination with a further anticancer drug and/or in combination with radiotherapy.

110. The method of item 80, wherein the subject is a human.

111. The method of item 80, wherein the subject does not suffer from a thrombotic or thromboembolic disorder.

112. A method of resensitizing an antiandrogen-resistant prostate cancer to the treatment with an antiandrogen, the method comprising administering a vitamin K antagonist or a γ-glutamyl carboxylase inhibitor to a subject in need thereof.

113. The method of item 112, wherein said method comprises administering a vitamin K antagonist to a subject in need thereof.

114. The method of item 112, wherein said method comprises administering a γ-glutamyl carboxylase inhibitor to a subject in need thereof.

115. The method of item 112, wherein said prostate cancer has one or more androgen receptor mutations selected from an androgen receptor T877A mutation, an androgen receptor T877S mutation, an androgen receptor W7410 mutation, an androgen receptor F876L mutation, and an androgen receptor H874Y mutation.

116. The method of item 112, wherein said prostate cancer has an androgen receptor T877A mutation.

117. The method of item 112, wherein said antiandrogen is selected from flutamide, nilutamide, bicalutamide, enzalutamide, 2-hydroxyflutamide, BMS-641988, ARN-509, ketoconazole, PF-998425, R2956, cyproterone, cyproterone acetate, benorterone, galeterone, megestrol acetate, mifepristone, chlormadinone acetate, delanterone, dienogest, drospirenone, epitestosterone, inocoterone, metogest, nomegestrol, nomegestrol acetate, nordinone, norgestimate, osaterone, oxendolone, rosterolone, topterone, zanoterone, RU-58642, RU-58841, and a pharmaceutically acceptable salt or solvate of any one of these agents.

118. The method of item 112, wherein the antiandrogen is selected from flutamide, nilutamide, bicalutamide, enzalutamide, 2-hydroxyflutamide, BMS-641988, ARN-509, ketoconazole, PF-998425, 82956, cyproterone, cyproterone acetate, benorterone, galeterone, megestrol acetate, mifepristone, and a pharmaceutically acceptable salt or solvate of any one of these agents.

119. The method of item 112, wherein the antiandrogen is selected from flutamide, nilutamide, bicalutamide, enzalutamide, 2-hydroxyflutamide, BMS-641988, and ARN-509.

120. The method of item 112, wherein the antiandrogen is flutamide.

121. The method of item 112, wherein the vitamin K antagonist is selected from phenprocoumon, dicoumarol, acenocoumarol, warfarin, ethyl biscoumacetate, anisindione, phenindione, clorindione, fluindione, 1-N-methyl-5-thiotetrazole, 5,5'-dithiobis(1-methyltetrazole), disulfiram, and N-ethylmaleimide.

122. The method of item 112, wherein the vitamin K antagonist is phenprocoumon.

123. The method of item 112, wherein the vitamin K antagonist is warfarin.

124. The method of item 112, wherein the γ-glutamyl carboxylase inhibitor is calumenin.

125. The method of item 112, wherein the vitamin K antagonist or the γ-glutamyl carboxylase inhibitor is administered orally.

126. The method of item 112, wherein the vitamin K antagonist or the γ-glutamyl carboxylase inhibitor is administered in combination with a further anticancer drug and/or in combination with radiotherapy.

127. The method of item 112, wherein the subject is a human.

128. The method of item 112, wherein the subject does not suffer from a thrombotic or thromboembolic disorder.

The invention will now be described by reference to the following examples which are merely illustrative and are not to be construed as a limitation of the scope of the present invention.

EXAMPLES

Materials and Methods
Cell Culture

KBM7 cells were grown in Iscove's modified Dulbecco's medium supplemented with 10% fetal bovine serum (Thermo Fisher Scientific, Waltham, Mass., USA) and 1% penicillin/streptomycin (Sigma-Aldrich, St Louis, Mo., USA). AR KO KBM7 cells were obtained from Haplogen (Vienna, Austria). LNCaP (ATCC, Manassas, Va., USA, CRL-1740) and PC-3 (ATCC, CRL-1435) cells were grown in RPMI-1640 supplemented with 10% fetal bovine serum (Thermo Fisher Scientific) and 1% penicillin/streptomycin (Sigma-Aldrich). For steroid-deprived experiments, LNCaP cells were cultured in RPMI-1640 supplemented with 10% charcoal stripped fetal bovine serum (Thermo Fisher Scientific) and 1% penicillin/streptomycin (Sigma-Aldrich).

KBM7 Cells Viability Screen

CLOUD drugs and combinations thereof were transferred on 384-well plates using an acoustic liquid handler (Echo, Labcyte, Sunnyvale, Calif., USA) and 5,000 cells/well were dispensed on top of the drugs using a dispenser (Thermo Fisher Scientific) for a total of 50 μl/well. Viability was measured after 72 hours using CellTiter-Glo (Promega, Fitchburg, Wis., USA) in a multilabel plate reader (EnVision, PekinElmer, Waltham, Mass., USA). Signal was then normalized to negative (DMSO) and positive (10 μM dasatinib) controls and set between 0 and 100. Noisy compounds, defined according to median absolute deviation (MAD), were excluded from the analysis together with their corresponding combinations. Drug combinations were analyzed according to the Bliss independence model (Bliss C I, *Ann Appl Biol,* 1939, 26:585-615). Briefly, the effect of the combination of drug A and drug B can be predicted to be $C=A+B-A*B$ where A and B are the effects of the single drugs expressed as fractional inhibition between 0 and 1. A deviation of the experimental value from the Bliss prediction was calculated. Positive deviations denote synergies while negative deviations denote antagonisms. Top hits were selected setting thresholds for deviation (>0.7 for synergies and <−0.5 for antagonisms) and Z score (>1). 254 hits were selected and tested again in a counter-screen. The top 20 validated synergies and antagonisms were further validated in 4 concentrations dose-response matrices and analyzed in a similar manner. Here, synergisms and antagonisms were measured calculating differential volumes representing the sum of all deviation values within a specific matrix. Differential volumes>1 indicate robust synergies while differential volumes<−1 indicate robust antagonisms.

Reverse Transcription Quantitative Polymerase Chain Reaction

The RNeasy kit (Qiagen, Venlo, Netherlands) was used to extract RNA. cDNA was produced and reverse transcription quantitative polymerase chain reaction performed using the High Capacity cDNA Reverse Transcription kit and the SYBR Green Master mix from Thermo Fisher Scientific. Reverse transcription quantitative polymerase chain reaction was performed on a LightCycler 480 (Roche, Basel, Switzerland). Primers are listed in the following Table 1:

TABLE 1 qPCR primers used

| Primer | 5'-Sequence-3' |
|---|---|
| AR_flank_FW | GAAAGCGACTTCACCGCAC |
| AR_flank_RV | AAAACATGGTCCCTGGCAGT |
| AR_down_FW | TGTACACGTGGTCAAGTGGG |
| AR_down_RV | TGTGCATGCGGTACTCATTG |
| AR45_FW | ACTCTGGCTTCACAGTTTGGA |
| AR45_RV | CGCACAGGTACTTCTGTTTCC |
| KLK3_FW | GGTGACCAAGTTCATGCTGTG |
| KLK3_RV | GTGTCCTTGATCCACTTCCG |
| TMPRSS2_FW | CTGCCAAGGTGCTTCTCATT |
| TMPRSS2_RV | CTGTCACCCTGGCAAGAATC |
| KLK2_FW | CTGTCAGAGCCTGCCAAGAT |
| KLK2_RV | GCAAGAACTCCTCTGGTTCG |
| ACT_FW | CTGTCTGGCGGCACCACCAT |
| ACT_RV | GCAACTAAGTCATAGTCCGC |

Western Blotting

Cells were lysed in RIPA buffer supplemented with a cocktail of protease inhibitors (Roche). Lysates were resolved by sodium dodecyl sulfate-polyacrylamide gel electrophoresis. AR (#5153) and GAPDH (#5174) antibodies were purchased from Cell Signaling Technology (Danvers, Mass., USA). αTUB antibody (ab7291) was purchased from Abcam (Cambridge, UK). Anti-γ-carboxyglutamyl antibody (REF 3570) was purchased from Sekisui Diagnostics (Lexington, Mass., USA).

Immunofluorescence

After washing with PBS cells were fixed with methanol for 1 h at −20° C. A 3% bovine serum albumin (Sigma-Aldrich), 0.1% Triton (Sigma-Aldrich) PBS buffer was used to block for 20 min. AR antibody (Cell Signaling Technology, #5153) diluted in the blocking buffer was then added to the cells for 30 min at room temperature. After washing, cells were incubated with secondary antibody (Alexa Fluor 488 Goat Anti-Rabbit, Thermo Fisher Scientific) and DAPI (4,6-diamidino-2-phenylindole) diluted in blocking buffer for 30 min at room temperature in the dark. Cells were finally washed with PBS and analyzed using an Operetta microscope (PerkinElmer, Waltham, Mass., USA).

Apoptosis Assay

In all, 50,000 cells/well were seeded in 6-well plates and treated with DMSO, 15 μM flutamide, 35 μM PPC or flutamide and PPC in combination after 24 h. After 3 days, cells were labeled with Alexa Fluor 647 Annexin V antibody (Biolegend, San Diego, Calif., USA) and propidium iodide and analyzed using flow cytometry (BD FACSCalibur, BD Biosciences, Franklyn Lake, N.J., USA).

Cellular Thermal Shift Assay

LNCaP cells were treated with DMSO or 35 μM PPC for 2 days and then harvested maintaining a constant concentration of PPC in all subsequent handling buffers. Otherwise, lysates were directly treated with the drug as already described (Martinez Molina D et al., Science, 2013, 341: 84-7).

Immunoprecipitation

Cells were lysed in IP buffer (50 mM Tris pH 8, 150 mM NaCl, 1% Igepal) supplemented with a cocktail of protease inhibitors (Roche). Immunoprecipitations were performed at 4° C. and using Dynabeads Protein G (Thermo Fisher Scientific). Lysates were precleared with beads for 30 minutes, incubated with antibodies overnight (1 μg antibody was used for 50 μg protein) and immunoprecipitated for 2 hours. After washing, immunoprecipitated proteins were eluted by either boiling in Laemmli buffer or using 50 mM glycine pH 2.8.

2D Gel Electrophoresis

IP lysates eluted with glycine buffer were used for 2D difference gel electrophoresis (DIGE). Buffer was exchanged to DIGE sample buffer (30 mM Tris, pH 8.5, 7 M urea, 2 M thiourea, 4% 3-[(3-Cholamidopropyl) dimethylammonio]-1-propanesulfonate (CHAPS), 1 mM EDTA) using ultrafiltration columns (Millipore) and pH was adjusted to 8.5 as described in Rudashevskaya E L et al., Nat Protoc, 2013, 8(1):75-97. Proteins were labeled with 200 pmol G-Dye200 (sample) or G-Dye300 (internal pooled standard) cyanine dyes (Refraction-2D, NH DyeAGNOSTICS, Halle, Germany) according to the manufacturer's protocol. Rehydration and isoelectric focusing on IPG strips (ReadyStrip IPG Strips, 11 cm, pH 3-10, non-linear (Bio-Rad)) was followed by SDS-PAGE on gradient gels (Criterion, Any kD, BioRad) and detection with a Typhoon fluorescence scanner at the recommended excitation and emission wavelengths for G-Dye200 and G. Images were analyzed using Delta2D 4.3 software (Decodon, Greifswald, Germany).

Liquid Chromatography Mass Spectrometry (LCMS)

Tryptically-digested AR was analysed on a nano-HPLC system (Agilent Technologies, Palo Alto, Calif.) coupled to an linear trap quadrupole (LTQ) orbitrap velos mass spectrometer (ThermoFisher Scientific, Waltham, Mass.) essentially as described in Huber M L et al., J Proteome Res, 2014, 13(2):1147-55.

Example 1: Generation of the STEAM, a Library of Systemically Active Small Molecules, and the CLOUD, a Representative Library of Approved Drugs In order to generate a representative library of clinical compounds, a complete list of all approved FDA products was retrieved from the Drugs@FDA Database (www.fda.gov). This resource contains prescription and over-the-counter small molecules and therapeutic biologicals approved for human use together with drugs discontinued for reasons other than safety (e.g., for economic reasons). First, the 2,171 unique active pharmaceutical ingredients responsible for the biological effects of the 26,800 products retrieved from the database were determined and extracted (see FIG. 1A). Information on biological activity, CAS numbers, canonical smiles, and molecular weights was retrieved mainly from the DrugBank or the Therapeutic Target Database. Other sources included Clarke's Analysis of Drugs and Poisons, the KEGG drug database, the Handbook of Clinical DrugData, and Martindale.

In order to obtain a small molecule collection suitable for HTS, all macromolecules (e.g., enzymes, antibodies, polysaccharides) were discarded, narrowing the set down to 1,929 small molecules. All salt fragments were removed and only 1,416 unique molecular entities were kept. Furthermore, all FDA-approved molecules exerting their biological effects through mechanisms other than protein-ligand interaction or that are not used to treat diseases (e.g., diagnostic agents, dietary supplements, disinfectants, blood substitutes, perfusion solutions, metabolism products, surfactants, stomatological preparations, throat preparations) or that can only be found in topical products (e.g., dermatologicals, nail polish) were removed. This filtering scheme produced a collection of 955 systemically active small molecules that were called the STEAM (SysTEmic smAll Molecules), as shown in FIG. 1F.

To condense the STEAM into the CLOUD, 35 drugs with unknown target were temporarily removed. The remaining small molecules were annotated with their biological activity and grouped into classes accordingly (see FIG. 1F). 920 STEAM drugs have known biological targets and could be classified. Each class contains all drugs targeting the same protein family (e.g., androgen receptor, histone deacetylase) with the same mechanism of action (e.g., agonist, antagonist). Drugs belonging to the same class are often structurally very similar. This is due to many so-called "me too" drugs (Plenge R M et al., Nat Rev Drug Discov, 2013, 12:581-94) developed by competing pharmaceutical companies. While minor structural differences might change important pharmacological parameters and side effects in vivo, it was reasoned that structurally very similar molecules belonging to the same target class would behave redundantly in most screening assays. Therefore, it was decided to keep only representative compounds for each of these classes.

All drugs within a specific class were clustered according to their chemical structure and selected molecules at cluster centers. Structural clustering was performed using a Pipeline Pilot protocol (Accelrys, San Diego, Calif., USA). Structures were represented as Extended Connectivity Fingerprints (ECFP) and the Tanimoto coefficient was applied as a measurement of structural distance. For cluster formation, the Tanimoto dissimilarity was set to 0.85. If this threshold could not cover most of the therapeutic activities within a drug class, the threshold was lowered in a stepwise procedure. The script was used to identify the cluster centers within each of the 176 drug classes. All cluster centers were kept.

Thus, for example, out of four structurally very similar dihydrofolate reductase inhibitors only methotrexate was selected by the clustering algorithm (see FIG. 1A). However, some drug classes are populated by structurally different molecules. For instance, histone deacetylases can be inhibited by the small hydroxamic acid vorinostat and the cyclic peptide romidepsin. In such cases all different structures were kept (see FIG. 1B). Moreover, certain drug classes cover a broader range of therapeutic activities; one example is serotonin receptor agonists that depending on the targeted receptor subtypes can be used to treat anxiety (5-HT1A), migraine (5-HT1B/1D/1F) and disorders of gastrointestinal motility (5-HT4). For such drug classes the clustering parameters were relaxed to allow for the selection of structurally more related compounds covering a broader range of therapeutic indications (see FIG. 1F).

Structural clustering of the 176 classes resulted in 239 representative drugs optimized for chemical diversity and coverage of biological activities. To enable detection of compound activity in both biochemical and cellular assays, the literature was searched for prodrugs among these 239 molecules. Thereby, 35 prodrugs were identified for which the corresponding active form was added to the screening collection (see FIG. 1G). Finally, the 35 STEAM drugs with unknown target were included to arrive at a final collection of 309 approved small molecules that was named the CLOUD—the CeMM Library of Unique Drugs. The CLOUD covers more drug classes compared to other commercially available libraries containing FDA-approved drugs (see FIG. 2A) and exclusively provides active forms of prodrugs (see FIG. 2B).

The clustering procedure was further addressed for potential biases in target organisms, target proteins or physicochemical properties. The 920 STEAM drugs with known mechanism of action target mostly human proteins (80%) followed by bacterial (14%), viral (4%), protozoal, fungal and helminthic (2%) targets, as shown in FIG. 3A. CLOUD drugs showed a similar distribution with a minor reduction in drugs targeting bacterial proteins (see FIG. 3A): this difference is easily explained by the high number of structurally similar antibiotics acting on dihydropteroate synthase, penicillin-binding proteins and the ribosome. A protein target classification of STEAM drugs showed that the majority of approved small molecules target G protein-coupled receptors (GPCRs, 27%, see FIG. 3B) as already reported (Overington J P et al., Nat Rev Drug Discov, 2006, 5:993-6). Other prominent targets are ion channels (14%), oxidoreductases (10%), transferases (8%), nuclear receptors (7%) and hydrolases (7%). Again, CLOUD compounds showed a similar pattern (see FIG. 3B). Furthermore, orally bioavailable drugs usually adhere to the so-called Lipinski's rule of five (Lipinski C A et al., Adv Drug Deliv Rev, 2001, 46:3-26) and approximately 80% of CLOUD and STEAM drugs do not violate this rule (see FIG. 1C). Moreover, when the physicochemical properties contemplated by the Lipinski's rule of five (i.e., molecular weight, hydrogen bond acceptors/donors, hydrophobicity (log P)) as well as the number of rotatable bonds were analyzed individually (using the chemistry components of the software Pipeline Pilot (Accelrys)), no significantly different distribution was observed comparing the CLOUD to the STEAM, as also shown in FIGS. 4A to 4E. This confirmed that the 239 CLOUD drugs with known target did not only reflect the target distribution but also covered the chemical space of the 955 STEAM compounds (i.e., the 955 initially selected FDA-approved small molecules).

Approved drugs have been extensively annotated with pharmacological data including peak plasma concentrations in humans. These concentrations vary over several orders of magnitude (see FIG. 1D). In order to reproduce conditions close to clinical settings, stocks of CLOUD drugs were prepared enabling screens in the range of their respective plasma concentrations. Furthermore, all CLOUD compounds were arranged in a single 384-well plate with the aim of creating an easily accessible reference library for repurposing and annotating clinical compounds.

The corresponding compounds were mainly purchased from Enamine Ltd (Kiev, Ukraine), Toronto Research Chemical (Toronto, Canada) and Sigma-Aldrich. Controlled substances and unstable/unavailable compounds are indicated in FIGS. 1F and 1G. The CLOUD will be distributed by Enamine Ltd.

Finally, to ensure that this library functionally preserved most of the biological activities addressed by STEAM drugs, gene expression profiles reported in the Connectivity Map (CMap) (Lamb J et al., *Science,* 2006, 313:1929-35) for compounds belonging to the same class were analyzed. To eliminate batch-effects from CMap data, DIPS scores were used (Iskar M et al., *PLoS Comput Biol,* 2010, 6:1000925), which provide efficient data normalization. Pairwise DIPS scores within CLOUD clusters are significantly increased compared to random drug pairs, indicating a similar influence of co-clustered drugs on cellular responses (see FIG. 1E).

Example 2: Synergistic Interaction Between the Antiandrogen Flutamide and the Vitamin K Antagonist Phenprocoumon Drug repurposing has already produced successful new applications of approved drugs (Brynner R et al., Dark Remedy: The Impact of Thalidomide and Its Revival as a Vital Medicine, *Perseus Publishing, Cambridge,* 2001; Renaud R C et al., *Nat Rev Drug Discov,* 2002, 1:663-4). More recently, it has been emphasized that combinations of different molecules can improve the outcome of pharmacological therapies (Bock C et al., *Nat Rev Cancer,* 2012, 12:494-501). The CLOUD allows for effective combinatorial screenings of clinical compounds using different assays.

In one such screen the inventors investigated the effect of 40,470 pairwise combinations of CLOUD drugs on the viability of KBM7 cells, a near haploid human chronic myeloid leukemia (CML) cell line (Kotecki M et al., *Exp Cell Res,* 1999, 252:273-80) that allows for rapid downstream functional characterizations of drug targets and mechanisms of action (Reiling J H et al., *Proc Natl Acad Sci USA,* 2011, 108:11756-65; Winter G E et al., *Nat Chem Biol,* 2014, 10:768-73). Combinations of CLOUD drugs were analyzed for potential synergy or antagonism according to the Bliss independence model (Bliss C I, *Ann Appl Biol,* 1939, 26:585-615) and 254 hits were selected for a counter-screen (see FIG. 5A). The top 20 synergies and antagonisms were then selected among the hits that validated in the counter-screen (see FIG. 5B and FIG. 6), and these were further investigated in dose-response matrices. The synergistic interaction between flutamide and PPC stood out as the most significant hit of the screen (see FIG. 7 and FIG. 5C).

KBM7 cells enable the rapid generation of human gene knockouts by insertional mutagenesis (Carette J E et al., *Science,* 2009, 326:1231-5; Burckstummer T et al., *Nat Methods,* 2013, 10:965-71). In order to validate the specificity of the target, and hypothesizing that the synergistic interaction between flutamide and PPC relies on the presence of the androgen receptor, the effect of the drug combination was addressed on a KBM7 clone carrying a gene-trap in the AR gene (AR KO KBM7). First, the knockout of the AR gene was validated using reverse transcription quantitative polymerase chain reaction (RT-qPCR) (see FIG. 5D) and western blotting (see FIG. 5E). Upon treatment with different concentrations of flutamide and PPC in combination, AR KO KBM7 cells showed increased resistance compared to wild type KBM7 cells (see FIG. 5F). A closer inspection of the position of the gene-trap locus revealed an AR isoform (AR45) (Dehm S M et al., *Endocr Relat Cancer,* 2011, 18:R183-96) downstream of the inserted cassette (see FIG. 8A). The presence of this alternative isoform and residual transcripts of the full length AR in AR KO KBM7 cells (see FIG. 8B) might explain the incomplete resistance to the combination.

These results indicate that the combination of an antiandrogen, such as flutamide, with a vitamin K antagonist, such as phenprocoumon, exerts a synergistic effect for killing androgen receptor positive cancer cells.

Example 3: Combinations of an Antiandrogen and a Vitamin K Antagonist Act Synergistically to Induce Apoptosis in Prostate Cancer Cells Carrying an Androgen Receptor T877A Mutation (LNCaP Cells)

Androgen receptor (AR) signaling has been shown to play a crucial role in the development of prostate cancer (Mills I G, *Nat Rev Cancer,* 2014, 14:187-98) and current pharmacological treatments aim at reducing androgen levels or inhibiting the pathway, i.e. downstream signaling, with AR antagonists (Taplin M E, *Nat Clin Pract Oncol,* 2007, 4:236-44). Even though patients tend to initially respond well to antiandrogen therapy, cancer cells inevitably develop resistance mechanisms hampering the efficacy of the treatment (Chen C D et al., *Nat Med,* 2004, 10:33-9). Drug combinations can circumvent or delay the development of drug resistance mechanisms and the use of already approved drugs entails different pharmacological and clinical benefits.

In order to evaluate the translational potential of both the CLOUD and the synergistic interaction uncovered in the combinatorial screen described in Example 2 above, the inventors assessed the effect of the combination of flutamide and phenprocoumon on prostate cancer cell lines. Dose-response measurements were performed with LNCaP cells, an AR-dependent prostate cancer cell line carrying a T877A mutation in the AR gene (Veldscholte J et al., *J Steroid Biochem Mol Biol,* 1992, 41:665-9). This mutation has been detected in prostate cancer patients (Gaddipati J P et al., *Cancer Res,* 1994, 54:2861-4) and reported to confer resistance to AR antagonists. LNCaP cells showed a marked sensitivity to the combination of flutamide and phenprocoumon while PC-3 prostate cancer cells, which express almost undetectable amounts of AR (Alimirah F et al., *FEBS Lett,* 2006, 580:2294-300), were only mildly affected at very high concentrations (see FIG. 9A and FIG. 10). To rule out a contribution from basal AR signaling activation due to the presence of endogenous ligands, the dose-response treatment was repeated in steroid-deprived conditions, confirming the sensitivity of LNCaP cells to the combination (see FIG. 12).

Next, it was asked whether the synergistic compounds could be exchanged for other members of the drug classes they represent in the CLOUD. Phenprocoumon was chosen as representative vitamin K epoxide reductase inhibitor or vitamin K antagonist, a drug class that also includes warfarin. Of note, treatment of LNCaP cells with the combination of flutamide and warfarin resulted in a synergistic toxicity similar to that observed with phenprocoumon (see FIG. 11A). Flutamide is the representative androgen receptor antagonist in the CLOUD and other drugs in this class include bicalutamide, enzalutamide, and nilutamide. When these compounds were tested in combination with phenprocoumon in LNCaP cells, strong synergy was observed for bicalutamide (see FIG. 11A). Thus, similar results were obtained when exchanging phenprocoumon with warfarin, another VKORC1 inhibitor, or flutamide with bicalutamide, another AR antagonist (see FIG. 11A). Two other antiandrogens, namely enzalutamide and nilutamide, also showed a synergistic interaction with phenprocoumon, albeit to a lower extent compared to flutamide (see FIG. 11B). Overall, these data show that combinations of antiandrogens and vitamin K antagonists synergistically lead to LNCaP prostate cancer cell death and corroborate the concept behind the CLOUD.

To better elucidate the mechanism of cell death triggered by the combination of flutamide and phenprocoumon, propidium iodide/Annexin V staining was performed, followed by flow cytometry analysis of LNCaP cells treated with the two drugs either alone or in combination. Only the treatment with both flutamide and phenprocoumon induced apoptosis in this AR-dependent prostate cancer cell line, as shown in FIG. 9B.

These results show that the combination of an antiandrogen, such as flutamide, bicalutamide, enzalutamide or nilutamide, with a vitamin K antagonist, such as phenprocoumon or warfarin, provides a synergistical inhibition of the growth of androgen receptor dependent cancer cells. This advantageous effect has been achieved in a prostate cancer cell line having an androgen receptor T877A mutation which is known to confer resistance to monotherapeutic treatment with antiandrogens, thus indicating that vitamin K antagonists like phenprocoumon can be used to resensitize antiandrogen-resistant prostate cancer to the treatment with an antiandrogen such as flutamide. The combination of an antiandrogen with a vitamin K antagonist consequently allows a particularly effective treatment of prostate cancer and other androgen receptor positive cancers, including also antiandrogen-resistant prostate cancer.

Example 4: The Vitamin K Antagonist Phenprocoumon Modulates Binding of the Antiandrogen Flutamide to the Androgen Receptor, Such that the Binding of Flutamide in the Presence of Phenprocoumon Leads to Androgen Receptor Degradation To further dissect the mechanism of action behind the synergistic interaction described in Examples 2 and 3 above, the effect of the combination of flutamide and phenprocoumon on androgen receptor (AR) signaling was analyzed. In particular, the dose-response treatment of LNCaP cells was repeated in the absence of steroids, confirming the sensitivity of these cells to the combination of flutamide and phenprocoumon (see FIG. 12). RT-qPCR experiments confirmed that flutamide alone behaves indeed as an AR agonist in the LNCaP cells harboring a T877A mutant AR, as the drug increased the expression of AR signaling canonical targets such as KLK3, TMPRSS2 and KLK2 after 24 hours treatment (see FIG. 13A). In contrast, phenprocoumon alone did not affect the expression of these genes. Notably, treatment of LNCaP cells with both flutamide and phenprocoumon restrained the expression of KLK3 and KLK2 to levels similar to vehicle treatment (see FIG. 13A) and decreased AR expression (see FIG. 13A), as if flutamide would behave more as an antagonist in this context. As phenprocoumon alone did not interfere with the induction of AR signaling promoted by the potent synthetic agonist R1881 (see FIG. 15), it was concluded that the vitamin K antagonist does not abolish binding of AR ligands to the receptor.

The downregulation of AR mRNA levels upon treatment of LNCaP cells with the combination of flutamide and phenprocoumon could reflect a lower transcription rate or decreased mRNA stability. The turnover of AR mRNA in the presence of a transcription inhibitor was assessed over 10 hours and no difference was found between LNCaP cells treated with either DMSO or the drug combination (see FIG. 13E). In addition to AR transcripts, also AR protein levels were downregulated upon co-administration of flutamide and phenprocoumon as assessed by immunofluorescence (see FIG. 13C) and western blotting (see FIG. 13B). Thus, treatment of LNCaP cells with the combination of flutamide and phenprocoumon resulted in decreased AR expression both at the mRNA (see FIG. 13A) and at the protein level as observed in both western blotting (see FIG. 13B) and immunofluorescence (see FIG. 13C) experiments. Notably, AR expression already decreased after 8 hours treatment (see FIG. 14). Treatment of LNCaP cells with the proteasome inhibitor bortezomib reduced AR protein levels as already described (Bhattacharyya R S et al., *Mol Cancer Ther*, 2006, 5(6):1539-49) (see FIG. 13F) and could partly restore the levels of AR upon co-administration with flutamide and phenprocoumon (see FIG. 13F). In addition, turnover measurements revealed decreased AR half-life in LNCaP cells treated with the combination (see FIG. 13G). These results indicate that in the presence of phenprocoumon, flutamide antagonizes the T877A mutated AR of LNCaP cells. The concomitant administration of flutamide and phenprocoumon to LNCaP cells leads to AR degradation occurring, at least in part, via the proteasome.

Example 5: The Androgen Receptor is Post-Translationally Modified by γ-Carboxylation Phenprocoumon acts as an anticoagulant by inhibiting vitamin K epoxide reductase, thereby preventing γ-carboxylation of glutamic acid residues of proteins involved in the coagulation cascade. The inventors hypothesized that this post-translational modification could also occur on glutamic acid residues of the androgen receptor (AR) and induce global conformational changes affecting protein stability and ligand binding. First, the inventors excluded direct engagement of AR by phenprocoumon performing a cellular thermal shift assay (CETSA), a recently described technique (Martinez Molina D et al., *Science*, 2013, 341:84-7) for the measurement of cellular interactions between proteins and small molecules. CETSA measurements showed that phenprocoumon indeed affects the thermal stability of AR (see FIG. 13D). However, this shift in stability was observed only upon administration of phenprocoumon to LNCaP cells for 2 days before the experiment. In the absence of such a pretreatment, the addition of phenprocoumon to the cell lysate did not stabilize AR (see FIG. 13D), arguing against a direct engagement of the receptor by phenprocoumon. The inventors then assessed whether phenprocoumon treatment could otherwise modify AR and analyzed the migration pattern of the protein by means of 2D gel electrophoresis (see FIG. 13H). Non-overlapping spots were observed when comparing AR immunoprecipitated from LNCaP cells treated with either DMSO or phenprocoumon. Overall, AR from cells treated with phenprocoumon migrated at a higher isoelectric point, consistent with decreased negative charge due to inhibition of γ-carboxylation. Next, it was tested whether LNCaP cells were indeed capable of γ-glutamyl carboxylating protein substrates by detecting global γ-carboxylation levels. Blotting with an antibody recognizing γ-carboxylation in a sequence-independent context revealed several background bands over a wide molecular weight range (see FIG. 13I). However, addition of vitamin K, the co-substrate of γ-glutamyl carboxylase, increased the abundance of few selected bands, the most prominent appearing in correspondence of the molecular weight of the AR. Interestingly, the same γ-carboxylation-specific antibody could pull-down AR from LNCaP cell lysates and phenprocoumon treatment reduced the amount of immunoreciptated protein in a dose-dependent manner (see FIG. 13J). Finally, to identify potential AR γ-carboxylation sites, the nuclear receptor from LNCaP cells treated with vitamin K was immunoprecipitated. Following sample preparation procedures previously described for γ-carboxylated substrates (Hallgren K W et al., *J Proteome Res*, 2013, 12(6): 2365-74), the samples were analyzed by liquid chromatography mass spectrometry (LCMS). A total of 19 AR-derived peptides were detected and γ-carboxylation was observed on the glutamic acid residues E2 and E93 of AR (see FIG. 13K). Altogether, these results indicate that the combination of phenprocoumon and flutamide affects the stability of the AR and its downstream signaling. In particular, it has been shown that AR is γ-carboxylated and that this post-translational modification is inhibited by phenprocoumon.

The invention claimed is:

1. A pharmaceutical composition comprising: an antiandrogen, wherein the antiandrogen is flutamide, nilutamide, bicalutamide, enzalutamide, or a pharmaceutically acceptable salt or solvate of any of these agents; a vitamin K antagonist, wherein the vitamin K antagonist is phenprocoumon or warfarin; and a pharmaceutically acceptable excipient.

2. The pharmaceutical composition of claim 1, wherein the antiandrogen is flutamide or a pharmaceutically acceptable salt or solvate thereof.

3. The pharmaceutical composition of claim 1, wherein the vitamin K antagonist is phenprocoumon.

4. The pharmaceutical composition of claim 1, wherein the vitamin K antagonist is warfarin.

5. The pharmaceutical composition of claim 1, wherein the antiandrogen is flutamide or a pharmaceutically acceptable salt or solvate thereof, and wherein the vitamin K antagonist is phenprocoumon.

* * * * *